United States Patent
Sanders et al.

(10) Patent No.: US 9,636,278 B2
(45) Date of Patent: May 2, 2017

(54) SYSTEM FOR CLOSED TRANSFER OF FLUIDS WITH A LOCKING MEMBER

(71) Applicant: Becton Dickinson and Company Limited, Dun Laoghaire (IE)

(72) Inventors: Laurie Sanders, Glen Ridge, NJ (US); Yan Yevmenenko, New York, NY (US)

(73) Assignee: Becton Dickinson and Company Limited, Dun Laoghaire (IE)

( * ) Notice: Subject to any disclaimer, the term of this patent is extended or adjusted under 35 U.S.C. 154(b) by 0 days.

(21) Appl. No.: 14/532,165

(22) Filed: Nov. 4, 2014

(65) Prior Publication Data
US 2015/0123398 A1 May 7, 2015

Related U.S. Application Data

(60) Provisional application No. 61/900,674, filed on Nov. 6, 2013.

(51) Int. Cl.
*A61J 1/20* (2006.01)
*A61M 39/10* (2006.01)
(Continued)

(52) U.S. Cl.
CPC ........... *A61J 1/2096* (2013.01); *A61J 1/1406* (2013.01); *A61J 1/1481* (2015.05); *A61J 1/201* (2015.05);
(Continued)

(58) Field of Classification Search
CPC ...... A61J 1/1406; A61J 1/1418; A61J 1/1481; A61J 1/201; A61J 1/2055; A61J 1/2058;
(Continued)

(56) References Cited

U.S. PATENT DOCUMENTS 3,990,727 A * 11/1976 Gallagher ............. F16L 37/084
285/148.2
4,423,892 A * 1/1984 Bartholomew ..... F16L 37/0987
285/305
(Continued)

FOREIGN PATENT DOCUMENTS

EP 2462971 A1 6/2012
WO 2004033023 A1 4/2004
(Continued)

*Primary Examiner* — Adam Marcetich
(74) *Attorney, Agent, or Firm* — The Webb Law Firm

(57) ABSTRACT

A connector system for a medical device includes a first connector having an elongate opening, and a second connector including a lock portion, where the first connector is movable relative to the second connector between an initial position where the first connector is not in fluid communication with the second connector and an activated position where the first connector is in fluid communication with the second connector. The system also includes a locking member connected to the first connector. The locking member is transitionable between an unlocked position where the second connector is movable within the elongate opening of the first connector and a locked position where the locking member is configured to engage the lock portion of the second connector to lock the first connector to the second connector in the activated position. The locking member comprises a spring body received by the elongate opening of the first connector.

15 Claims, 72 Drawing Sheets

(51) Int. Cl.
*A61J 1/14* (2006.01)
*F16L 37/14* (2006.01)
*F16L 37/084* (2006.01)

(52) U.S. Cl.
CPC ........... *A61J 1/2058* (2015.05); *A61J 1/2075* (2015.05); *A61J 1/2089* (2013.01); *A61M 39/1011* (2013.01); *A61J 1/2055* (2015.05); *A61M 2039/1016* (2013.01); *A61M 2039/1027* (2013.01); *F16L 37/084* (2013.01); *F16L 37/0841* (2013.01); *F16L 37/142* (2013.01); *F16L 37/144* (2013.01); *Y10S 285/921* (2013.01); *Y10S 604/905* (2013.01)

(58) Field of Classification Search
CPC ...... A61J 1/2075; A61J 1/2089; A61J 1/2096; A61J 2200/70; A61M 2039/1027; A61M 39/1011; F16L 37/0841; F16L 37/0842; F16L 37/086; F16L 37/088; F16L 37/091; F16L 37/092; F16L 25/0045; F16L 37/08; F16L 37/084; F16L 37/0985
See application file for complete search history.

(56) References Cited

U.S. PATENT DOCUMENTS

| | | |
|---|---|---|
| 4,436,125 A | 3/1984 | Blenkush |
| 4,564,054 A | 1/1986 | Gustavsson |
| 4,632,436 A * | 12/1986 | Kimura ............... F16L 37/0841 285/305 |
| 4,673,404 A | 6/1987 | Gustavsson |
| 4,844,512 A * | 7/1989 | Gahwiler ............. F16L 37/084 285/275 |
| 4,932,937 A | 6/1990 | Gustavsson et al. |
| 5,033,777 A * | 7/1991 | Blenkush ............ F16L 37/0841 285/317 |
| 5,052,725 A * | 10/1991 | Meyer ................. F16L 37/0841 285/308 |
| 5,090,747 A * | 2/1992 | Kotake ................... F16B 21/16 285/305 |
| 5,104,158 A | 4/1992 | Meyer et al. |
| 5,122,129 A | 6/1992 | Olson et al. |
| 5,280,876 A | 1/1994 | Atkins |
| 5,290,254 A | 3/1994 | Vaillancourt |
| 5,322,518 A | 6/1994 | Schneider et al. |
| 5,334,188 A | 8/1994 | Inoue et al. |
| 5,360,011 A | 11/1994 | McCallister |
| 5,374,088 A * | 12/1994 | Moretti ............... F16L 37/0841 285/305 |
| 5,395,348 A | 3/1995 | Ryan |
| 5,437,650 A | 8/1995 | Larkin et al. |
| 5,464,123 A | 11/1995 | Scarrow |
| 5,472,430 A | 12/1995 | Vaillancourt et al. |
| 5,478,328 A | 12/1995 | Silverman et al. |
| 5,487,728 A | 1/1996 | Vaillancourt |
| 5,507,733 A | 4/1996 | Larkin et al. |
| 5,509,911 A | 4/1996 | Cottone, Sr. et al. |
| 5,520,420 A * | 5/1996 | Moretti ................. F16L 37/00 285/305 |
| 5,545,152 A | 8/1996 | Funderburk et al. |
| 5,607,392 A | 3/1997 | Kanner |
| 5,609,584 A | 3/1997 | Gettig et al. |
| 5,611,792 A | 3/1997 | Gustafsson |
| 5,647,845 A | 7/1997 | Haber et al. |
| 5,685,866 A | 11/1997 | Lopez |
| 5,807,347 A | 9/1998 | Bonaldo |
| 5,897,526 A | 4/1999 | Vaillancourt |
| 6,063,068 A | 5/2000 | Fowles et al. |
| 6,082,779 A * | 7/2000 | Lesser ................ F16L 37/0841 285/319 |
| 6,089,541 A | 7/2000 | Weinheimer et al. |
| 6,113,583 A | 9/2000 | Fowles et al. |
| 6,132,404 A | 10/2000 | Lopez |
| 6,139,534 A | 10/2000 | Niedospial, Jr. et al. |
| 6,221,041 B1 | 4/2001 | Russo |
| 6,221,056 B1 | 4/2001 | Silverman |
| 6,318,764 B1 * | 11/2001 | Trede .................. F16L 37/0841 285/305 |
| 6,343,629 B1 | 2/2002 | Wessman et al. |
| 6,358,236 B1 | 3/2002 | DeFoggi et al. |
| 6,409,708 B1 | 6/2002 | Wessman |
| 6,474,375 B2 | 11/2002 | Spero et al. |
| 6,478,788 B1 | 11/2002 | Aneas |
| 6,544,246 B1 | 4/2003 | Niedospial, Jr. |
| 6,551,299 B2 | 4/2003 | Miyoshi et al. |
| 6,585,695 B1 | 7/2003 | Adair et al. |
| 6,599,273 B1 | 7/2003 | Lopez |
| 6,610,040 B1 | 8/2003 | Fowles et al. |
| 6,629,958 B1 | 10/2003 | Spinello |
| 6,652,007 B1 * | 11/2003 | Hwang ................. F16L 37/088 285/305 |
| 6,656,433 B2 | 12/2003 | Sasso |
| 6,715,520 B2 | 4/2004 | Andreasson et al. |
| 6,814,726 B2 | 11/2004 | Lauer |
| 6,852,103 B2 | 2/2005 | Fowles et al. |
| 6,875,203 B1 | 4/2005 | Fowles et al. |
| 6,875,205 B2 | 4/2005 | Leinsing |
| 6,911,025 B2 | 6/2005 | Miyahara |
| 6,997,917 B2 | 2/2006 | Niedospial, Jr. et al. |
| 7,040,598 B2 | 5/2006 | Raybuck |
| 7,083,605 B2 | 8/2006 | Miyahara |
| 7,097,209 B2 | 8/2006 | Unger et al. |
| 7,261,707 B2 | 8/2007 | Frezza et al. |
| 7,306,584 B2 | 12/2007 | Wessman et al. |
| 7,326,194 B2 | 2/2008 | Zinger et al. |
| 7,350,535 B2 | 4/2008 | Liepold et al. |
| 7,354,427 B2 | 4/2008 | Fangrow |
| 7,452,349 B2 | 11/2008 | Miyahara |
| 7,547,300 B2 | 6/2009 | Fangrow |
| 7,628,772 B2 | 12/2009 | McConnell et al. |
| 7,648,491 B2 | 1/2010 | Rogers |
| 7,658,734 B2 | 2/2010 | Adair et al. |
| 7,743,799 B2 | 6/2010 | Mosler et al. |
| 7,744,581 B2 | 6/2010 | Wallen et al. |
| 7,758,560 B2 | 7/2010 | Connell et al. |
| 7,803,140 B2 | 9/2010 | Fangrow, Jr. |
| 7,867,215 B2 | 1/2011 | Akerlund et al. |
| 7,879,018 B2 | 2/2011 | Zinger et al. |
| 7,900,659 B2 | 3/2011 | Whitley et al. |
| 7,927,316 B2 | 4/2011 | Proulx et al. |
| 7,942,860 B2 | 5/2011 | Horppu |
| 7,975,733 B2 | 7/2011 | Horppu et al. |
| 8,096,525 B2 | 1/2012 | Ryan |
| 8,122,923 B2 | 2/2012 | Kraus et al. |
| 8,123,738 B2 | 2/2012 | Vaillancourt |
| 8,137,332 B2 | 3/2012 | Pipelka |
| 8,167,863 B2 | 5/2012 | Yow |
| 8,177,768 B2 | 5/2012 | Leinsing |
| 8,196,614 B2 | 6/2012 | Kriheli |
| 8,206,367 B2 | 6/2012 | Warren et al. |
| 8,211,069 B2 | 7/2012 | Fangrow, Jr. |
| 8,226,628 B2 | 7/2012 | Muramatsu et al. |
| 8,257,286 B2 | 9/2012 | Meyer et al. |
| 8,267,127 B2 | 9/2012 | Kriheli |
| 8,277,424 B2 | 10/2012 | Pan |
| 8,317,741 B2 | 11/2012 | Kraushaar |
| 8,317,743 B2 | 11/2012 | Denenburg |
| 8,398,607 B2 | 3/2013 | Fangrow, Jr. |
| 8,403,905 B2 | 3/2013 | Yow |
| 8,425,487 B2 | 4/2013 | Beiriger et al. |
| 8,449,521 B2 | 5/2013 | Thorne, Jr. et al. |
| 8,454,579 B2 | 6/2013 | Fangrow, Jr. |
| 2003/0070726 A1 | 4/2003 | Andreasson et al. |
| 2003/0168470 A1 * | 9/2003 | Choi ................... F16L 37/0841 222/14 |
| 2005/0065495 A1 | 3/2005 | Zambaux |
| 2005/0182383 A1 | 8/2005 | Wallen |
| 2005/0215976 A1 | 9/2005 | Wallen |
| 2005/0225082 A1 * | 10/2005 | Dalle .................. A61M 39/1011 285/330 |
| 2006/0165479 A1 * | 7/2006 | Lorenz ................ F16L 37/0841 403/223 |

(56) References Cited

U.S. PATENT DOCUMENTS

| | | |
|---|---|---|
| 2007/0029796 A1* | 2/2007 | Bibby ............... F16L 37/0982 285/308 |
| 2007/0079894 A1 | 4/2007 | Kraus et al. |
| 2007/0249197 A1* | 10/2007 | Spranger ............ A61M 39/1011 439/152 |
| 2008/0012314 A1* | 1/2008 | Harger ............... F16L 37/0982 285/308 |
| 2008/0045919 A1 | 2/2008 | Jakob et al. |
| 2008/0287914 A1 | 11/2008 | Wyatt et al. |
| 2009/0159485 A1 | 6/2009 | Jakob et al. |
| 2009/0230673 A1* | 9/2009 | Freter .................. F16L 37/098 285/93 |
| 2009/0261582 A1* | 10/2009 | Gaudin .............. F16L 37/0841 285/321 |
| 2010/0019483 A1* | 1/2010 | Bokuhn ............... F16L 37/144 285/93 |
| 2010/0052313 A1* | 3/2010 | Ishida .................. F16L 37/088 285/93 |
| 2010/0179506 A1 | 7/2010 | Shemesh et al. |
| 2010/0217226 A1 | 8/2010 | Shemesh |
| 2011/0004183 A1 | 1/2011 | Carrez et al. |
| 2011/0042942 A1* | 2/2011 | Gammons .......... F16L 37/0841 285/308 |
| 2011/0062703 A1 | 3/2011 | Lopez et al. |
| 2011/0074148 A1 | 3/2011 | Imai |
| 2011/0106046 A1 | 5/2011 | Hiranuma et al. |
| 2011/0257621 A1 | 10/2011 | Fangrow |
| 2011/0291406 A1 | 12/2011 | Kraft et al. |
| 2012/0029483 A1 | 2/2012 | Griffith et al. |
| 2012/0035580 A1 | 2/2012 | Fangrow |
| 2012/0046636 A1 | 2/2012 | Kriheli |
| 2012/0123381 A1 | 5/2012 | Kraus et al. |
| 2012/0179128 A1 | 7/2012 | Takemoto et al. |
| 2012/0192968 A1 | 8/2012 | Bonnal et al. |
| 2012/0192976 A1 | 8/2012 | Rahimy et al. |
| 2012/0203193 A1 | 8/2012 | Rogers |
| 2012/0265163 A1 | 10/2012 | Cheng et al. |
| 2012/0279884 A1 | 11/2012 | Tennican et al. |
| 2012/0316536 A1 | 12/2012 | Carrez et al. |
| 2013/0006211 A1 | 1/2013 | Takemoto |
| 2013/0012908 A1 | 1/2013 | Yeung |
| 2013/0066293 A1 | 3/2013 | Garfield et al. |
| 2013/0072893 A1 | 3/2013 | Takemoto |
| 2013/0076019 A1 | 3/2013 | Takemoto |
| 2013/0079744 A1 | 3/2013 | Okiyama et al. |
| 2014/0125051 A1* | 5/2014 | Barthel ................ F16L 37/252 285/33 |
| 2015/0126958 A1* | 5/2015 | Sanders ............ A61M 39/1011 604/414 |
| 2015/0126974 A1* | 5/2015 | Sanders ................ A61J 1/2096 604/533 |

FOREIGN PATENT DOCUMENTS

| | | |
|---|---|---|
| WO | 2005011781 A1 | 2/2005 |
| WO | 2006103074 A1 | 10/2006 |
| WO | 2009024807 A1 | 2/2009 |
| WO | 2009090627 A1 | 7/2009 |
| WO | 2011050333 A1 | 4/2011 |
| WO | 2012069401 A1 | 5/2012 |
| WO | 2012117648 A1 | 9/2012 |
| WO | 2012119225 A1 | 9/2012 |
| WO | 2012168235 A1 | 12/2012 |
| WO | 2013025946 A1 | 2/2013 |
| WO | 2013054323 A1 | 4/2013 |
| WO | 2013066779 A1 | 5/2013 |
| WO | 2013115730 A1 | 8/2013 |
| WO | 2013179596 A1 | 12/2013 |
| WO | 2014102639 A1 | 7/2014 |

\* cited by examiner

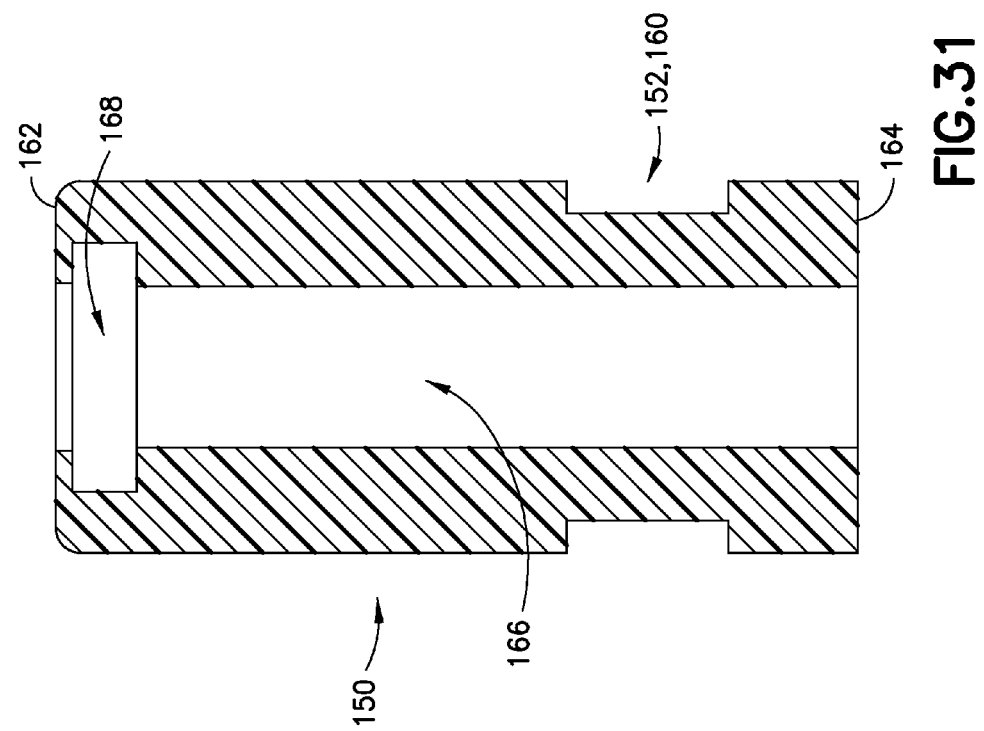
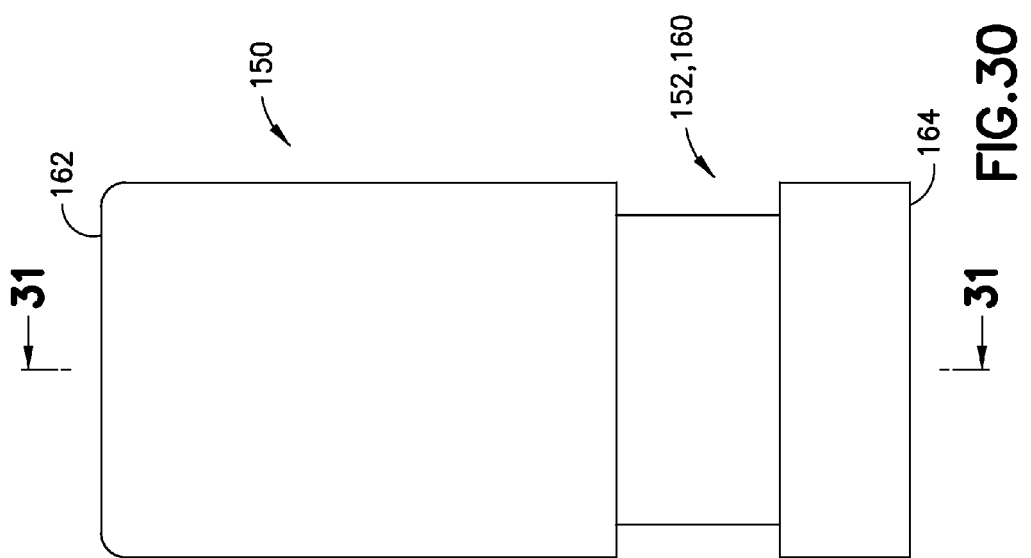

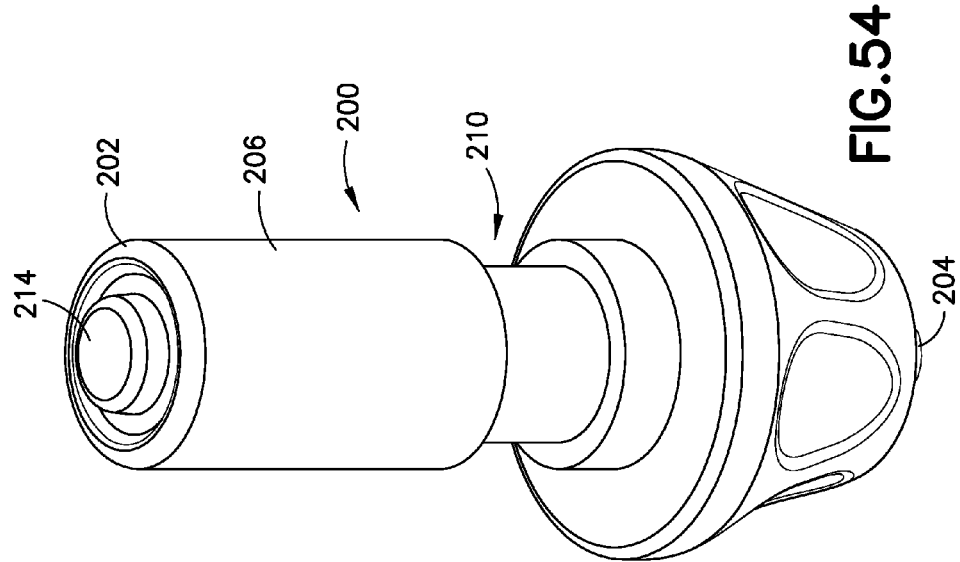
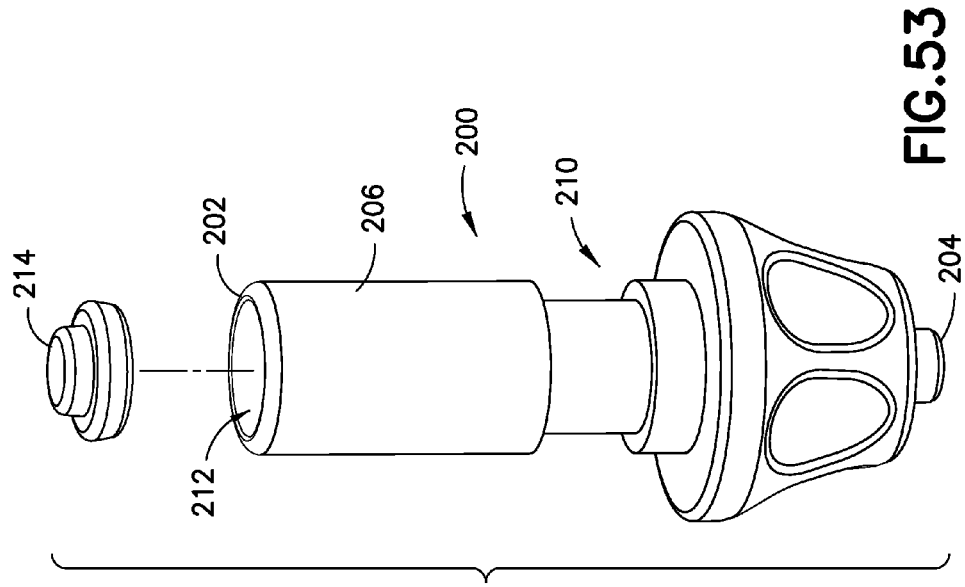

SYSTEM FOR CLOSED TRANSFER OF FLUIDS WITH A LOCKING MEMBER

CROSS-REFERENCE TO RELATED APPLICATION

This application claims priority to U.S. Provisional Application Ser. No. 61/900,674, filed Nov. 6, 2013, which is hereby incorporated by reference in its entirety.

BACKGROUND OF THE INVENTION

1. Field of the Disclosure

The present disclosure relates generally to a system for the closed transfer of fluids. More particularly, the present disclosure relates to a system that provides leak-proof sealing and pressure equalization during engagement of a cannula with a vial, during transfer of a substance from a vial chamber to a barrel chamber via the cannula, and during disengagement of the cannula from the vial.

2. Description of the Related Art

Health care providers reconstituting, transporting, and administering hazardous drugs, such as cancer treatments, can put health care providers at risk of exposure to these medications and present a major hazard in the health care environment. For example, nurses treating cancer patients risk being exposed to chemotherapy drugs and their toxic effects. Unintentional chemotherapy exposure can affect the nervous system, impair the reproductive system, and bring an increased risk of developing blood cancers in the future. In order to reduce the risk of health care providers being exposed to toxic drugs, the closed transfer of these drugs becomes important.

Some drugs must be dissolved or diluted before they are administered, which involves transferring a solvent from one container to a sealed vial containing the drug in powder or liquid form, by means of a needle. Drugs may be inadvertently released into the atmosphere in gas form or by way of aerosolization, during the withdrawal of the needle from the vial and while the needle is inside the vial if any pressure differential between the interior of the vial and the surrounding atmosphere exists.

SUMMARY OF THE INVENTION

In one aspect, a connector system for a medical device includes a first connector having an elongate opening, and a second connector including a lock portion, where the first connector is movable relative to the second connector between an initial position where the first connector is not in fluid communication with the second connector and an activated position where the first connector is in fluid communication with the second connector. The system also includes a locking member connected to the first connector. The locking member is transitionable between an unlocked position where the second connector is movable within the elongate opening of the first connector and a locked position where the locking member is configured to engage the lock portion of the second connector to lock the first connector to the second connector in the activated position. The locking member comprises a spring body received by the elongate opening of the first connector.

The spring body may be deformable between a rested state when the locking member is in the locked position and a biased state when the locking member is in the unlocked position, with the spring body configured to return to the rested state. The spring body may at least partially block the elongate opening of the first connector when the spring body is in the rested state, with the spring body open to receive the second connector when the spring body is in the biased state. The locking member may further include first and second buttons secured to the spring body, where moving the first and second buttons radially inward transitions the spring body from the rested state to the biased state and moves the locking member to the unlocked position. The spring body may be annular with the first and second buttons positioned on opposite sides of the spring body from each other. The first button may be connected to the spring body by a first connecting arm and the second button is connected to the spring body by a second connecting arm. The spring body may be oval-shaped in the rested state and circular in the biased state.

The first and second buttons may be positioned outside of the elongate opening of the first connector. The lock portion of the second connector may be an undercut, with the locking member configured to engage the undercut to lock the first connector to the second connector when the first and second connectors are in the activated position and the locking member is in the locked position. The lock portion may include a lead-in surface to automatically move the locking member from the locked position to the unlocked position when the first and second connectors are transitioned from the initial position to the activated position. The locking member may include ribs extending radially outward from the spring body. The locking member may include ramps extending radially inward from the spring body, with the ramps configured to automatically move the locking member from the locked position to the unlocked position when the first and second connectors are transitioned from the initial position to the activated position.

In a further aspect, a system for closed transfer of fluids includes a syringe adapter having a cannula, a proximal end, a distal end, and a wall defining an elongate opening between the proximal end and the distal end. The system also includes a vial access device including a lock portion, and a translating housing having a first seal membrane. The translating housing is movable within the elongate opening of the syringe adapter. The translating housing is transitionable between an initial position in which the syringe adapter is not in fluid communication with the vial access device and an activated position in which the syringe adapter is in fluid communication with the vial access device via the cannula. Further, the system includes a locking member engaged with the syringe adapter with the locking member transitionable between an unlocked position where the lock portion of the vial access device is movable within the elongate opening of the syringe adapter and a locked position where the locking member is configured to engage the lock portion of the vial access device to lock the syringe adapter to the vial access device in the activated position. The locking member comprises a spring body received by the elongate opening of the syringe adapter.

With the translating housing in the activated position, the cannula may pierce the first seal membrane of the translating housing. The vial access device may include a second seal membrane and with the translating housing in the activated position, the cannula pierces the first seal membrane of the translating housing and the second seal membrane of the vial access device. The vial access device may be attachable to a vial defining a vial chamber such that the vial chamber is in fluid communication with the vial access device. The vial access device may be attached to the vial and the translating housing in the activated position, where the syringe adapter is in fluid communication with the vial chamber via the cannula. The spring body is deformable between a rested state when the locking member is in the locked position and a biased state when the locking member is in the unlocked position, where the spring body is configured to return to the rested state. The syringe adapter may define a viewing window and with the translating housing in the initial position, a first indicator is displayed in the viewing window. With the translating housing in the activated position, a second indicator may be displayed in the viewing window, where the second indicator is different than the first indicator.

BRIEF DESCRIPTION OF THE DRAWINGS

The above-mentioned and other features and advantages of this disclosure, and the manner of attaining them, will become more apparent and the disclosure itself will be better understood by reference to the following descriptions of aspects of the disclosure taken in conjunction with the accompanying drawings, wherein:

FIG. 30 is a side elevation view of a connection housing in accordance with an aspect of the present invention.

FIG. 31 is a cross-sectional view of a connection housing taken along line 31-31 of FIG. 30 in accordance with an aspect of the present invention.

FIG. 53 is an exploded, perspective view of a connector in accordance with an aspect of the present invention.

FIG. 54 is an assembled, perspective view of the connector of FIG. 53 in accordance with an aspect of the present invention.

Corresponding reference characters indicate corresponding parts throughout the several views. The exemplifications set out herein illustrate exemplary aspects of the disclosure, and such exemplifications are not to be construed as limiting the scope of the disclosure in any manner.

DETAILED DESCRIPTION

Figure 1:
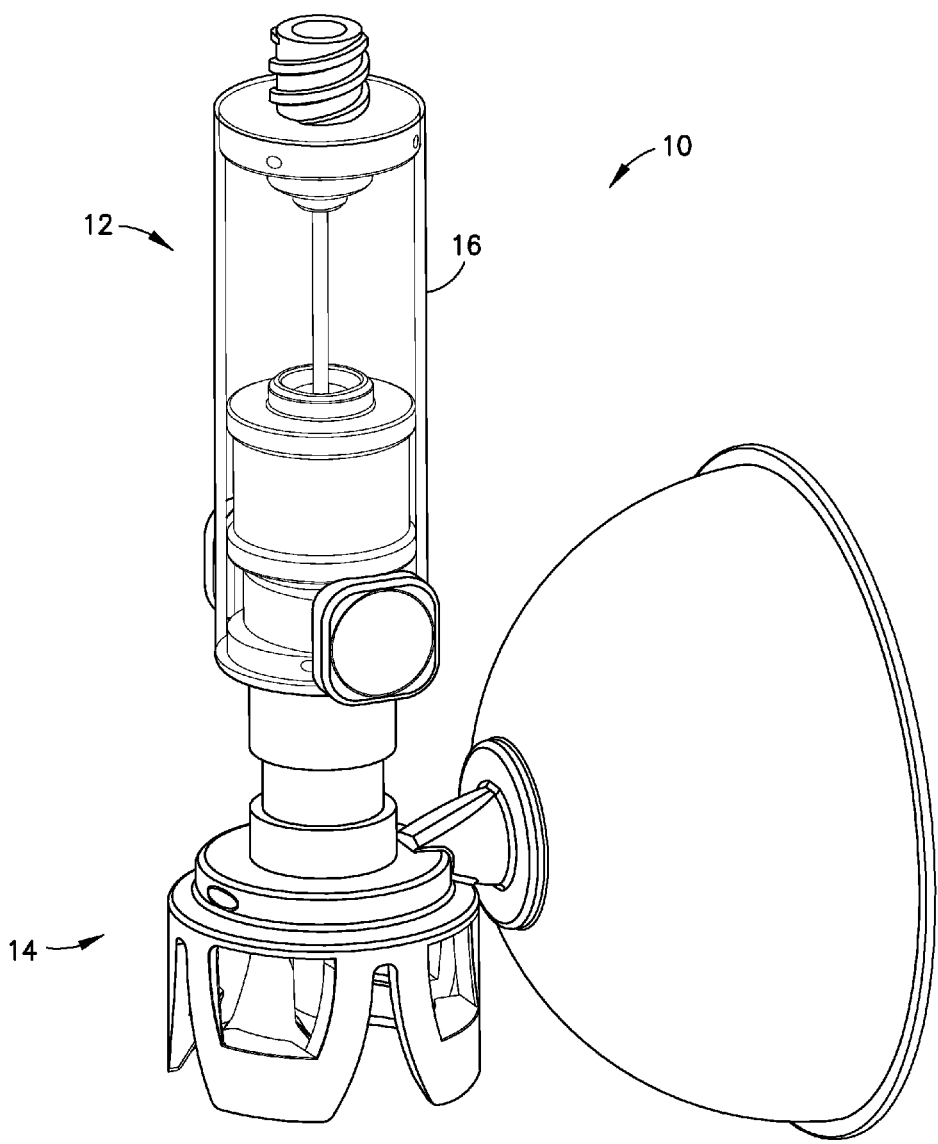
FIG. 1 is a perspective view of a system in accordance with an aspect of the present invention.

The following description is provided to enable those skilled in the art to make and use the described aspects contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary aspects of the invention. Hence, specific dimensions and other physical characteristics related to the aspects disclosed herein are not to be considered as limiting.

In the following discussion, "distal" refers to a direction generally toward an end of a system adapted for contact with a container, such as a vial, and "proximal" refers to the opposite direction of distal, i.e., away from the end of a system adapted for contact with the container. For purposes of this disclosure, the above-mentioned references are used in the description of the components of a system in accordance with the present disclosure.

FIG. 1 illustrates an exemplary aspect of the present disclosure. Referring to FIG. 1, a system for the closed transfer of fluids 10 includes a syringe adapter 12, a vial access device 14, and a syringe adapter housing 16. The system 10 provides substantially leak-proof sealing during engagement of a cannula with a vial, during transfer of a substance from a vial chamber to a barrel chamber via the cannula, and during disengagement of the cannula from the vial. The leak-proof sealing of the system 10 substantially prevents leakage of both air and liquid during use of the system 10. The system 10 is compatible with a needle and syringe assembly for accessing a medication contained within a vial for administering the medication to a patient. The system 10 is also compatible to be used with IV bags, IV lines, patient connectors, or other aspects to move fluids between first and second components. Although the exemplary aspect of FIG. 1 illustrates a syringe adapter 12 and a vial access device 14, a system of the present disclosure could be utilized with any two components to move fluids therebetween. Furthermore, the connection mechanisms of the present disclosure can be reversed. For example, in one aspect, the lock portion, e.g., the undercut, can be included on the syringe adapter 12 and the push button spring may be included on the vial access device 14. In one aspect, the lock portion, e.g., the undercut, can be included on the vial access device 14 and the push button spring may be included on the syringe adapter 12.

FIGS. 2-23 and 26-44 illustrate another exemplary aspect of the present disclosure. Referring to FIGS. 2-23 and 26-44, a system for the closed transfer of fluids 20 includes a syringe adapter 22, a vial access device 24, and a syringe adapter housing 26 having a viewing window 28. The system 20 provides substantially leak-proof sealing during engagement of a cannula with a vial, during transfer of a substance from a vial chamber to a barrel chamber via the cannula, and during disengagement of the cannula from the vial. The leak-proof sealing of the system 20 substantially prevents leakage of both air and liquid during use of the system 20. The system 20 is compatible with a needle and syringe assembly for accessing a medication contained within a vial for administering the medication to a patient. The system 20 is also compatible to be used with IV bags, IV lines, patient connectors, or other aspects to move fluids between a first and second component. Although the exemplary aspect of FIGS. 2-23 and 26-44 illustrate a syringe adapter 22 and a vial access device 24, a system of the present disclosure could be utilized with any two components to move fluids therebetween. Furthermore, the connection mechanisms of the present disclosure can be reversed. For example, in one aspect, the lock portion, e.g., the undercut, can be included on the syringe adapter 22 and the push button spring may be included on the vial access device 24. In one aspect, the lock portion, e.g., the undercut, can be included on the vial access device 24 and the push button spring may be included on the syringe adapter 22.

Figure 24:
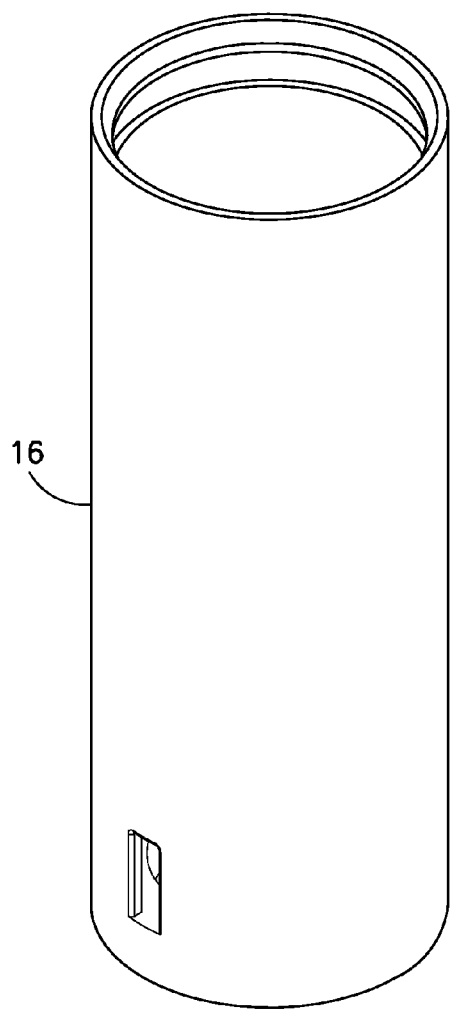
FIG. 24 is a perspective view of a syringe adapter housing in accordance with another aspect of the present invention.
Figure 25:
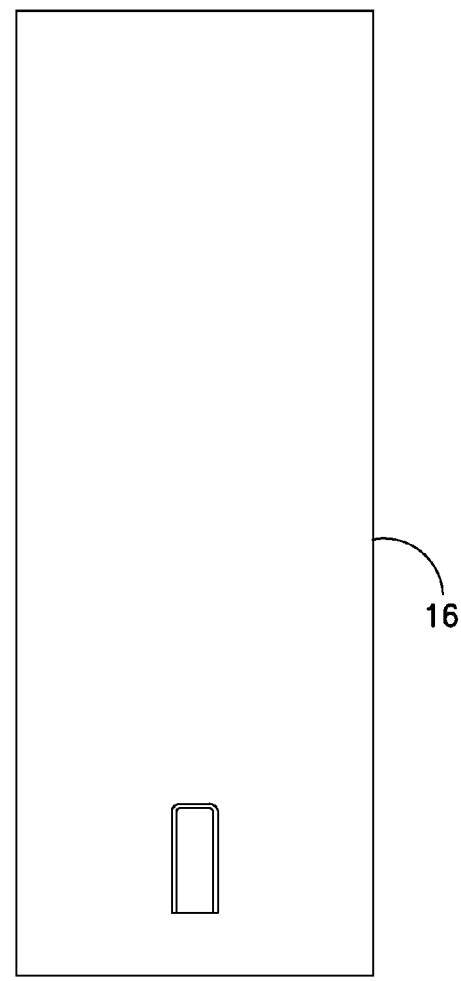
FIG. 25 is a side elevation view of a syringe adapter housing in accordance with another aspect of the present invention.

The exemplary aspect illustrated in FIG. 1 includes similar components to the aspect illustrated in FIGS. 2-23 and 26-44. For the sake of brevity, these similar components and the similar steps of using the system 10 will not all be discussed in conjunction with the aspect illustrated in FIG. 1. In one aspect, the syringe adapter housing 16 of the system 10 does not include a viewing window as shown in FIGS. 24 and 25.

Figure 2:
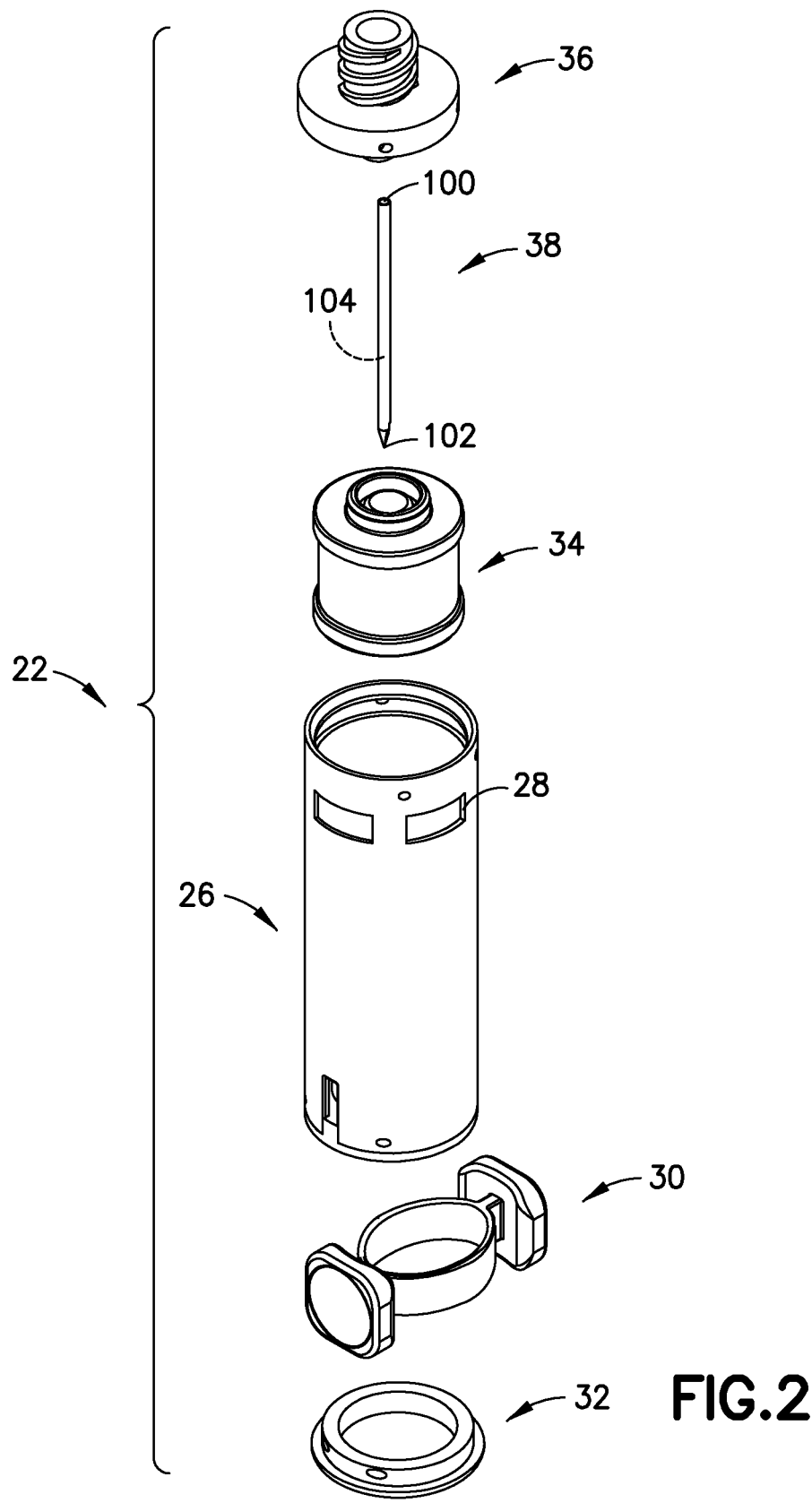
FIG. 2 is an exploded, perspective view of a syringe adapter in accordance with an aspect of the present invention.
Figure 3:
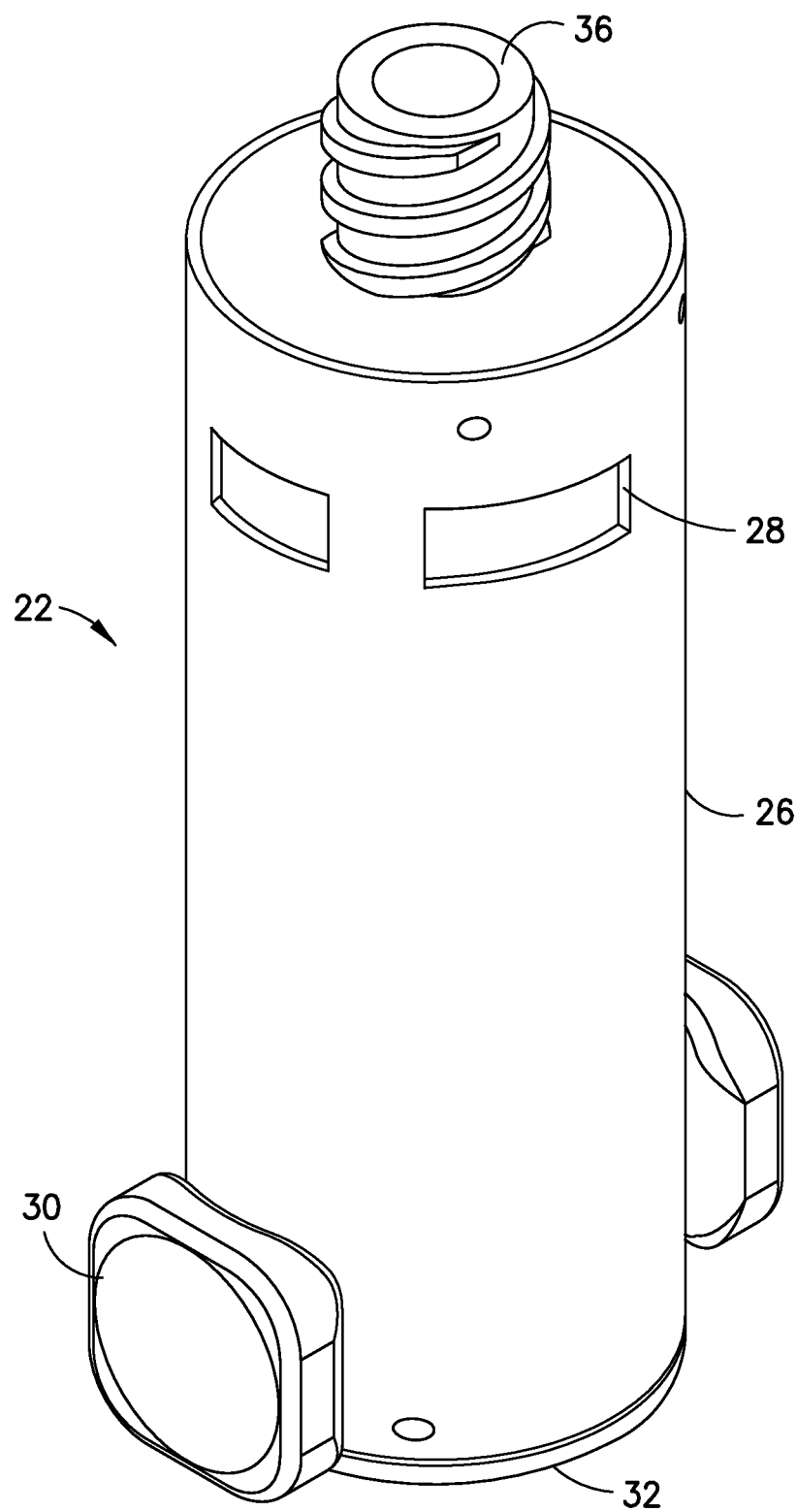
FIG. 3 is an assembled, perspective view of the syringe adapter of FIG. 2 in accordance with an aspect of the present invention.
Figure 4:
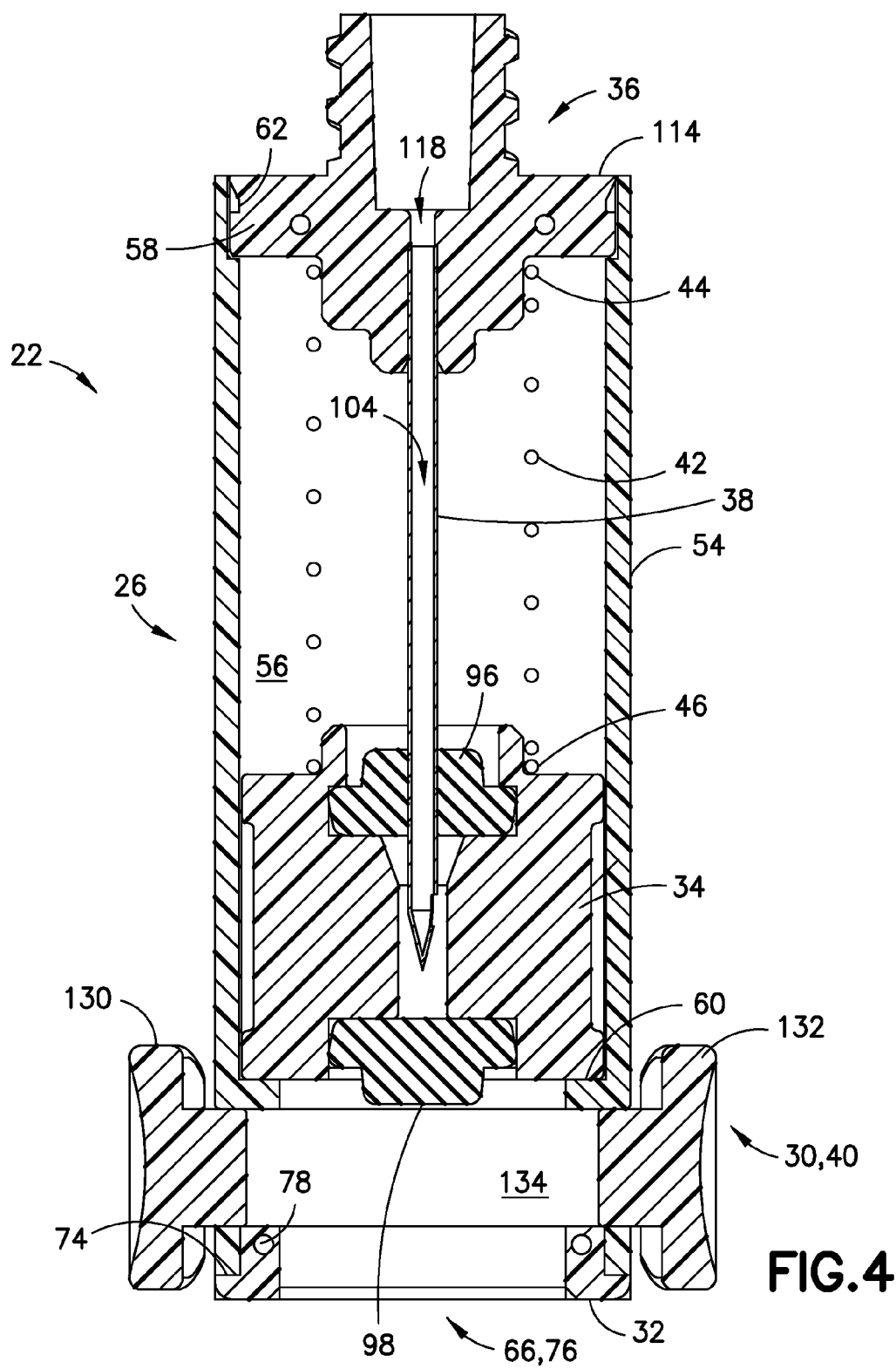
FIG. 4 is a cross-sectional view of the syringe adapter of FIG. 3 in accordance with an aspect of the present invention.

Referring to FIGS. 2-4, syringe adapter 22 generally includes a syringe adapter housing 26 having a viewing window 28, a locking member 30, a bottom housing 32, a translating housing 34, a needle hub 36, a cannula 38, and a spring 42 as described in more detail below.

Referring to FIGS. 2-5, syringe adapter housing 26 generally includes viewing window 28, first or proximal end 50, second or distal end 52, sidewall 54 defining elongate opening 56 between first end 50 and second end 52, first shoulder 58, second shoulder 60, needle hub protrusion 62, locking member receiving cavity 64, and vial access device receiving area 66.

Figure 5:
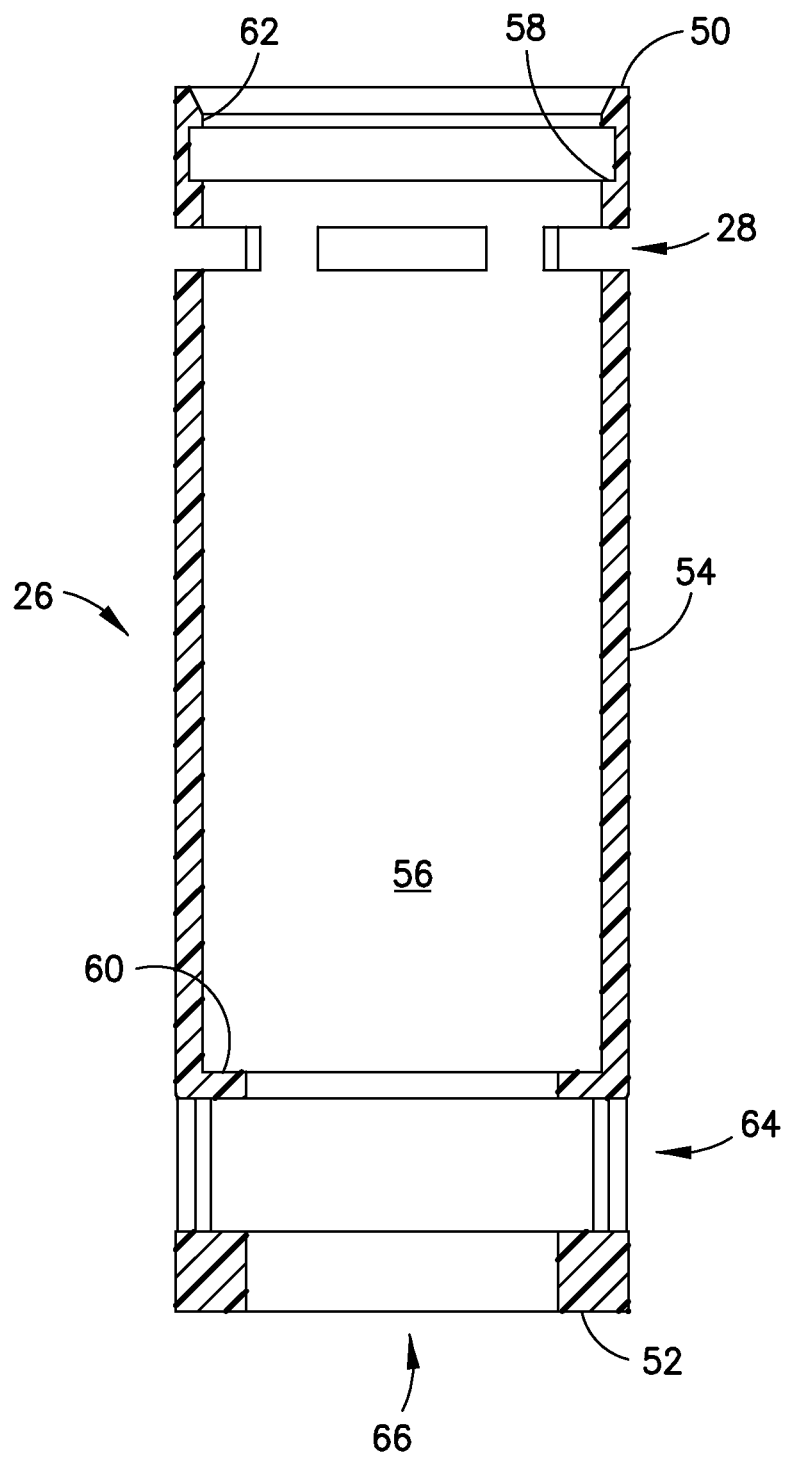
FIG. 5 is a cross-sectional view of a syringe adapter housing of FIG. 2 in accordance with an aspect of the present invention.

Referring to FIG. 5, elongate opening 56 is sized and shaped to receive translating housing 34 as described in more detail below. First shoulder 58 is disposed adjacent first end 50 and is configured to provide an engagement surface with needle hub 36 as shown in FIG. 4. Second shoulder 60 is disposed adjacent second end 52 and is configured to provide an engagement surface with translating housing 34 as shown in FIG. 4. Needle hub protrusion 62 extends inward from sidewall 54 at first end 50 and is configured to provide an engagement portion for securing needle hub 36 to syringe adapter housing 26. In other aspects, the engagement portion between syringe adapter housing 26 and needle hub 36 may include a threaded portion, snap fit mechanism, a ball detent, locking tabs, spring loaded locking mechanism, latch, adhesive, or other similar mechanism. Referring to FIG. 5, locking member receiving cavity 64 is located adjacent second end 52 and is sized and shaped to receive locking member 30 as shown in FIG. 4. Referring to FIG. 5, vial access device receiving area 66 is located at second end 52 and is sized and shaped to receive vial access device 24 as shown in FIGS. 33-44.

Figure 90:
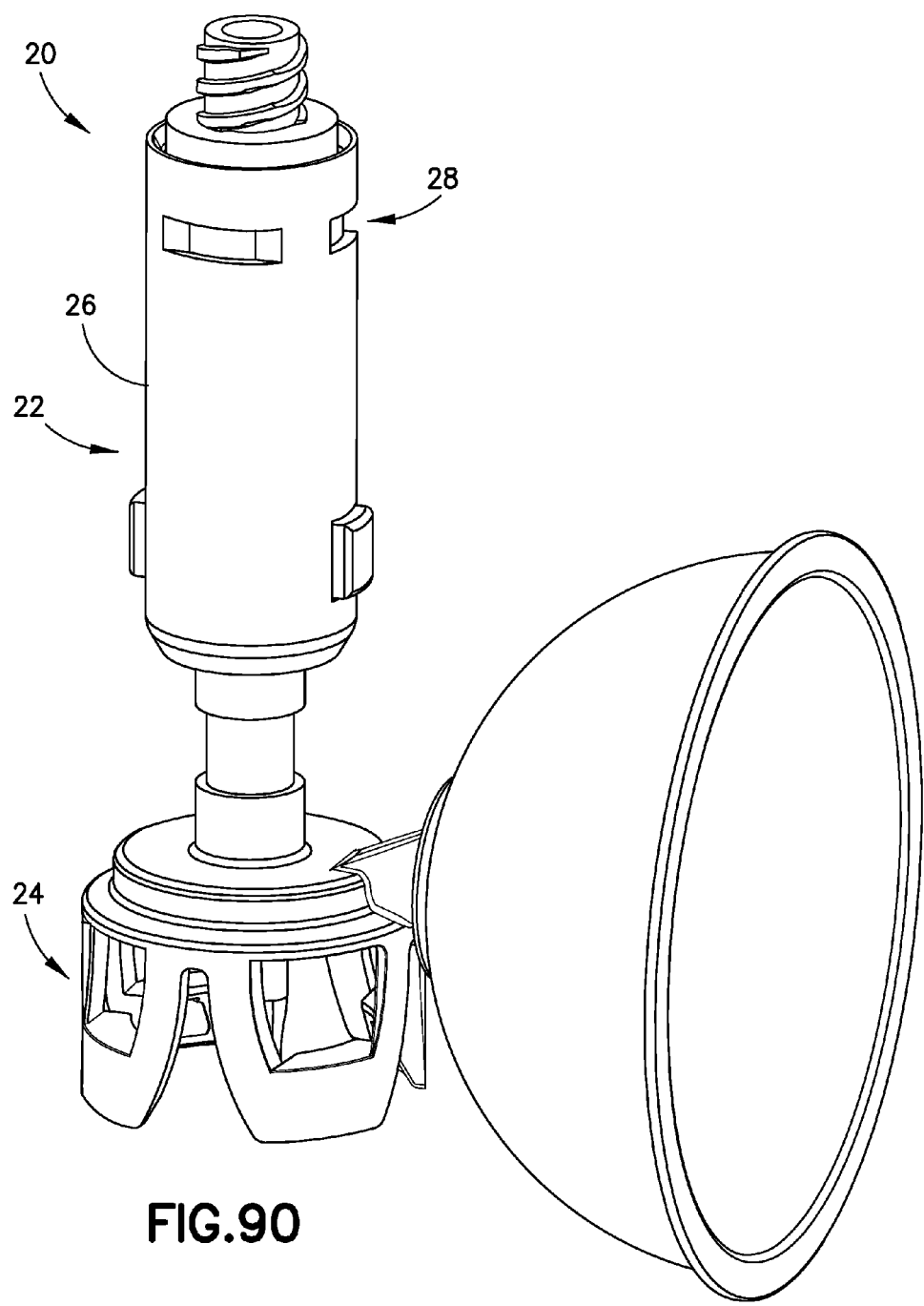
FIG. 90 is an assembled, perspective view of a syringe adapter and a vial access device in an initial position in accordance with another aspect of the present invention.
Figure 91:
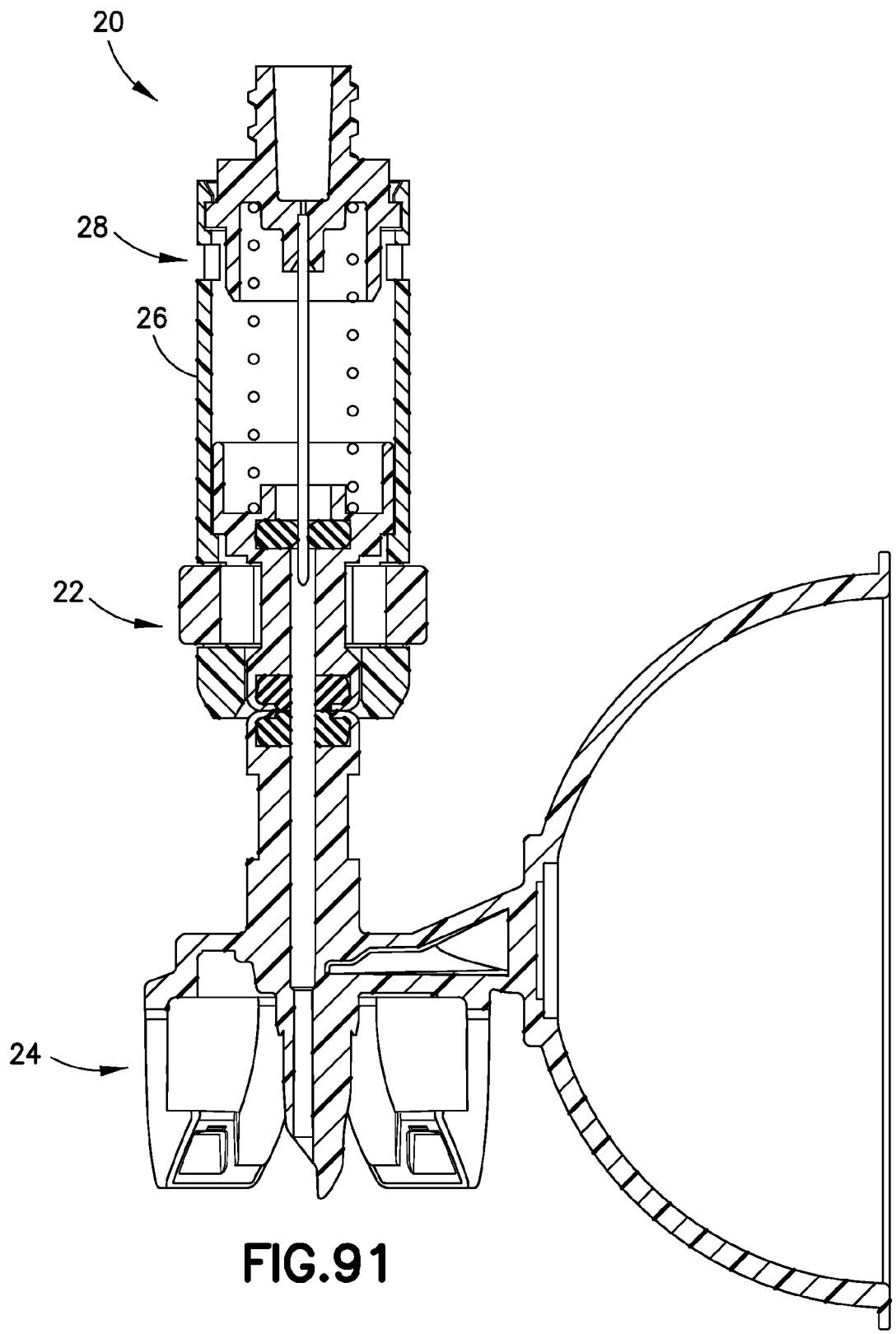
FIG. 91 is a cross-sectional view of the syringe adapter and vial access device of FIG. 90 in an initial position in accordance with another aspect of the present invention.
Figure 92:
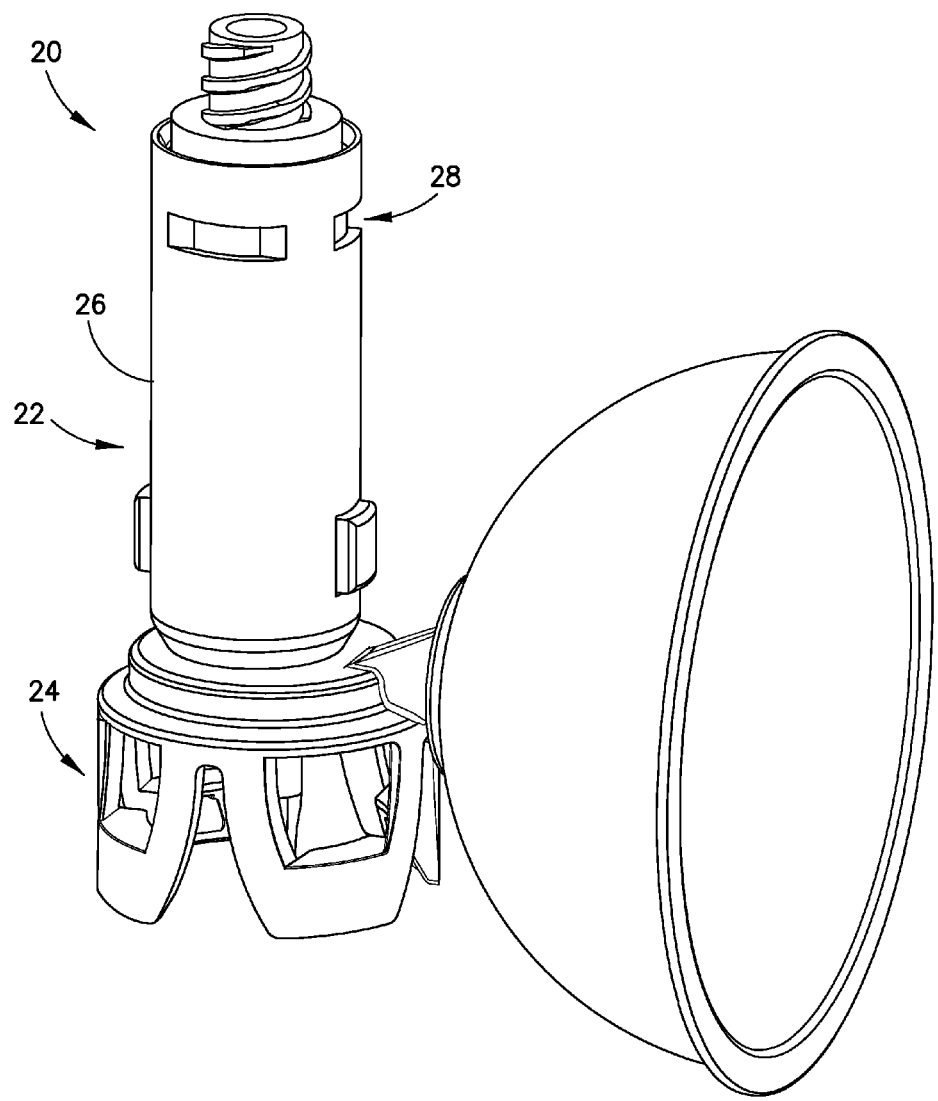
FIG. 92 is a perspective view of a syringe adapter and vial access device in an activated position in accordance with another aspect of the present invention.
Figure 93:
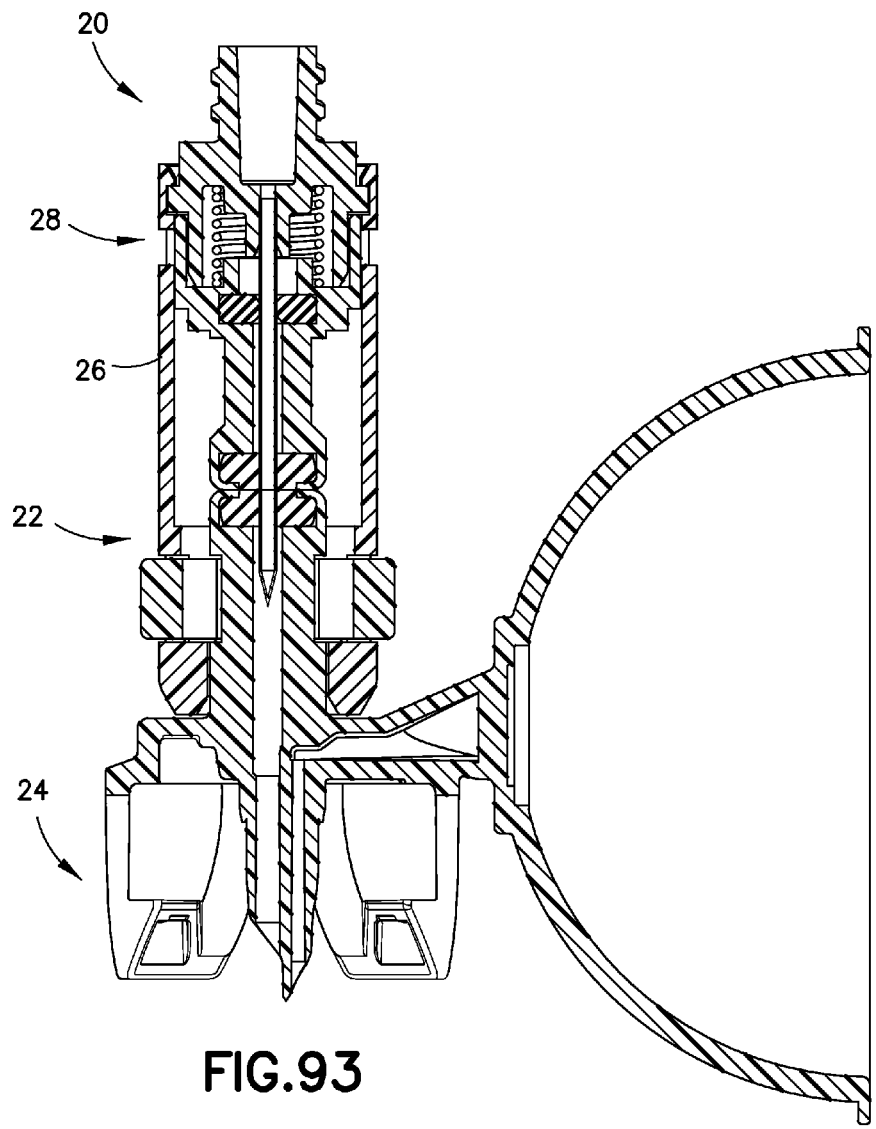
FIG. 93 is a cross-sectional view of the syringe adapter and vial access device of FIG. 92 in an activated position in accordance with another aspect of the present invention.

In one aspect, syringe adapter housing 26 includes viewing window 28. Viewing window 28 provides a window to display an indication means of a position of system 20. For example, referring to FIGS. 90 and 91, in one aspect, with system 20 in an initial position, a first indicator, such as a first color, could be displayed to a user via viewing window 28. Referring to FIGS. 92 and 93, with system 20 in an activated position, a second indicator, such as a second color, could be displayed to a user via viewing window 28. In this manner, feedback which indicates the position of system 20 is provided to a user. In one aspect, concentric rings that cover one another and change from a red color to a green color may be utilized with viewing window 28 to indicate a position of system 20. In one aspect, concentric rings that cover one another and include images or words may be utilized with viewing window 28 to indicate a position of system 20. In other aspects, concentric rings that include alignment markings and/or covering rings may be utilized with viewing window 28 to indicate a position of system 20. In one aspect, a spring loaded washer mechanism may be utilized with viewing window 28 to indicate a position of system 20 by biasing the spring loaded washer mechanism when the system is activated and changing an indicator, such as a color, that is visible through the viewing window 28.

Figure 6:
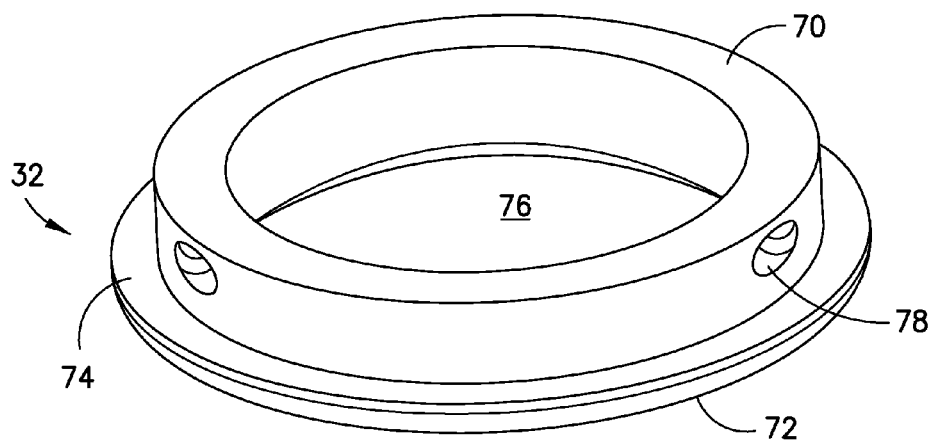
FIG. 6 is a perspective view of a bottom housing in accordance with an aspect of the present invention.
Figure 7:
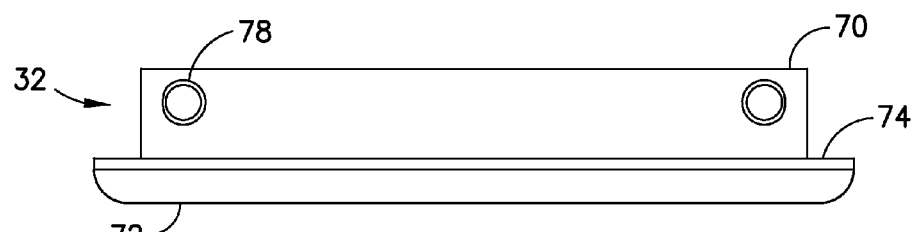
FIG. 7 is a side elevation view of a bottom housing in accordance with an aspect of the present invention.
Figure 8:
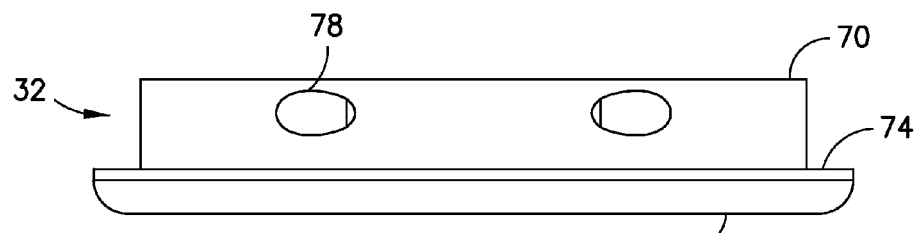
FIG. 8 is another side elevation view of a bottom housing in accordance with an aspect of the present invention.

Referring to FIGS. 6-8, bottom housing 32 generally includes first or proximal end 70, second or distal end 72, flange portion 74, vial access device aperture 76, and openings 78.

Flange portion 74 is disposed adjacent second end 72 and is configured to provide an engagement surface with syringe adapter housing 26 as shown in FIG. 4. Openings 78 are disposed adjacent flange portion 74 and may be utilized for securing bottom housing 32 to syringe adapter housing 26. In other aspects, the engagement portion between syringe adapter housing 26 and bottom housing 32 may include a threaded portion, snap fit mechanism, a ball detent, locking tabs, spring loaded locking mechanism, latch, adhesive, ultrasonic welding, spin welding, press fit, or other similar mechanism.

In one aspect, syringe adapter housing 26 and bottom housing 32 may form a single integral component. In another aspect, syringe adapter housing 26 and bottom housing 32 are separate components and bottom housing 32 is attachable to syringe adapter housing 26 such that significant relative movement between syringe adapter housing 26 and bottom housing 32 is prevented.

Referring to FIGS. 9-12, translating housing 34 generally includes first or proximal end 90, second or distal end 92, fluid transfer channel 94 extending from first end 90 to second end 92, first seal membrane 96, and second seal membrane 98. The translating housing 34 is sized for movement within the elongate opening 56 of syringe adapter housing 26. The translating housing 34 is transitionable between an initial position (FIGS. 33-37) in which syringe adapter 22 is not in fluid communication with vial access device 24 and an activated position (FIGS. 38-44) in which syringe adapter 22 is in fluid communication with vial access device 24 via cannula 38. In one aspect, a translating housing of the present disclosure may include two seal membranes as shown in FIGS. 9-12. In other aspects, a translating housing of the present disclosure may include one seal membrane. In some aspects, a translating housing of the present disclosure may include more than two seal membranes.

Figure 9:
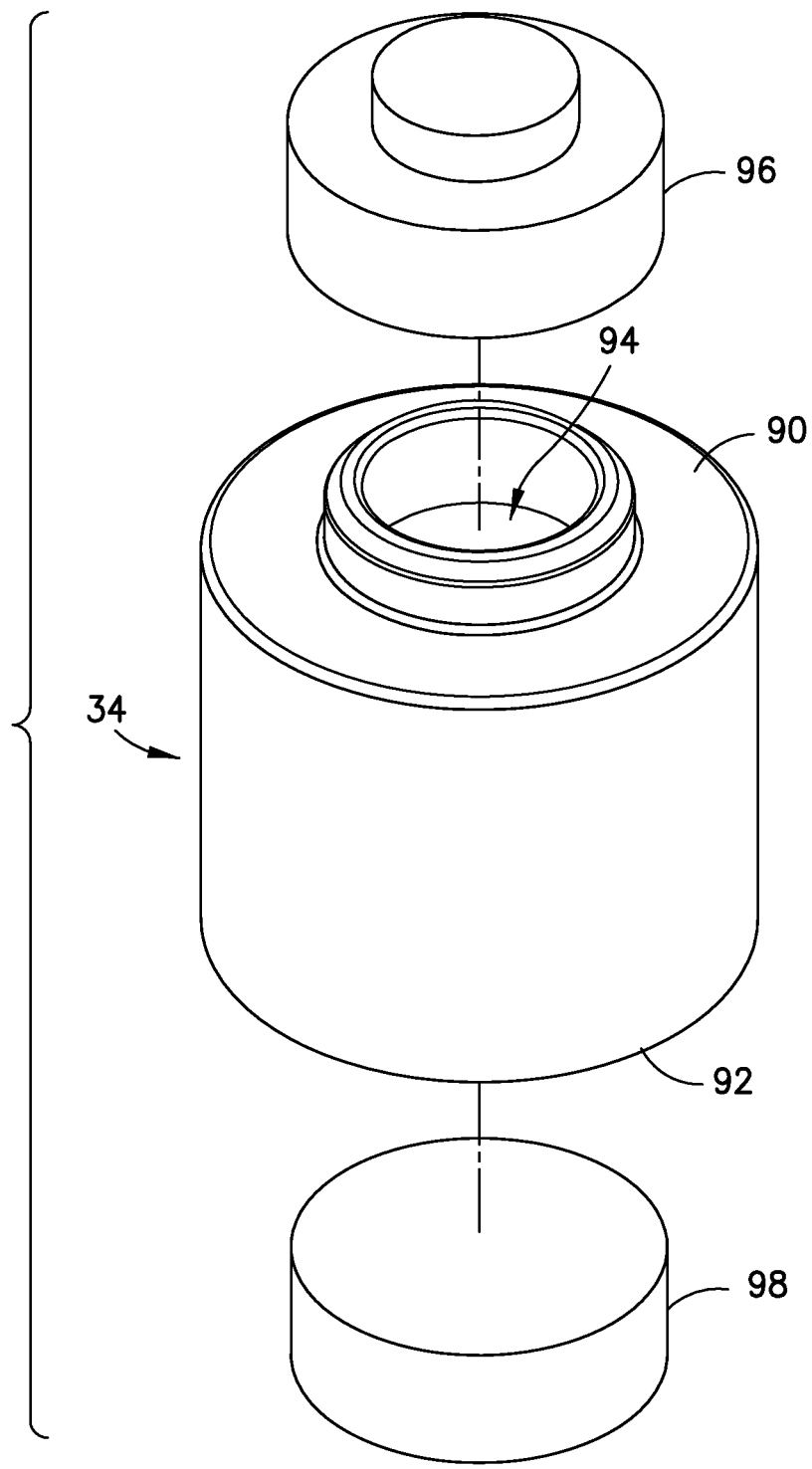
FIG. 9 is an exploded, perspective view of a translating housing in accordance with an aspect of the present invention.
Figure 10:
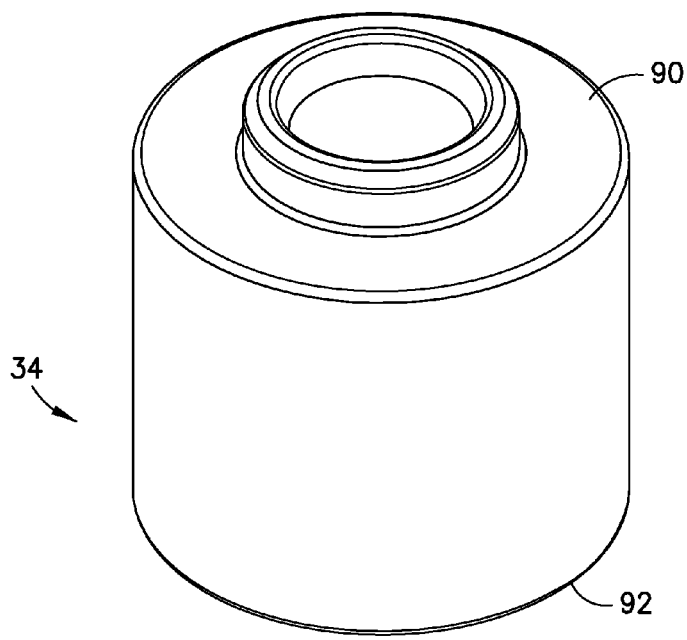
FIG. 10 is an assembled, perspective view of the translating housing of FIG. 9 in accordance with an aspect of the present invention.
Figure 11:
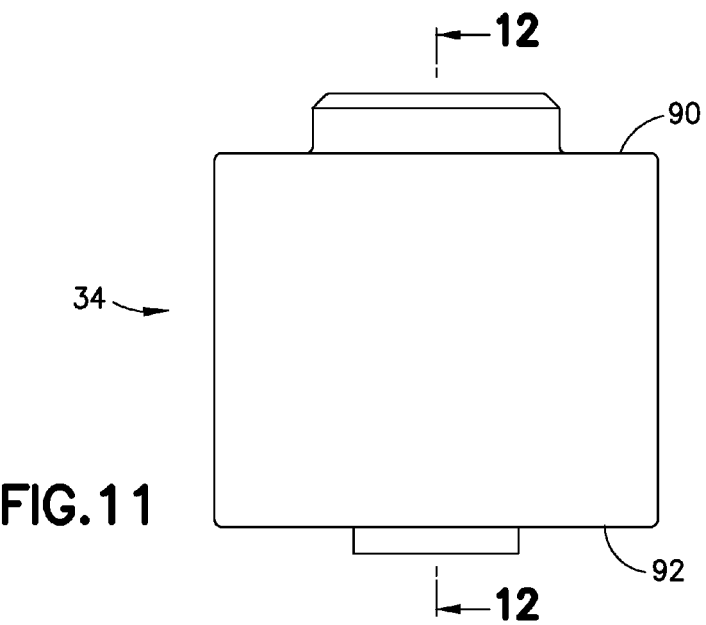
FIG. 11 is a side elevation view of a translating housing in accordance with an aspect of the present invention.
Figure 12:
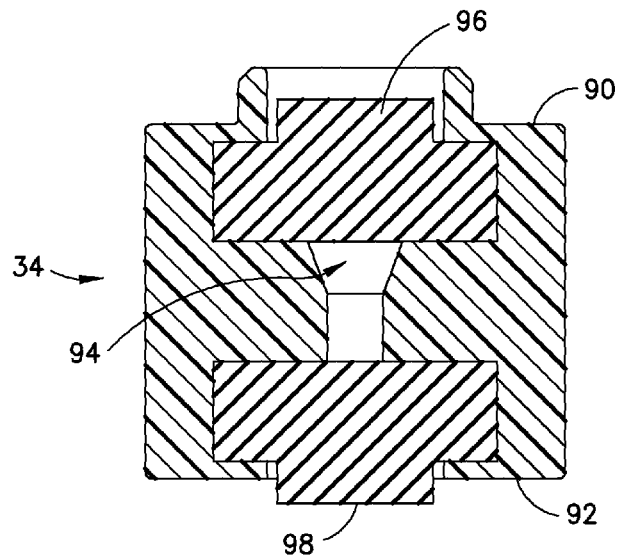
FIG. 12 is a cross-sectional view of a translating housing taken along line 12-12 of FIG. 11 in accordance with an aspect of the present invention.

Referring to FIGS. 9 and 12, in one aspect, translating housing 34 may contain a first pierceable seal membrane 96. In one aspect, translating housing 34 may contain a second pierceable seal membrane 98. The pierceable seal membranes 96, 98 provide for a liquid and gas tight seal between syringe adapter 22 and vial access device 24 during fluid transfer to minimize leakage and thereby prevent exposure of hazardous medicaments to a user. The pierceable seal membranes 96, 98 provide a self-sealing seal that, with syringe adapter 22 and vial access device 24 attached to a vial, provides a leak-proof seal preventing any substance contained within the vial chamber from being exposed to a health care provider reconstituting, transporting, or administering a drug using system 20. In one aspect, the pierceable seal membranes 96, 98 comprise a resilient material. For example, the pierceable seal membranes 96, 98 are preferably a unitary device molded of any flexible, elastomeric material conventionally used for fabricating gas-proof closures. The pierceable seal membranes 96, 98 may be formed of a natural rubber material, polyurethane elastomers, butyl rubbers, or similar materials. It is contemplated that the pierceable seal membranes 96, 98 are formed of a material having a Shore A hardness of approximately 10 to 50. It is also envisioned that the pierceable seal membranes 96, 98 can have other material hardness values that would provide an appropriate self-sealing material to provide a leak-proof seal with a vial septum of a vial and a syringe adapter, thereby preventing any liquid or medication residue from being exposed to a health care provider reconstituting, transporting, or administering a drug using system 20.

Referring to FIG. 2, cannula 38 includes a first or proximal end 100, a second or distal end 102, and a lumen 104 extending therebetween. Distal end 102 is in fluid communication with proximal end 100 via lumen 104 of cannula 38. As shown in FIGS. 38-44, distal end 102 of cannula 38 is capable of piercing pierceable seal membranes 96, 98 of translating housing 34 to place syringe adapter 22 and vial access device 24 in fluid communication as will be described in more detail below. In one aspect, distal end 102 of cannula 38 defines a sharp point. It is envisioned that other drug delivery mechanisms may be utilized with a system of the present disclosure. For example, needleless technologies that utilize septa, springs, or compressible silicone or other materials could be applied. In one aspect, a cannula of the present disclosure may comprise a metal cannula or a plastic cannula and may comprise a variety of tip and/or spike geometries.

Figure 13:
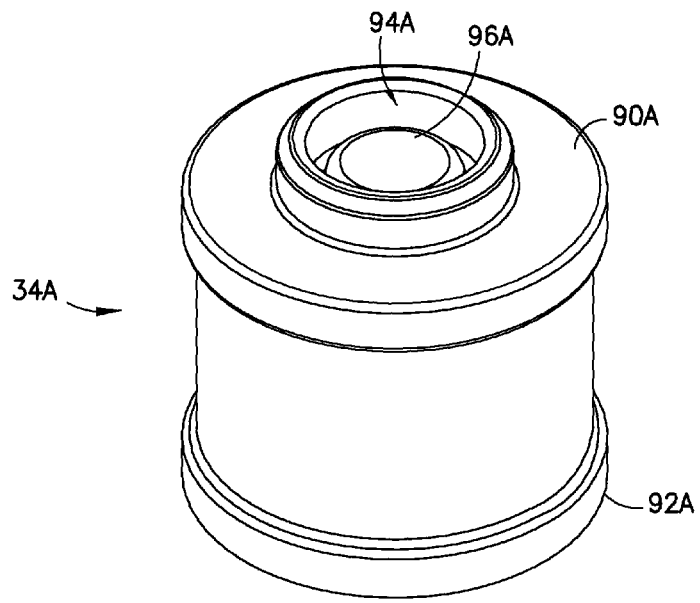
FIG. 13 is a perspective view of a translating housing in accordance with another aspect of the present invention.
Figure 14:
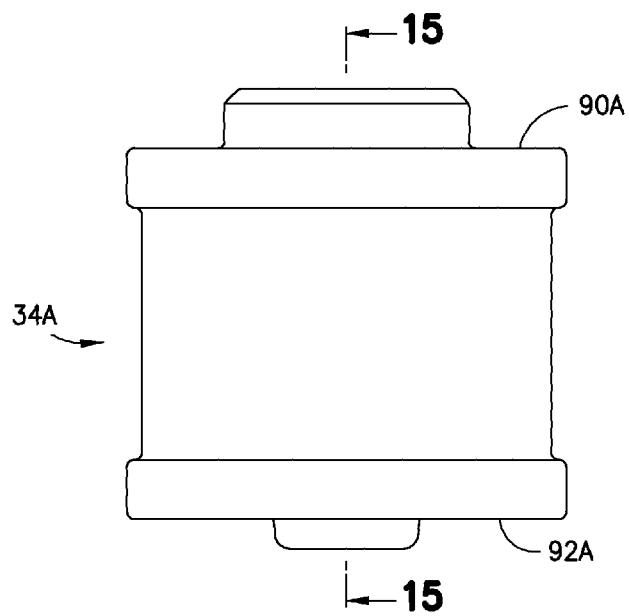
FIG. 14 is a side elevation view of a translating housing in accordance with another aspect of the present invention.
Figure 15:
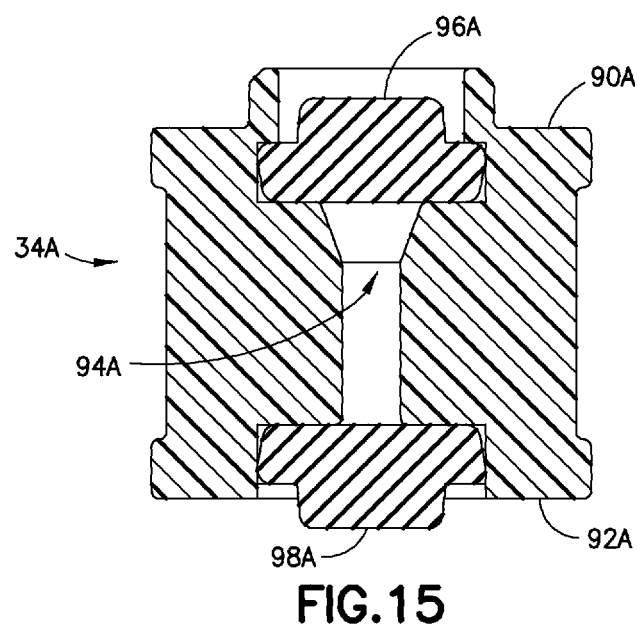
FIG. 15 is a cross-sectional view of a translating housing taken along line 15-15 of FIG. 14 in accordance with another aspect of the present invention.
Figure 16:
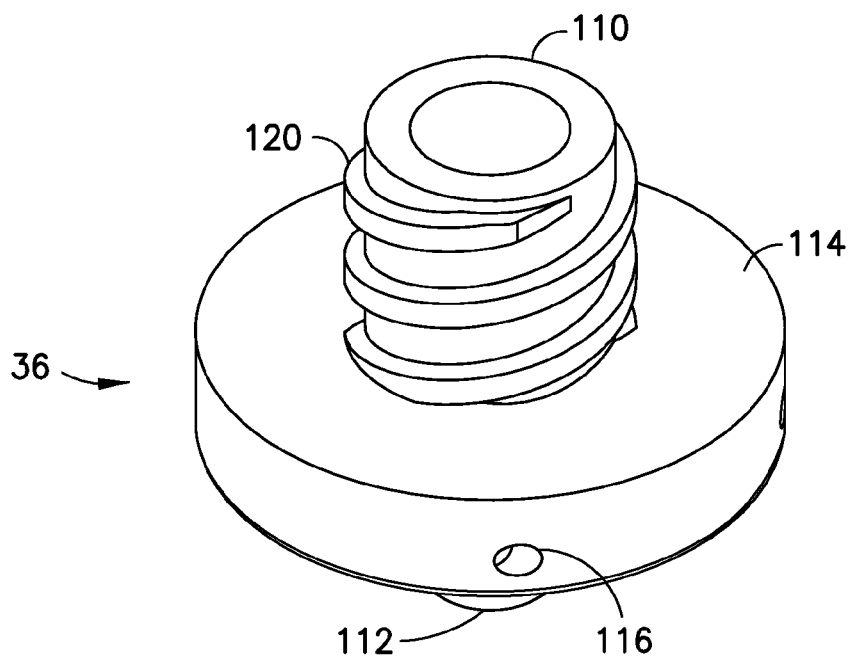
FIG. 16 is a perspective view of a needle hub in accordance with an aspect of the present invention.
Figure 17:
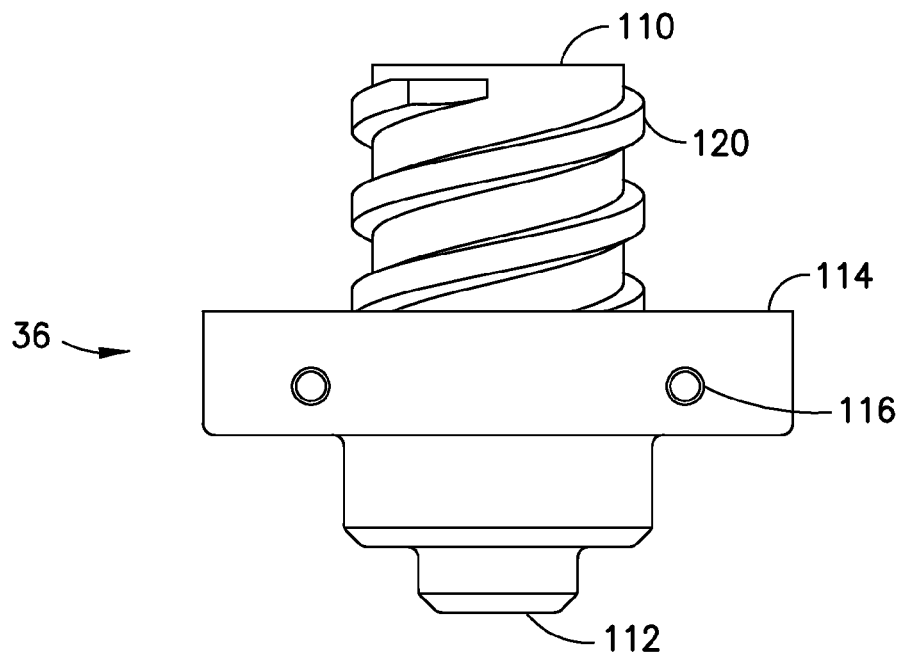
FIG. 17 is a side elevation view of a needle hub in accordance with an aspect of the present invention.
Figure 18:
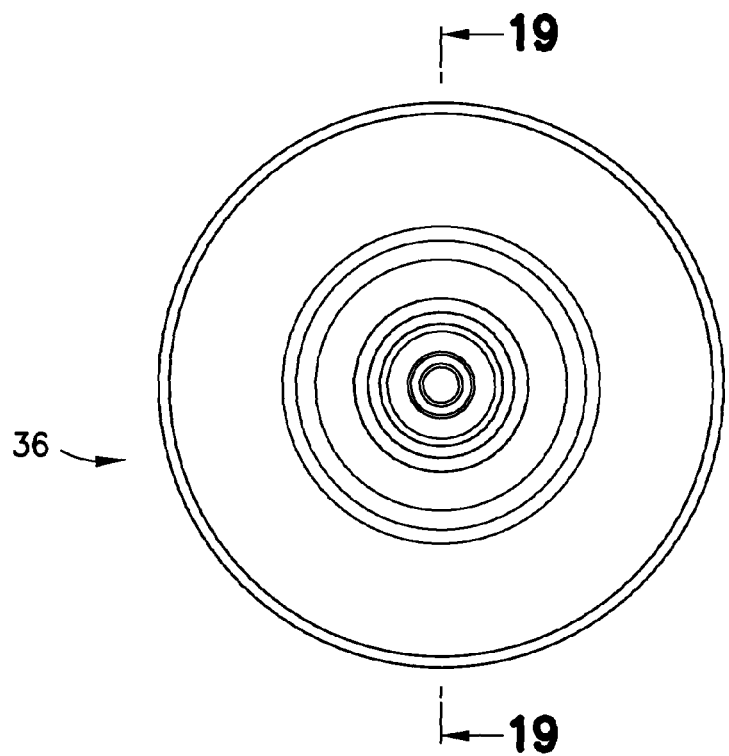
FIG. 18 is a top view of a needle hub in accordance with an aspect of the present invention.
Figure 19:
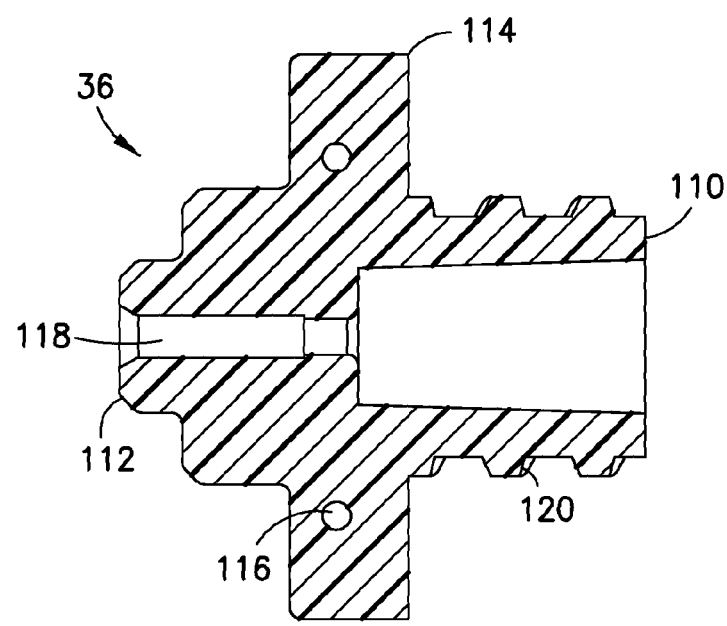
FIG. 19 is a cross-sectional view of a needle hub taken along line 19-19 of FIG. 18 in accordance with an aspect of the present invention.

FIGS. 13-15 illustrate another exemplary aspect of a translating housing of the present disclosure. The aspect illustrated in FIGS. 13-15 includes similar components to the aspect illustrated in FIGS. 9-12, and the similar components are denoted by a reference number followed by the letter A. For the sake of brevity, these similar components and the similar steps of using translating housing 34A will not all be discussed in conjunction with the aspect illustrated in FIGS. 13-15.

Referring to FIGS. 16-19, needle hub 36 generally includes first or proximal end 110, second or distal end 112, flange portion 114, openings 116, cannula receiving cavity 118, and barrel connection portion 120.

Proximal end 110 of needle hub 36 includes a barrel connection portion 120. In one aspect, barrel connection portion 120 is a female luer connector that is configured to mate with a male luer connector, although other suitable connectors may be utilized. The barrel connection portion 120 includes a projection that is configured to be received by a corresponding threaded portion of the male luer connector. Other arrangements for the barrel connection portion 120 may be utilized that deter undesired disconnection from the needle hub 36. Referring to FIG. 4, cannula receiving cavity 118 of needle hub 36 supports and is secured to a portion of cannula 38. In one aspect, the needle hub 36 is secured to the cannula 38 via an adhesive, such as an epoxy, although other suitable arrangements for securing the cannula 38 to the needle hub 36 may be utilized such as a press fit. In one aspect, the bottom of flange portion 114 of needle hub 36 also provides a connection with proximal end 44 of spring 42 so that distal end 46 of spring 42 may be compressed relative to proximal end 44 of spring 42. With spring 42 compressed, spring 42 exerts a biasing force that promotes translating housing 34 to move from the activated position (FIGS. 38-44) to the initial position (FIGS. 33-37) as described in more detail below.

In one aspect, openings 116 are disposed on flange portion 114 and may be utilized for securing needle hub 36 to syringe adapter housing 26. In other aspects, the engagement portion between syringe adapter housing 26 and needle hub 36 may include a threaded portion, snap fit mechanism, a ball detent, locking tabs, spring loaded locking mechanism, a latch, adhesive, ultrasonic welding, spin welding, press fit, or other similar mechanism.

In one aspect, needle hub 36 and syringe adapter housing 26 may form a single integral component. In another aspect, needle hub 36 and syringe adapter housing 26 are separate components and needle hub 36 is attachable to syringe adapter housing 26 such that significant relative movement between syringe adapter housing 26 and needle hub 36 is prevented.

In one aspect, locking member 30 comprises a push button spring 40. Referring to FIGS. 20-23, in one aspect, push button spring 40 generally includes first push button 130, second push button 132, spring body 134, defining aperture 139, first connecting arm 136, and second connecting arm 138. First push button 130 is connected to spring body 134 via first connecting arm 136 and second push button 132 is connected to spring body 134 via second connecting arm 138. In one aspect, a push button spring of the present disclosure may comprise a plastic spring part. In one aspect, a push button spring of the present disclosure may comprise a plastic oval spring. In other aspects, a push button spring of the present disclosure may comprise other snap spring geometries. For example, FIGS. 73-89 illustrate a variety of alternative aspects of a push button spring of the present disclosure. However, it is envisioned that other snap spring geometries may be used for a push button spring of the present disclosure. In some aspects, a push button spring of the present disclosure may comprise a metal spring. In one aspect, a push button spring of the present disclosure may comprise a metal spring that could be made of wire, stamped, or machined. A push button spring of the present disclosure may include a variety of shapes and sizes. In one aspect, a push button spring of the present disclosure may comprise a hybrid spring. For example, a push button spring of the present disclosure may include portions that comprise a wire portion, a plastic portion, a steel portion, and/or an elastic portion. In one aspect, a push button spring of the present disclosure may include two push buttons as shown in FIGS. 20-23. In other aspects, a push button spring of the present disclosure may include one push button. In some aspects, a push button spring of the present disclosure may include more than two push buttons. In one aspect, buttons could be integrated into syringe adapter housing 26. In one aspect, buttons and syringe adapter housing 26 may form a single integral component.

In one aspect, with push button spring 40 connected to syringe adapter 22, the push button spring 40 is transitionable between an unlocked position in which syringe adapter 22 is movable relative to the vial access device 24 and the translating housing 34 is movable relative to syringe adapter 22 and a locked position (FIGS. 38-44) in which the push button spring 40 engages a lock portion 152 of the vial access device 24 to lock the syringe adapter 22 to the vial access device 24 with the translating housing 34 in the activated position (FIGS. 38-44) as discussed in more detail below. The spring body 134 may be annular and deformable between a rested state when the push button spring 40 is in the locked position and a biased state when the locking member is in the unlocked position. The spring body 134 is configured to stay at the rested state and deformation of the spring body 134 biases the spring body 134. The spring body 134 is configured to return to the rested state from the biased state after being deformed. The spring body 134 is received within the elongate opening 56 of the syringe adapter 22 and is configured to at least partially block the elongate opening 56 when the spring body is in the rested state and open to receive the lock portion 152 of the vial access device 24 when the spring body 134 is in the biased state. The spring body 134 may be oval-shaped in the rested state and about circular in the biased state.

In one aspect, the lock portion 152 of vial access device 24 comprises an undercut 160 and with the push button spring 40 in the locked position (FIGS. 38-44), the spring body 134 of push button spring 40 engages the undercut 160 to lock the syringe adapter 22 to the vial access device 24 with the translating housing 34 in the activated position (FIGS. 38-44) as described in more detail below. In one aspect, the connection mechanisms of the present disclosure can be reversed. For example, in one aspect, the lock portion, e.g., the undercut, can be included on the syringe adapter 22 and the push button spring may be included on the vial access device 24.

Figure 20:
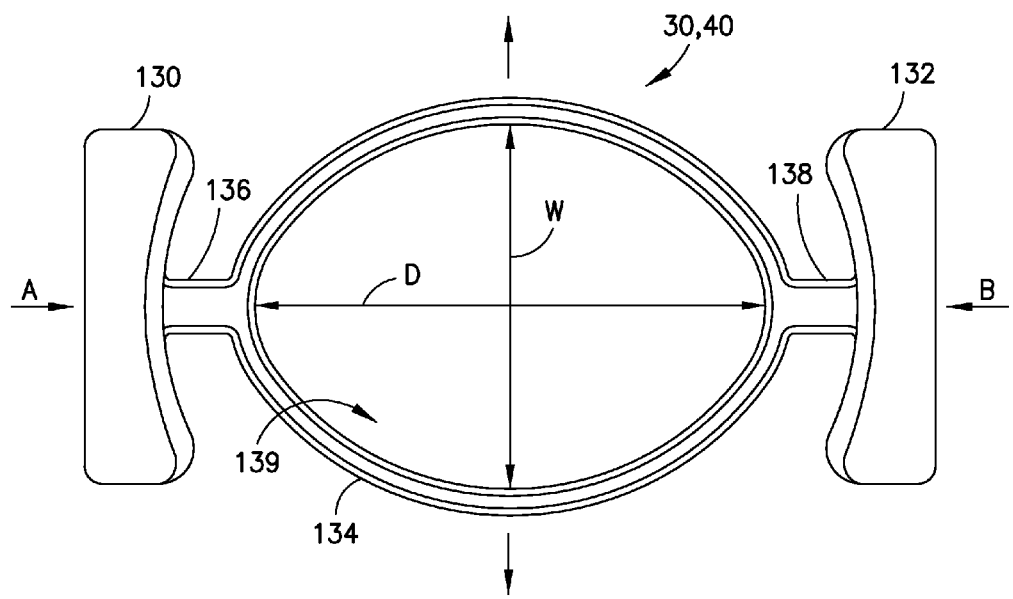
FIG. 20 is a top view of a push button spring in accordance with an aspect of the present invention.
Figure 21:
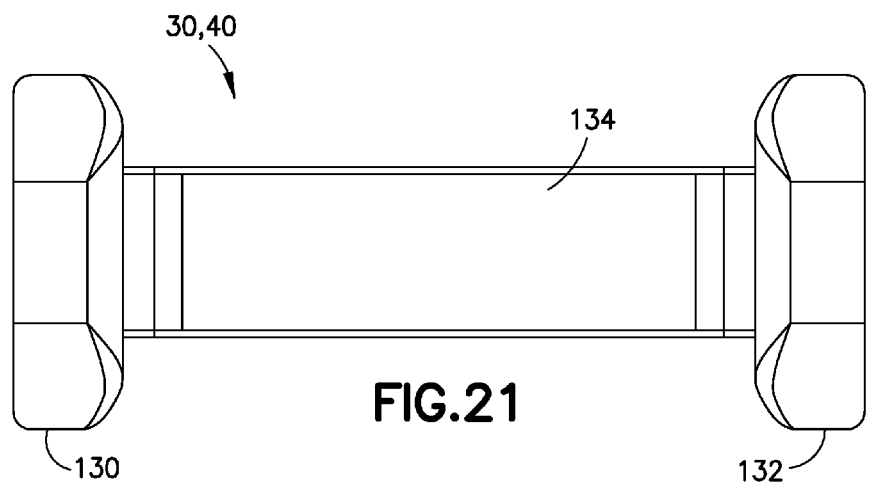
FIG. 21 is a side elevation view of a push button spring in accordance with an aspect of the present invention.
Figure 22:
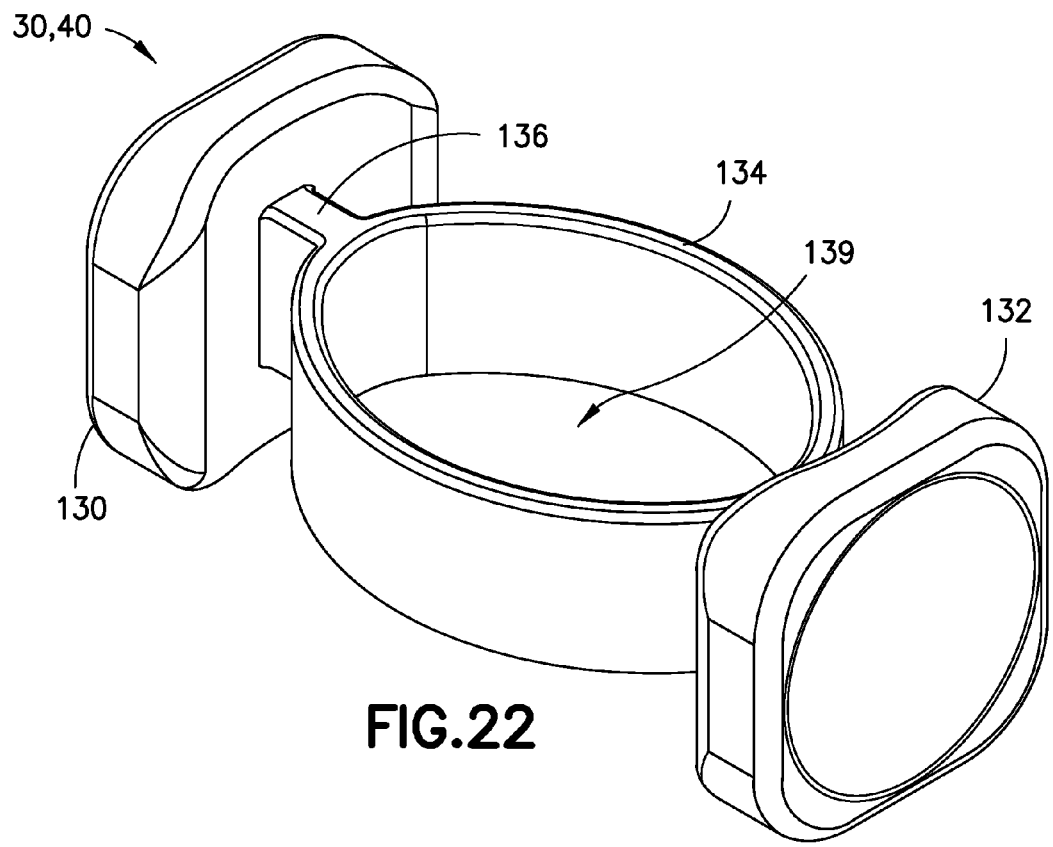
FIG. 22 is a perspective view of a push button spring in accordance with an aspect of the present invention.
Figure 23:
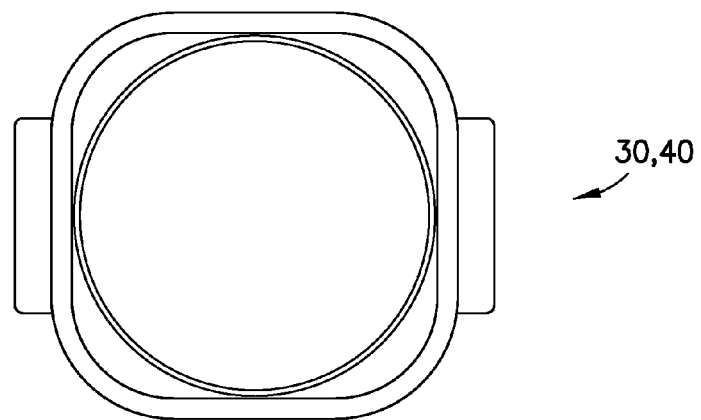
FIG. 23 is another side elevation view of a push button spring in accordance with an aspect of the present invention.

Referring to FIG. 20, in the locked position, first push button 130 and second push button 132 are not compressed and the distance D between first push button 130 and second push button 132 is at a maximum and the width W of spring body 134 is at a minimum. Push button spring 40 is in rested state in the locked position. In the locked position, push button spring 40 creates a small opening, i.e., the width W of spring body 134 is at a minimum, and acts as a stop or locking mechanism that prevents items from passing through aperture 139. In one aspect, in the locked position, push button spring 40 locks the syringe adapter 22 to the vial access device 24, i.e., push button spring 40 acts as a locking mechanism that prevents movement between syringe adapter 22 and vial access device 24.

To transition push button spring 40 from a locked position to an unlocked position, a force is applied to first push button 130 in a direction generally along arrow A (FIG. 20) and a force is applied to second push button 132 in a direction generally along arrow B (FIG. 20) to compress the push button spring 40. In this manner, compression of push button spring 40 causes the width W of spring body 134 to increase and the distance D between first push button 130 and second push button 132 to decrease. In this manner, aperture 139 of push button spring 40 is increased such that spring body 134 acts as a passageway that allows an object to translate through its path. For example, in the unlocked position, push button spring 40 allows movement between syringe adapter 22 and vial access device 24 as described in more detail below.

Referring to FIG. 4, spring 42 includes a first or proximal end 44 and a second or distal end 46. Spring 42 is disposed over cannula 38 within elongate opening 56 of syringe adapter housing 26 as shown in FIG. 4. In one aspect, with translating housing 34 in the initial position (FIGS. 33-37), the spring 42 is disposed within elongate opening 56 of syringe adapter housing 26 between proximal end 50 of syringe adapter housing 26 and first end 90 of translating housing 34. Referring to FIGS. 33-37, in one aspect, with translating housing 34 in the initial position, the locking member 30 may be held open by connection housing 150. Furthermore, with locking member 30 in the locked position (FIGS. 38-44) and translating housing 34 in the activated position (FIGS. 38-44), the spring 42 provides a biasing force on translating housing 34, and when locking member 30 is moved from the locked position to the unlocked position, the biasing force of the spring 42 promotes translating housing 34 to move from the activated position (FIGS. 38-44) to the initial position (FIGS. 33-37) as described in more detail below. In other aspects, a system of the present disclosure may utilize other devices that may store energy to provide a biasing force that promotes translating housing 34 to move from the activated position (FIGS. 38-44) to the initial position (FIGS. 33-37). For example, a built in plastic spring or an elastic material such as rubber, a thermoplastic elastomer, or silicone may be used. In some aspects, an elastic material could be placed in a grid format with multiple elastic strands. In other aspects, an elastic material could be placed in a single elastic strand.

Figure 26:
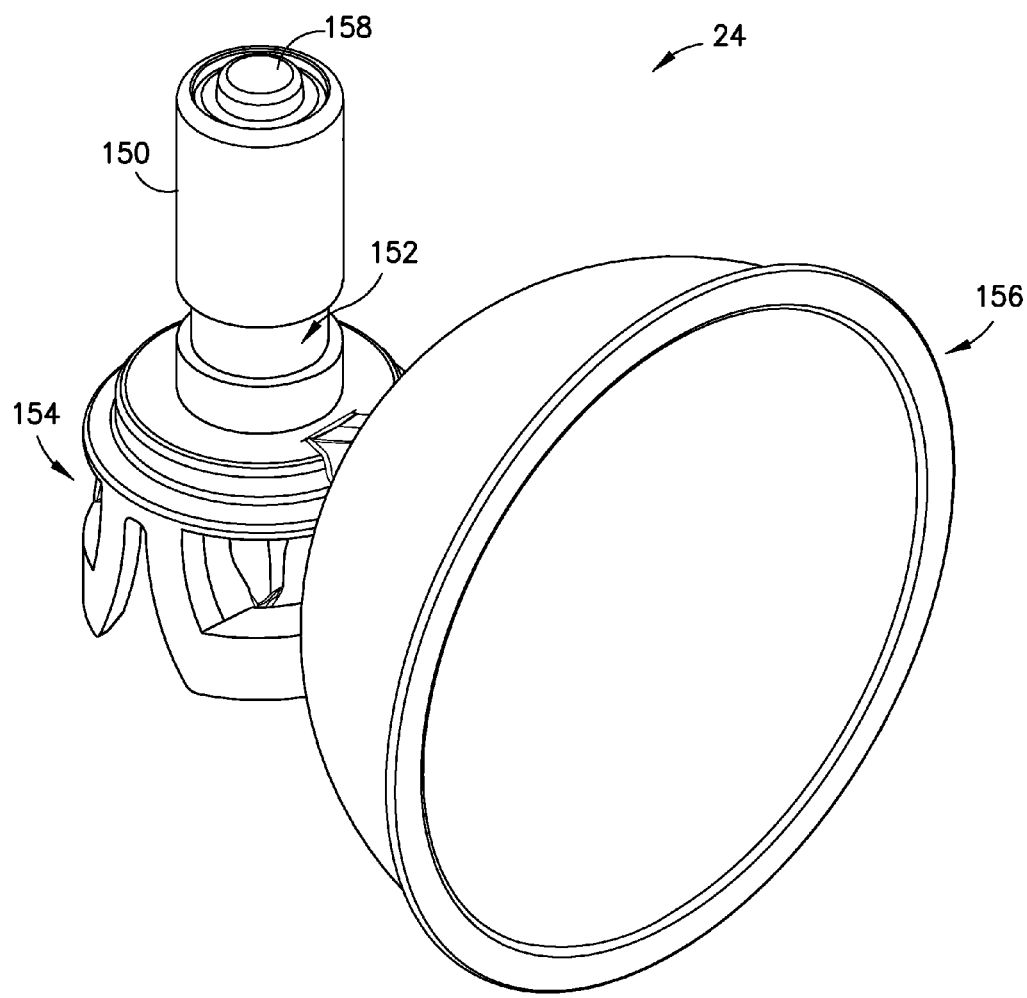
FIG. 26 is a perspective view of a vial access device in accordance with an aspect of the present invention.
Figure 27:
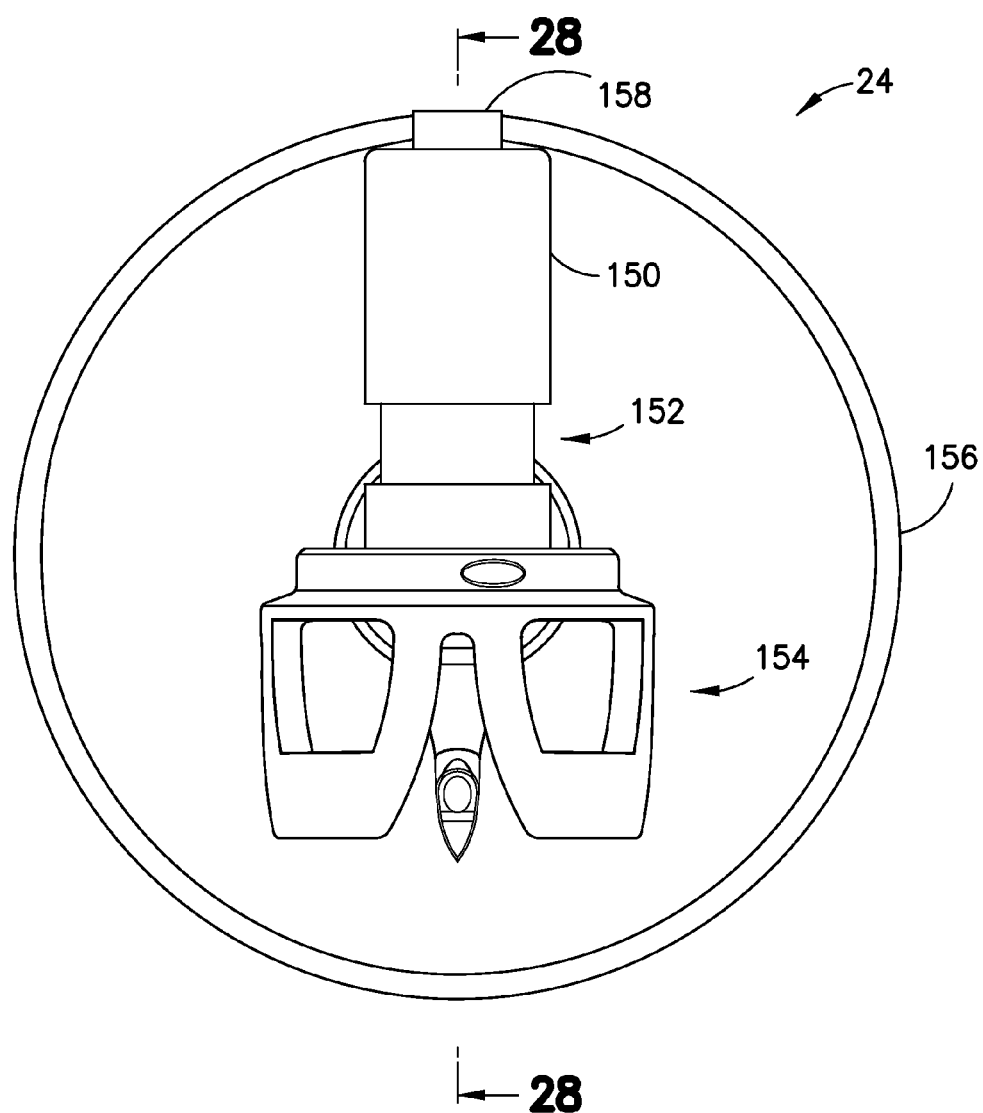
FIG. 27 is a side elevation view of a vial access device in accordance with an aspect of the present invention.
Figure 28:
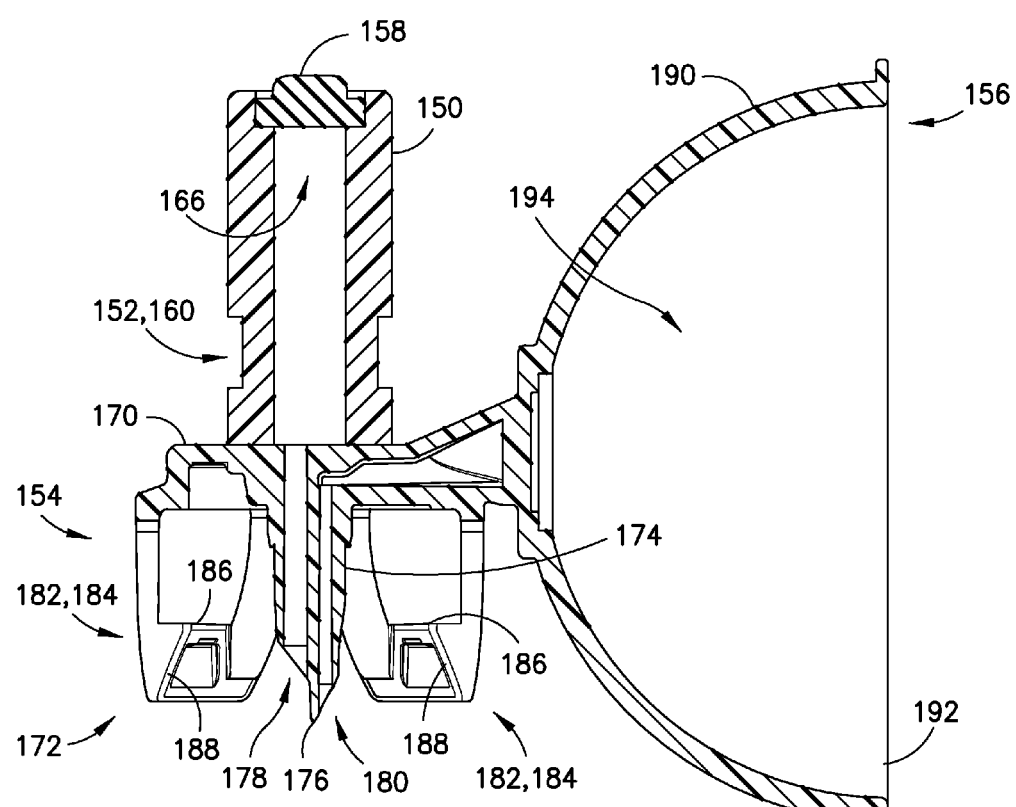
FIG. 28 is a cross-sectional view of a vial access device taken along line 28-28 of FIG. 27 in accordance with an aspect of the present invention.
Figure 29:
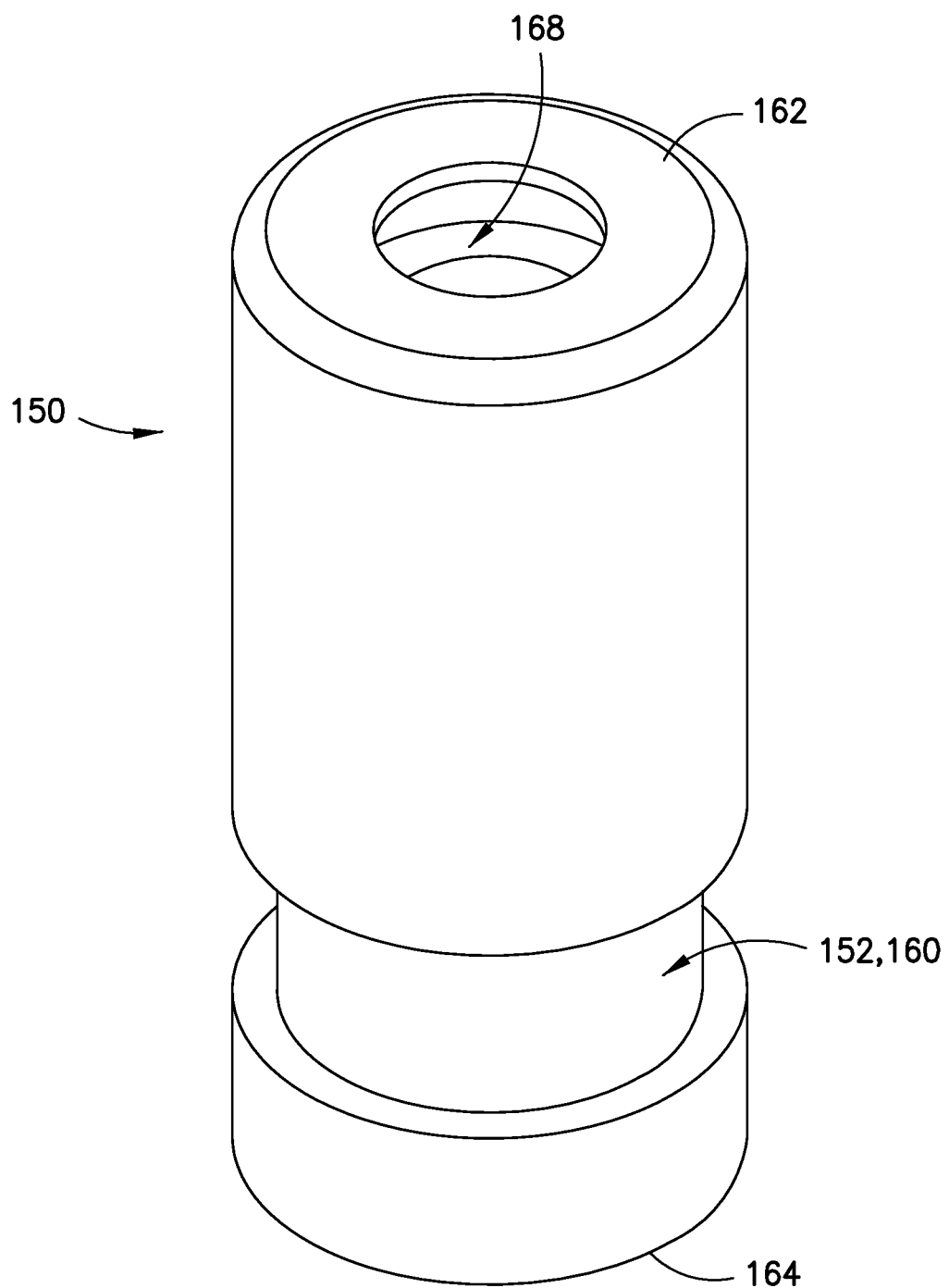
FIG. 29 is a perspective view of a connection housing in accordance with an aspect of the present invention.
Figure 32:
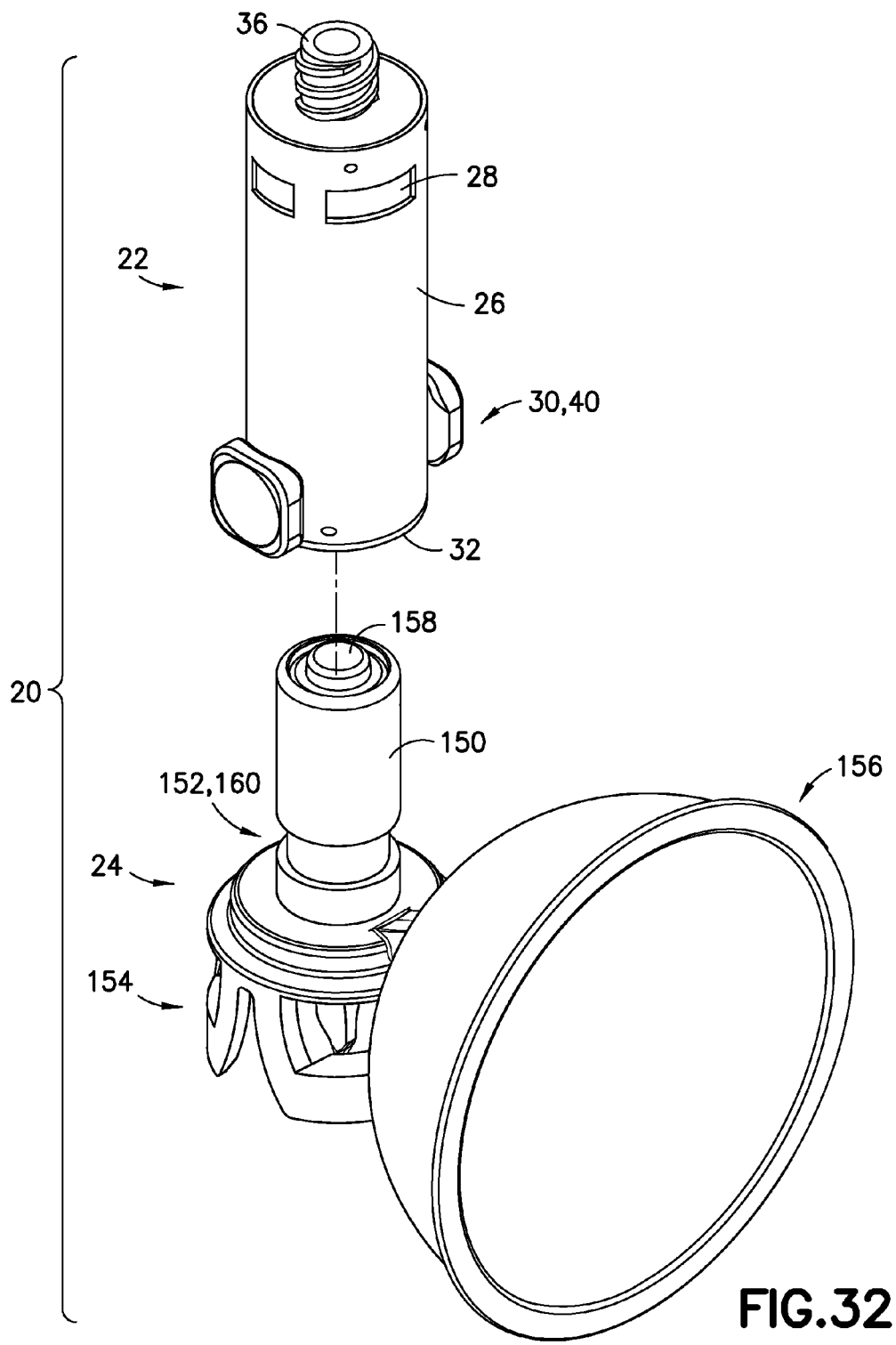
FIG. 32 is an exploded, perspective view of a syringe adapter and vial access device in accordance with an aspect of the present invention.
Figure 33:
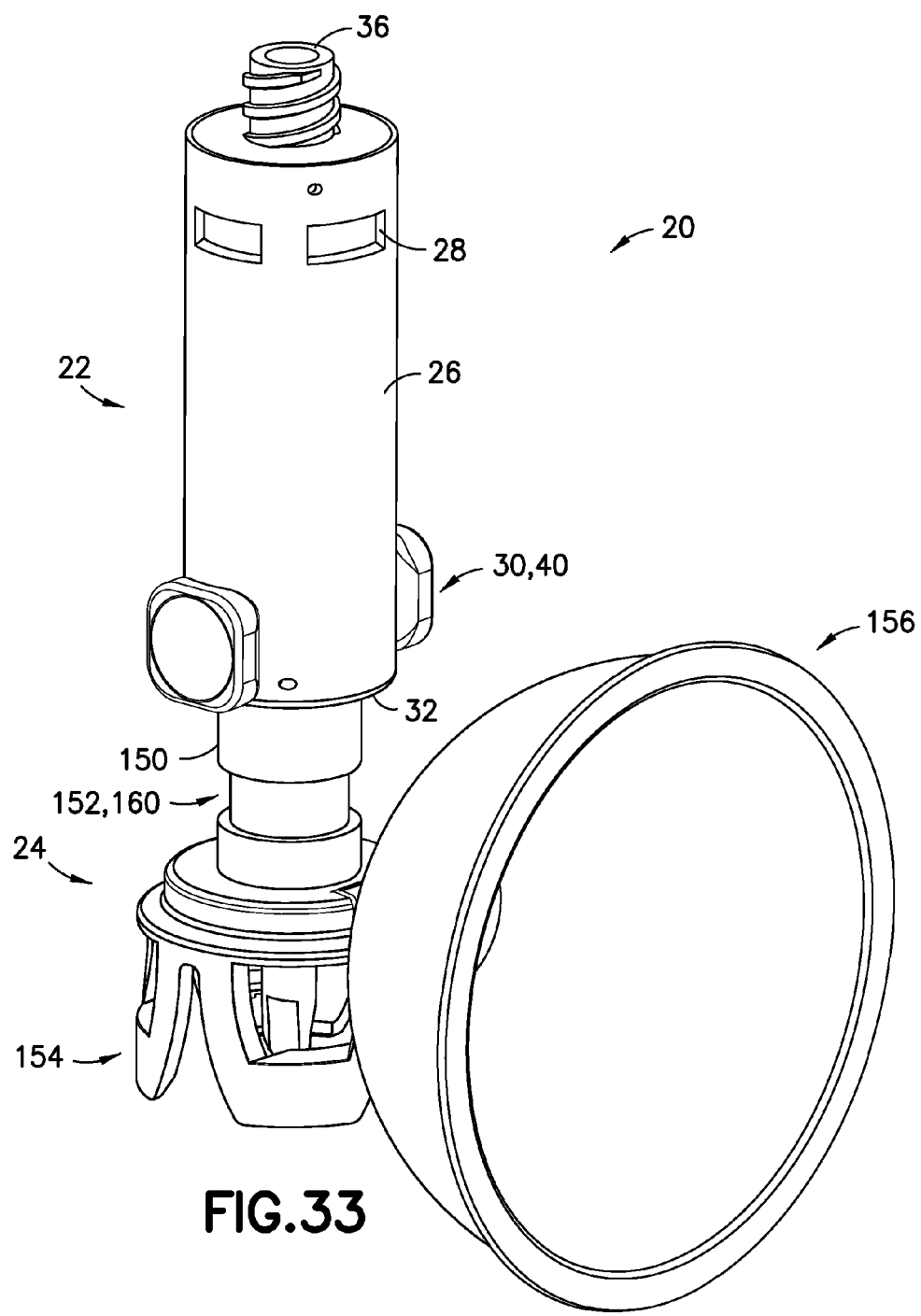
FIG. 33 is an assembled, perspective view of the syringe adapter and vial access device of FIG. 32 in accordance with an aspect of the present invention.
Figure 34:
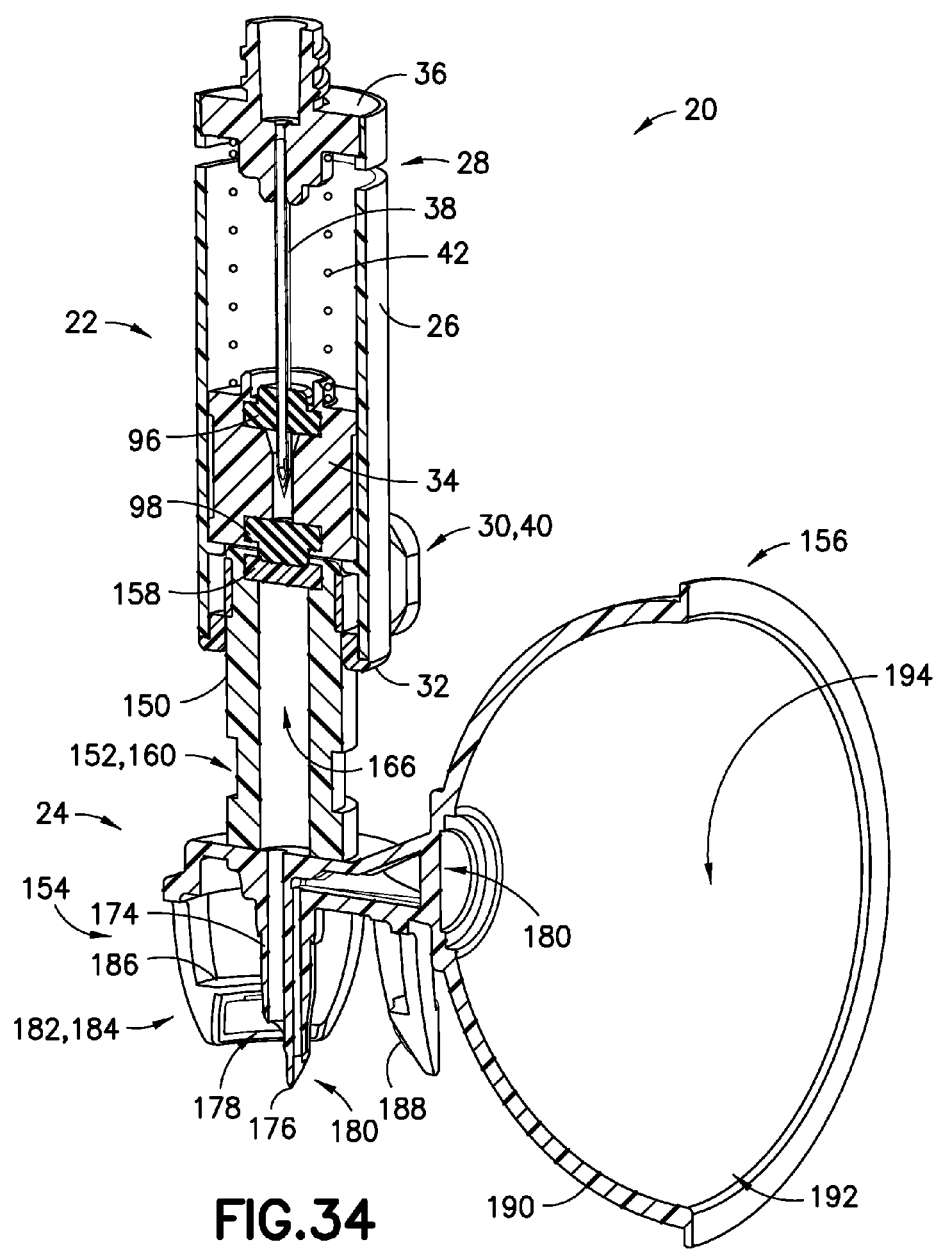
FIG. 34 is a cross-sectional view of the syringe adapter and vial access device of FIG. 33 in an initial position in accordance with an aspect of the present invention.
Figure 35:
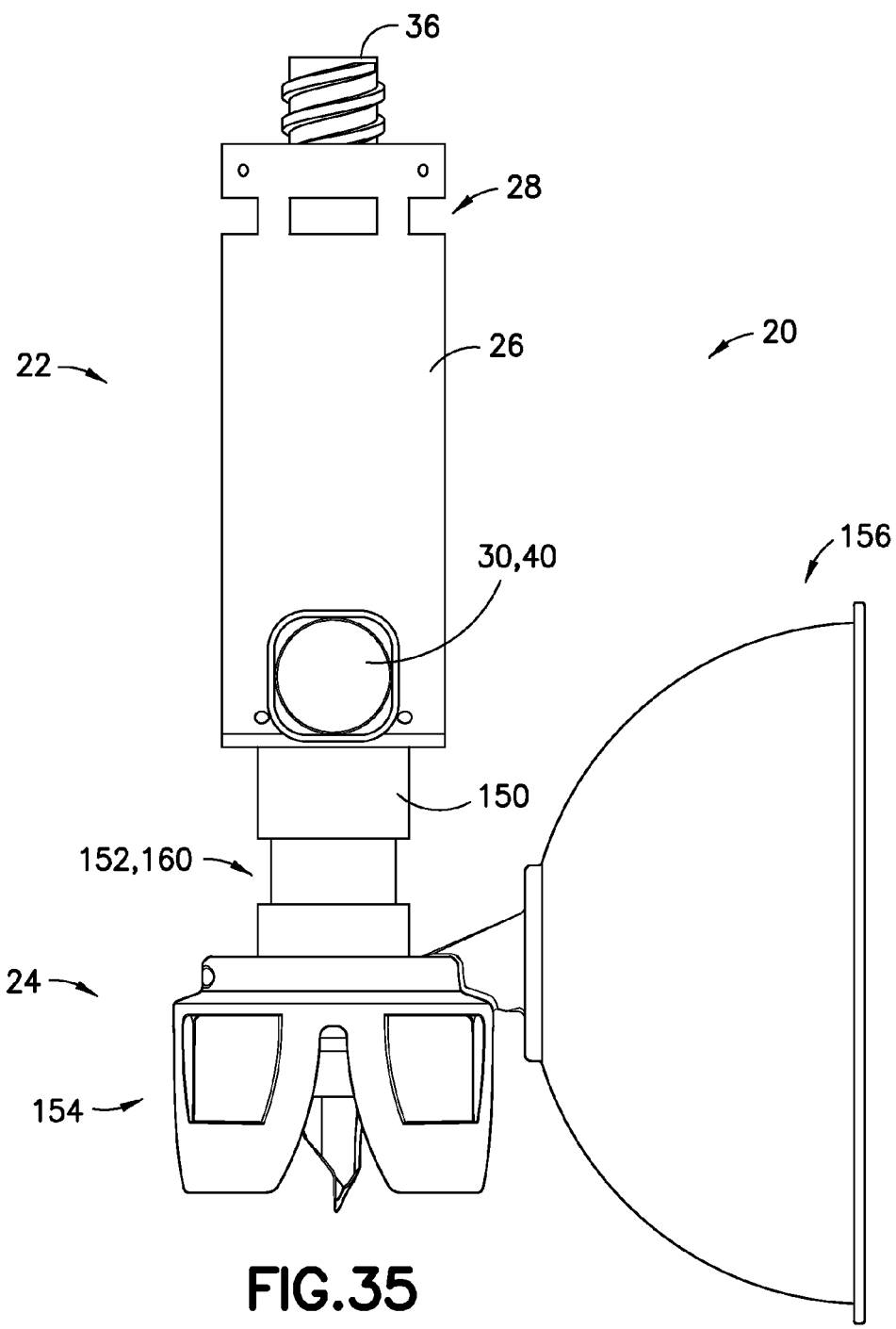
FIG. 35 is a side elevation view of a syringe adapter and vial access device in an initial position in accordance with an aspect of the present invention.
Figure 36:
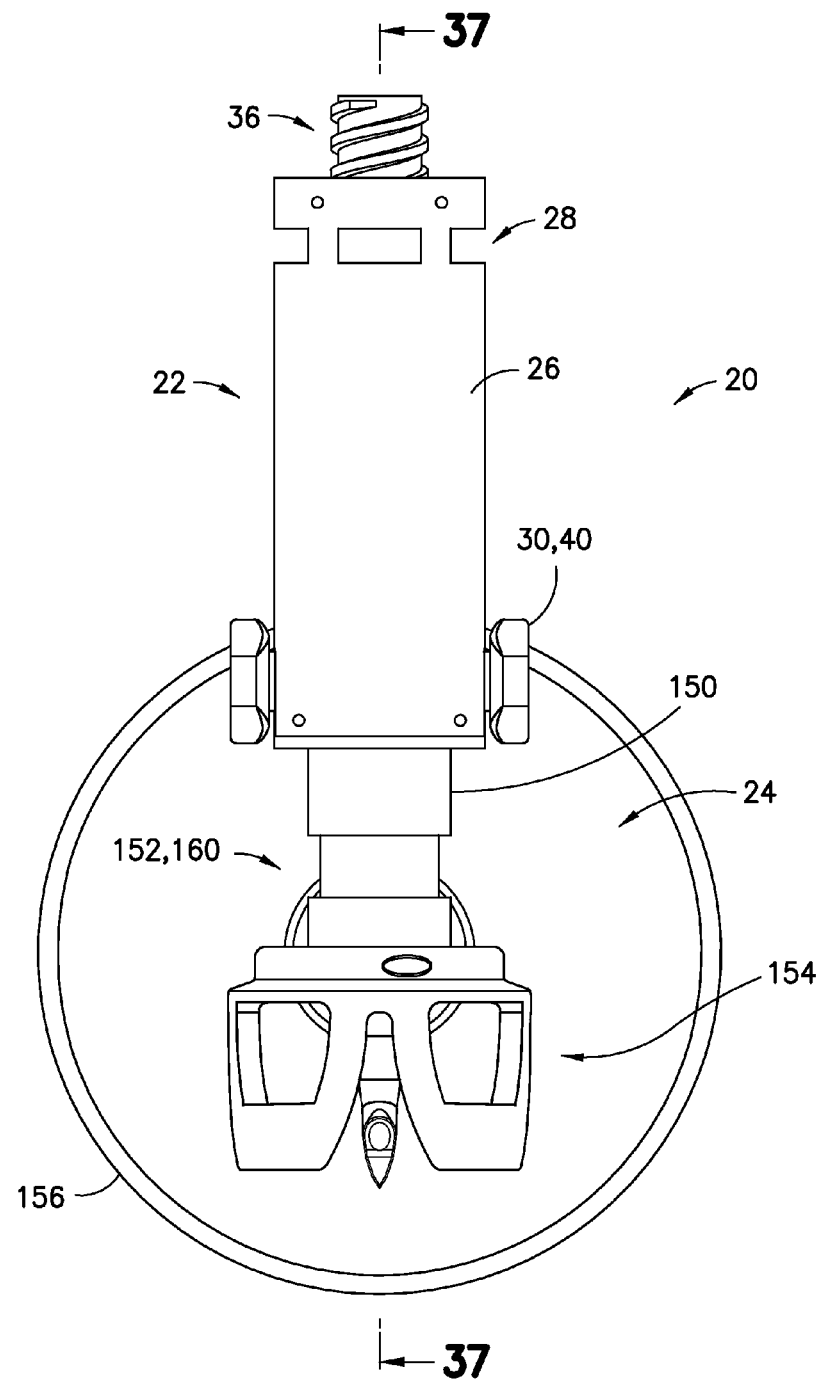
FIG. 36 is another side elevation view of a syringe adapter and vial access device in an initial position in accordance with an aspect of the present invention.
Figure 37:
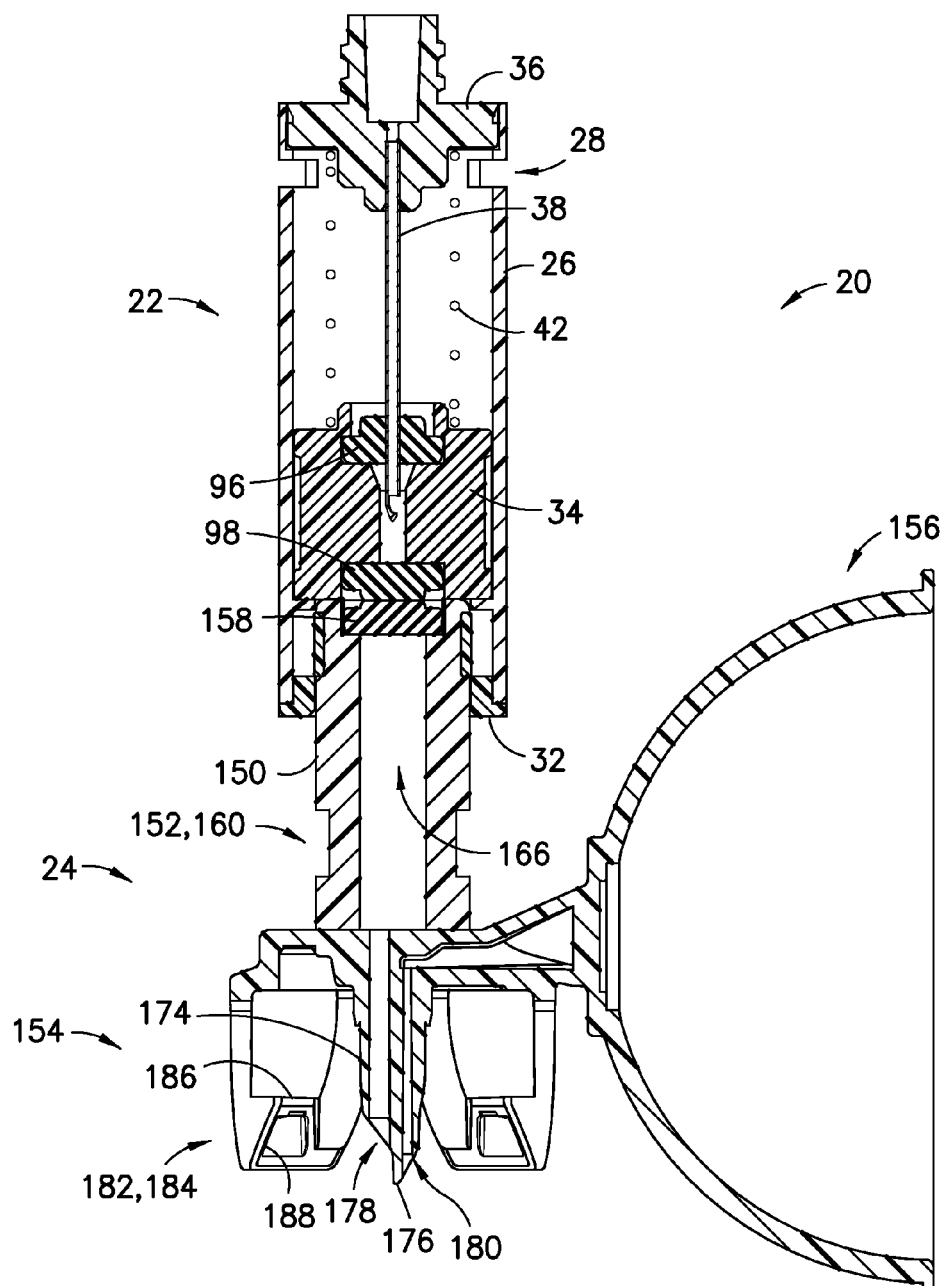
FIG. 37 is a cross-sectional view of a syringe adapter and vial access device in an initial position taken along line 37-37 of FIG. 36 in accordance with an aspect of the present invention.
Figure 38:
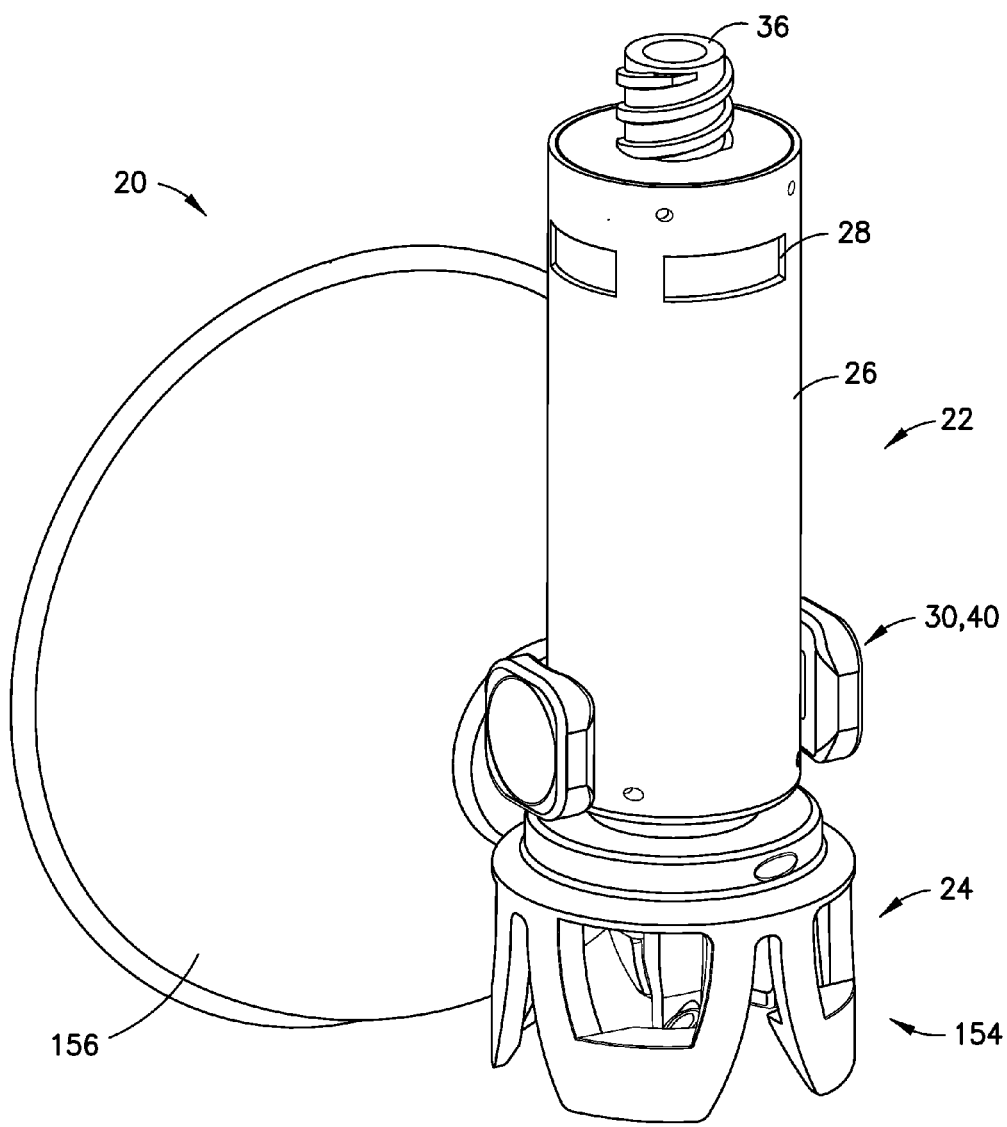
FIG. 38 is a perspective view of a syringe adapter and vial access device in an activated position in accordance with an aspect of the present invention.
Figure 39:
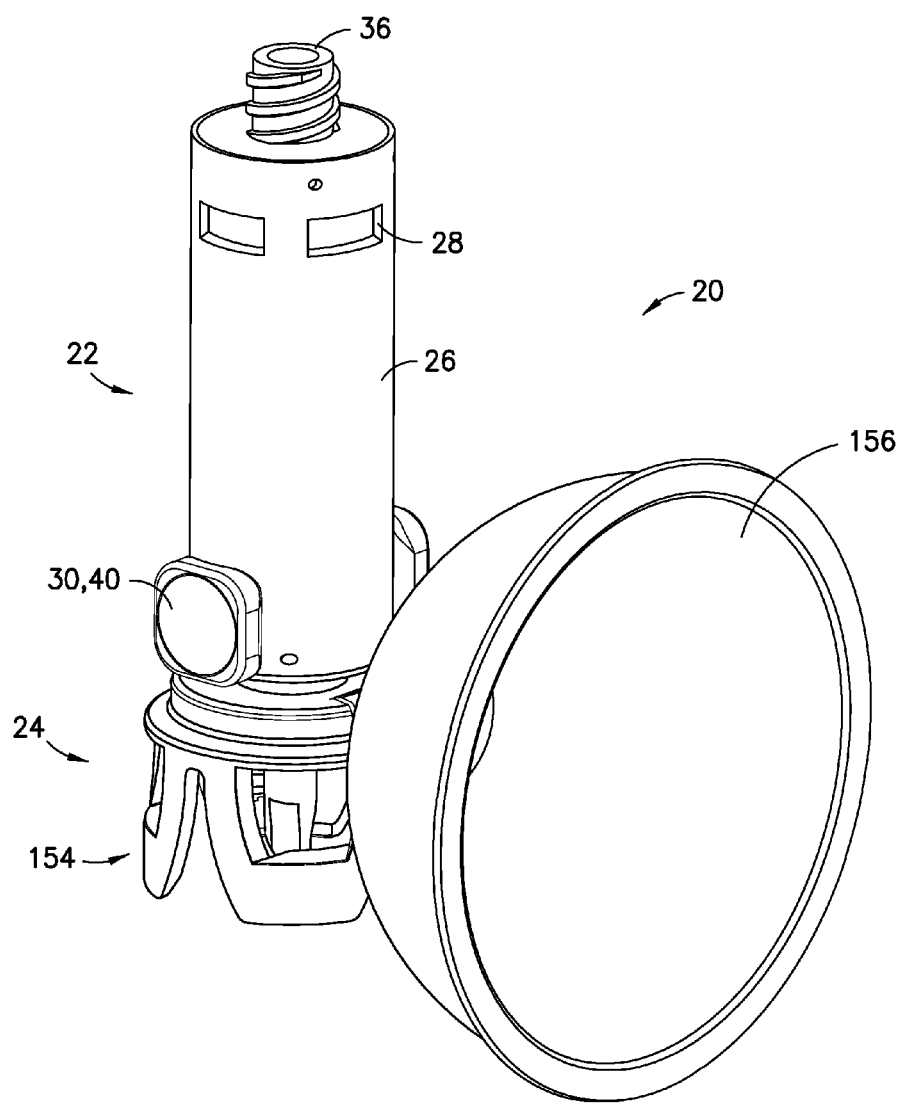
FIG. 39 is another perspective view of a syringe adapter and vial access device in an activated position in accordance with an aspect of the present invention.

Referring to FIGS. 26-28, vial access device 24 generally includes a connection housing 150 having a lock portion 152, a base 154, a pressure equalization system 156, and a seal membrane 158 as described in more detail below.

Referring to FIGS. 26-31, connection housing 150 generally includes first or proximal end 162, second or distal end 164, undercut 160, fluid channel 166, and seal membrane cavity 168. Undercut 160 is disposed adjacent second end 164 and is configured to receive push button spring 40 to lock syringe adapter 22 to vial access device 24 with translating housing 34 in the activated position as shown in FIGS. 38-44. Fluid channel 166 extends from first end 162 to second end 164.

Figure 40:
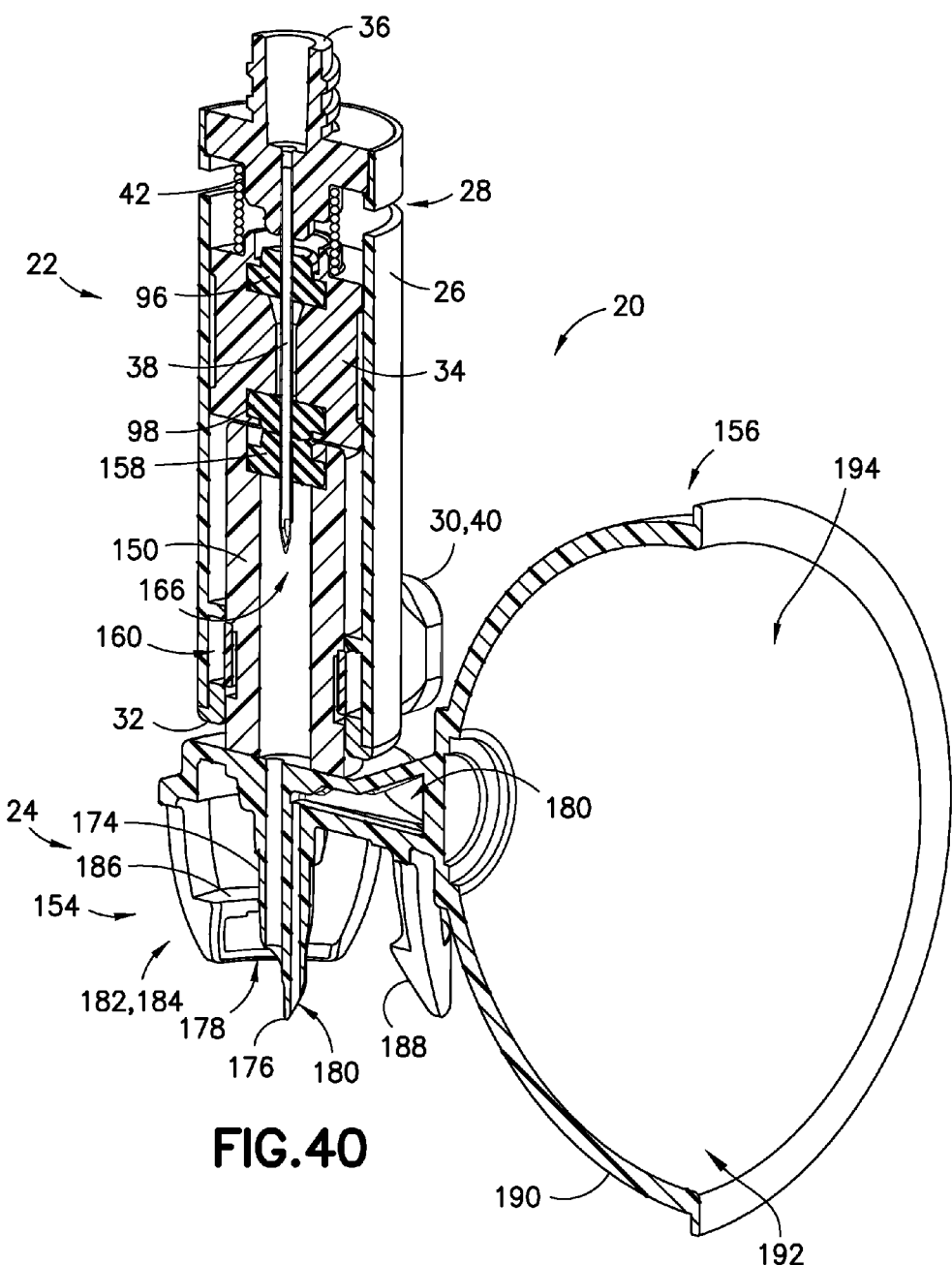
FIG. 40 is a cross-sectional view of the syringe adapter and vial access device of FIG. 39 in an activated position in accordance with an aspect of the present invention.
Figure 41:
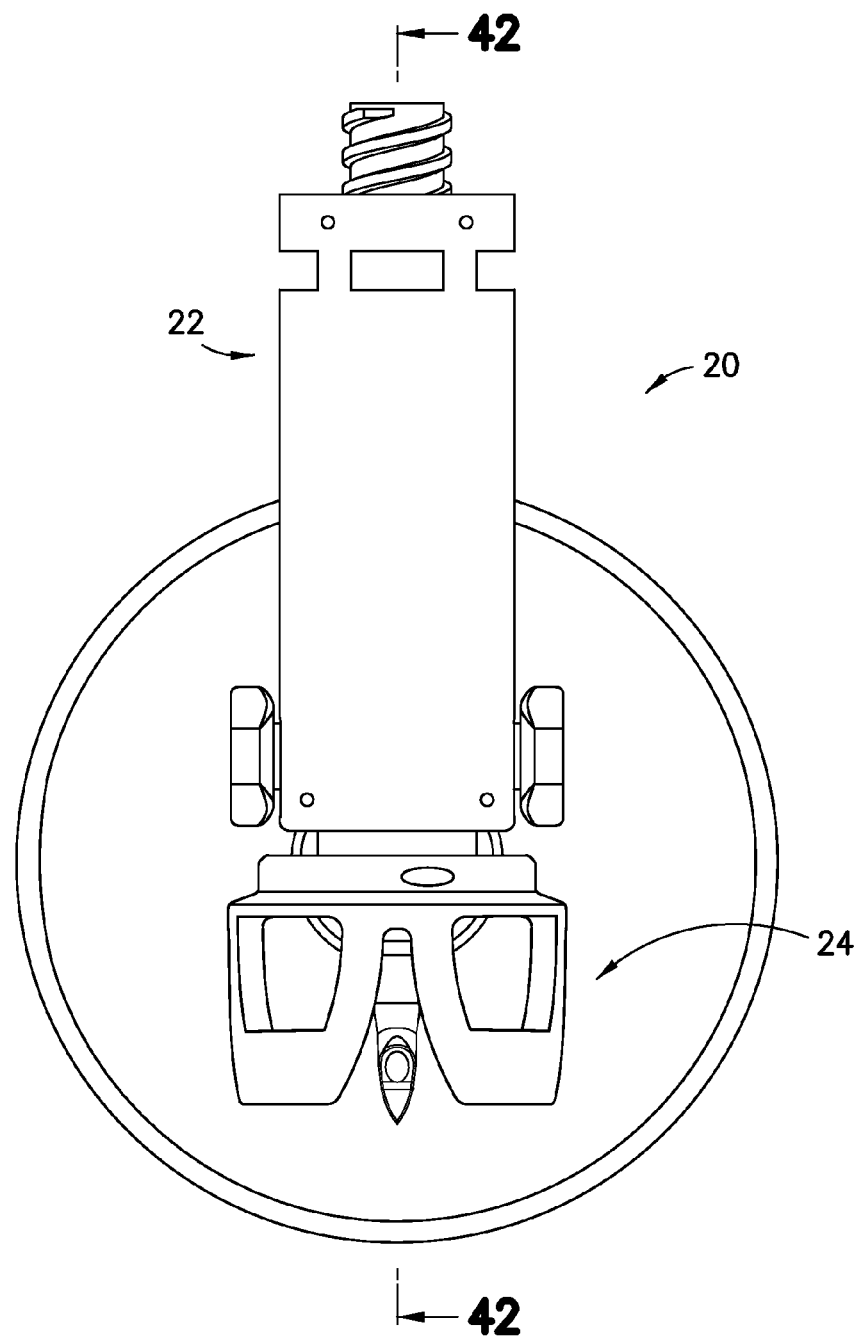
FIG. 41 is a side elevation view of a syringe adapter and vial access device in an activated position in accordance with an aspect of the present invention.
Figure 42:
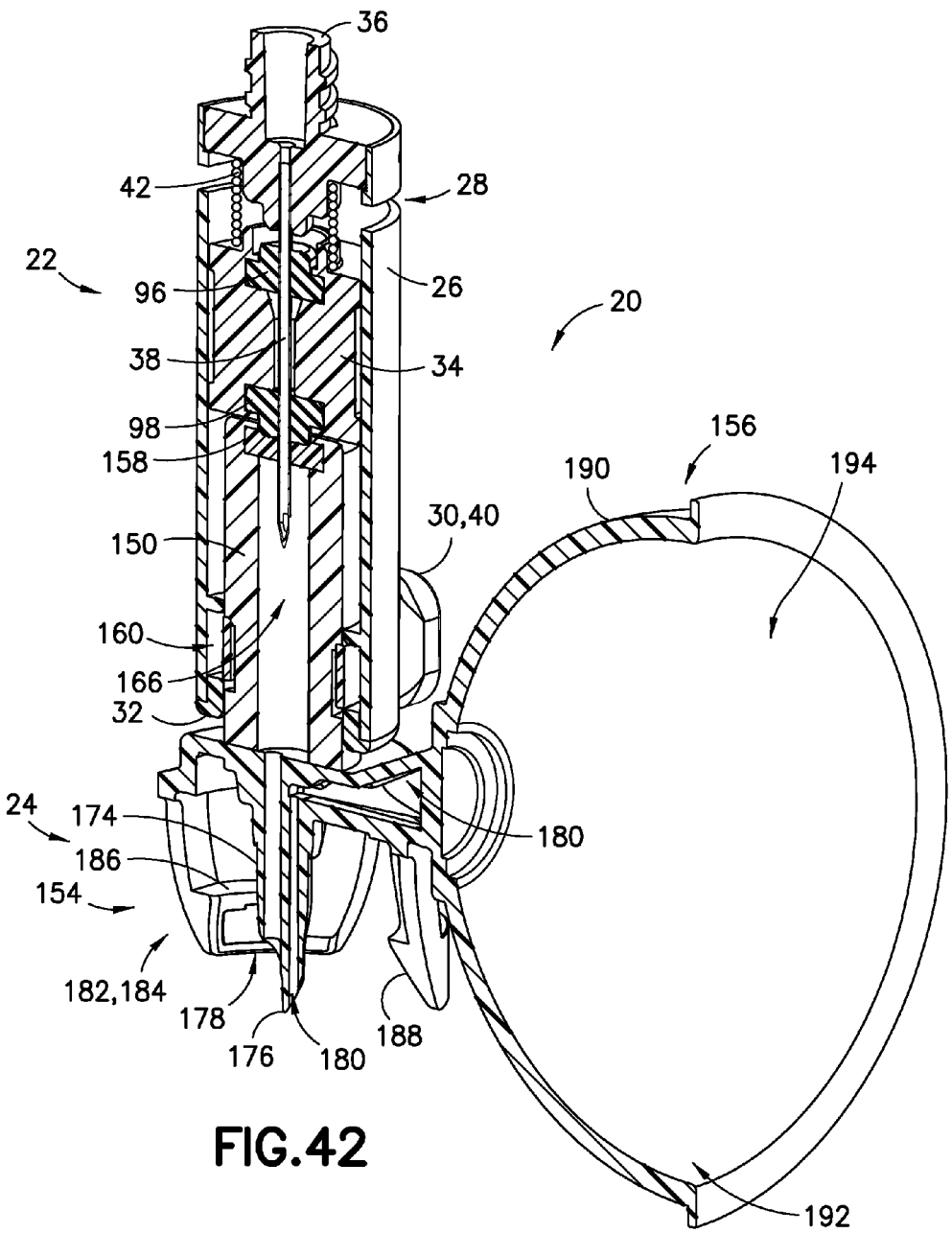
FIG. 42 is a cross-sectional view of a syringe adapter and vial access device in an activated position taken along line 42-42 of FIG. 41 in accordance with an aspect of the present invention.
Figure 43:
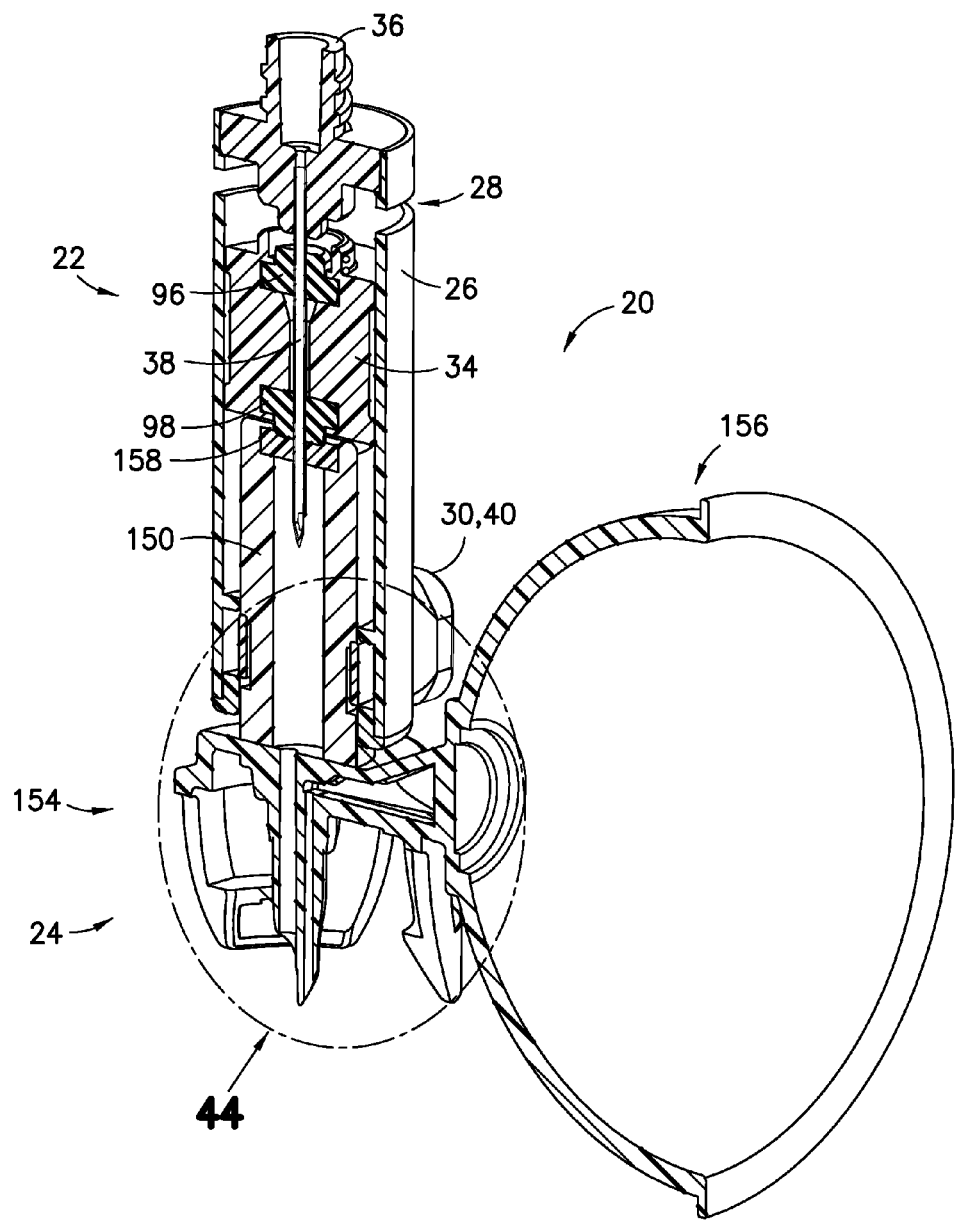
FIG. 43 is another cross-sectional view of a syringe adapter and vial access device in an activated position of FIG. 41 in accordance with an aspect of the present invention.
Figure 44:
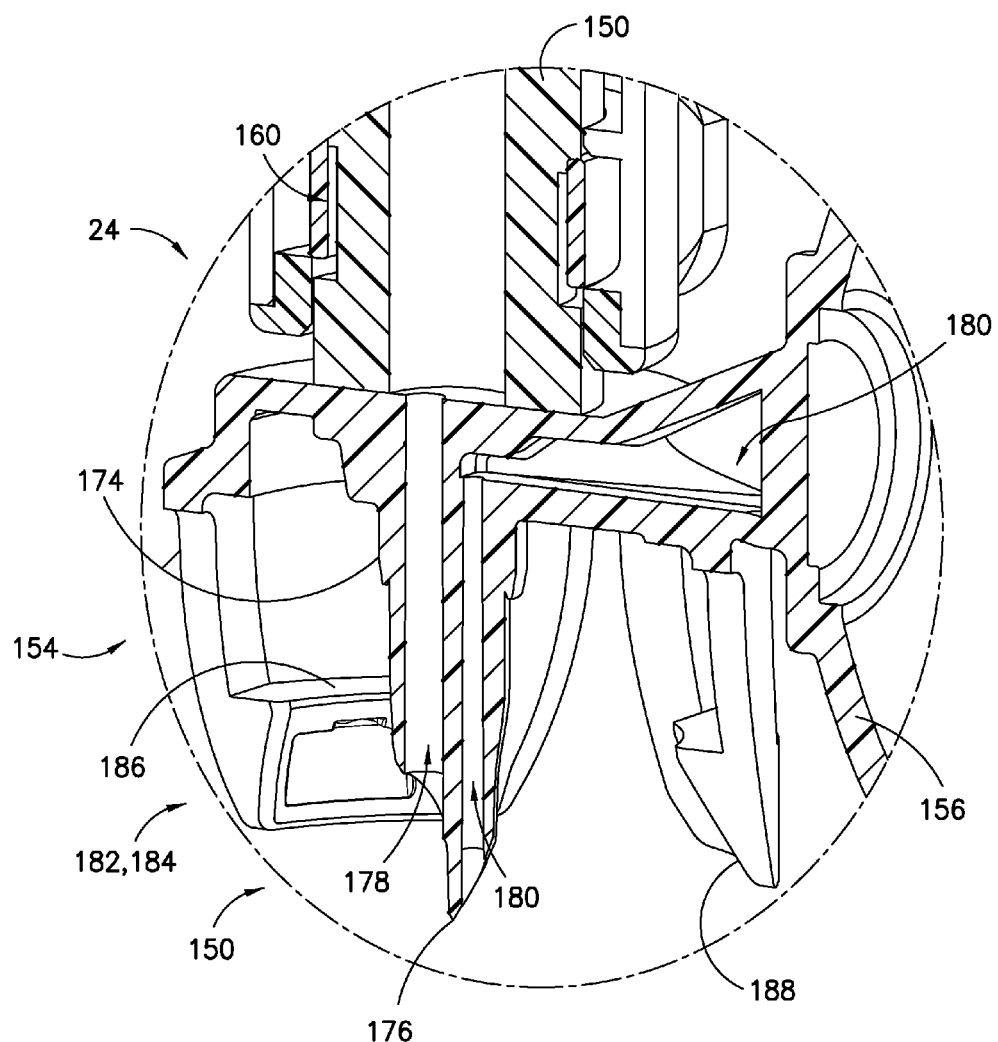
FIG. 44 is an enlarged view of a portion of the vial access device taken along section 44 of FIG. 43 in accordance with an aspect of the present invention.
Figure 45:
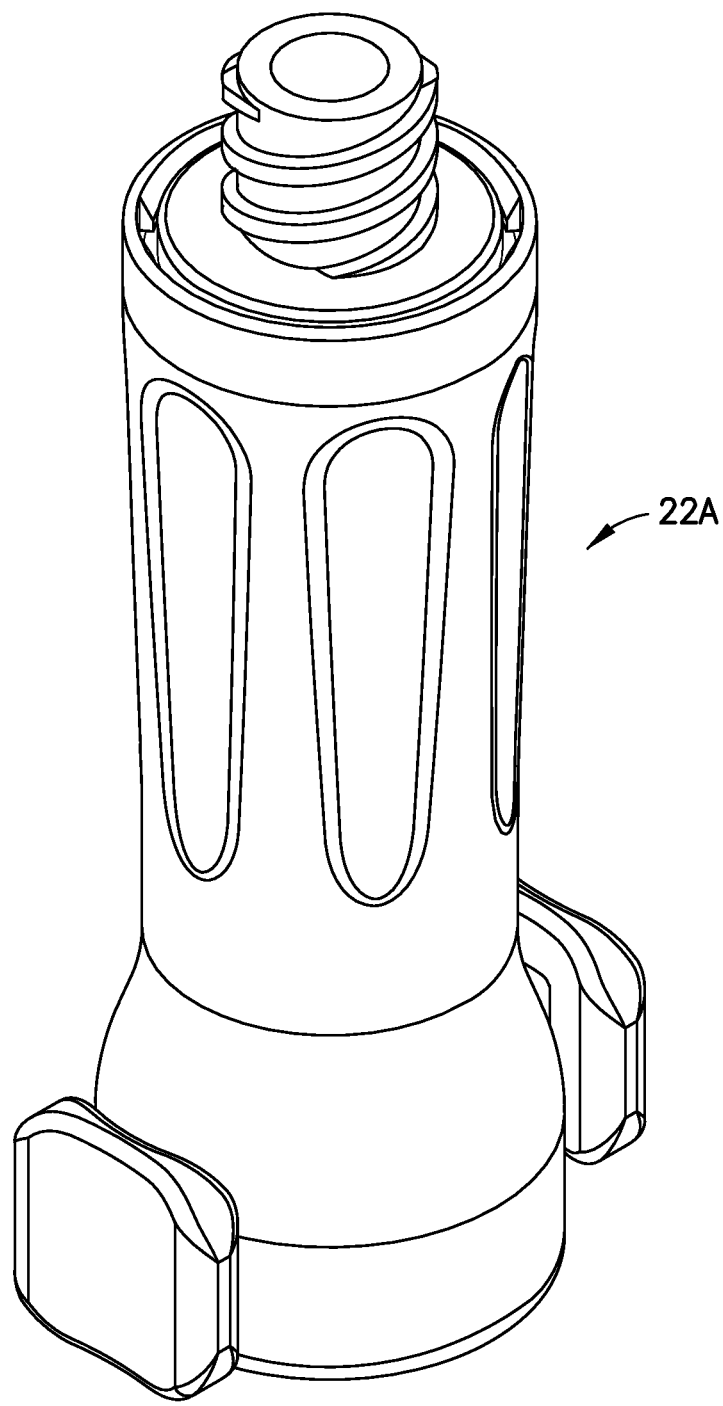
FIG. 45 is a perspective view of a syringe adapter in accordance with another aspect of the present invention.
Figure 46:
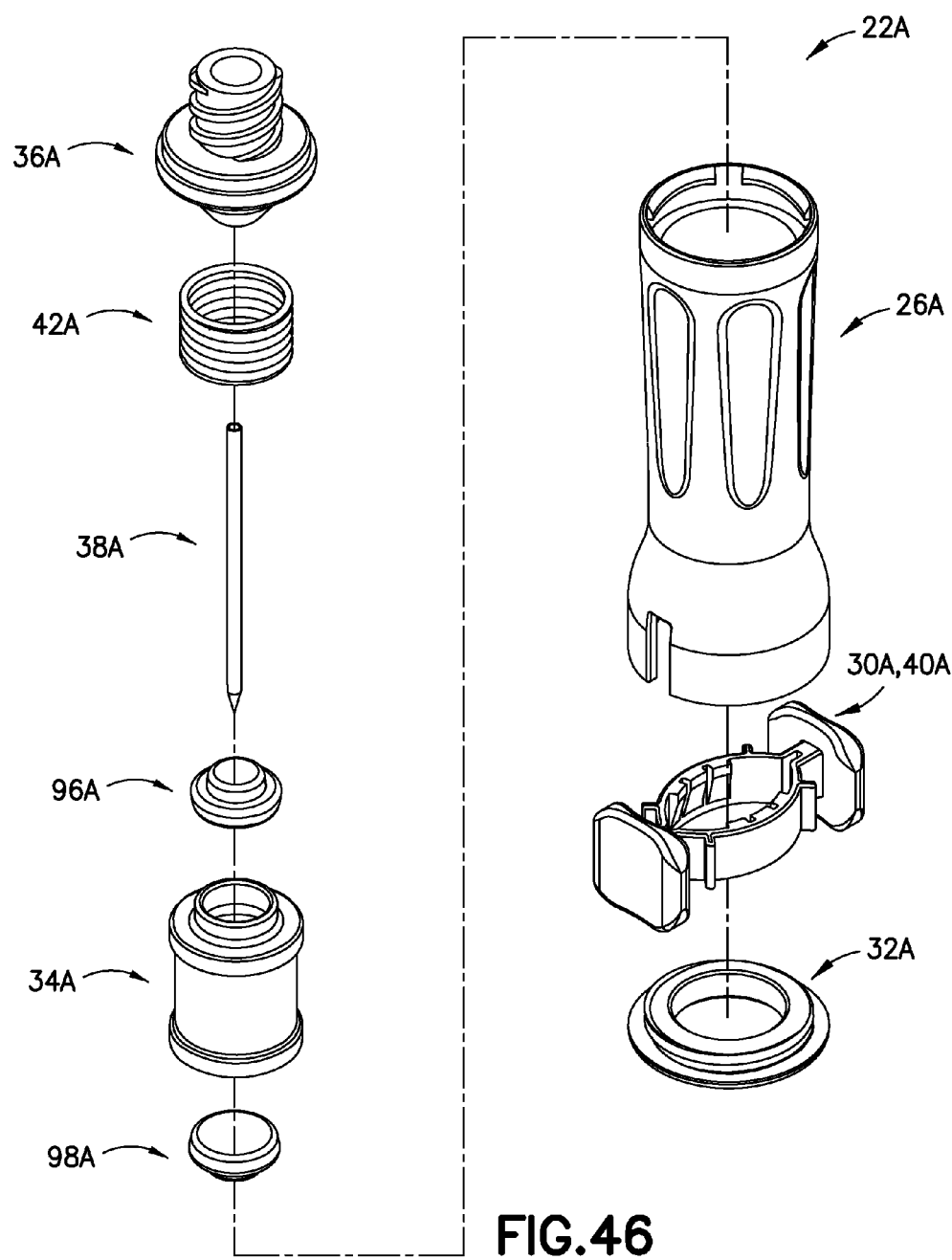
FIG. 46 is an exploded, perspective view of a syringe adapter in accordance with another aspect of the present invention.
Figure 47:
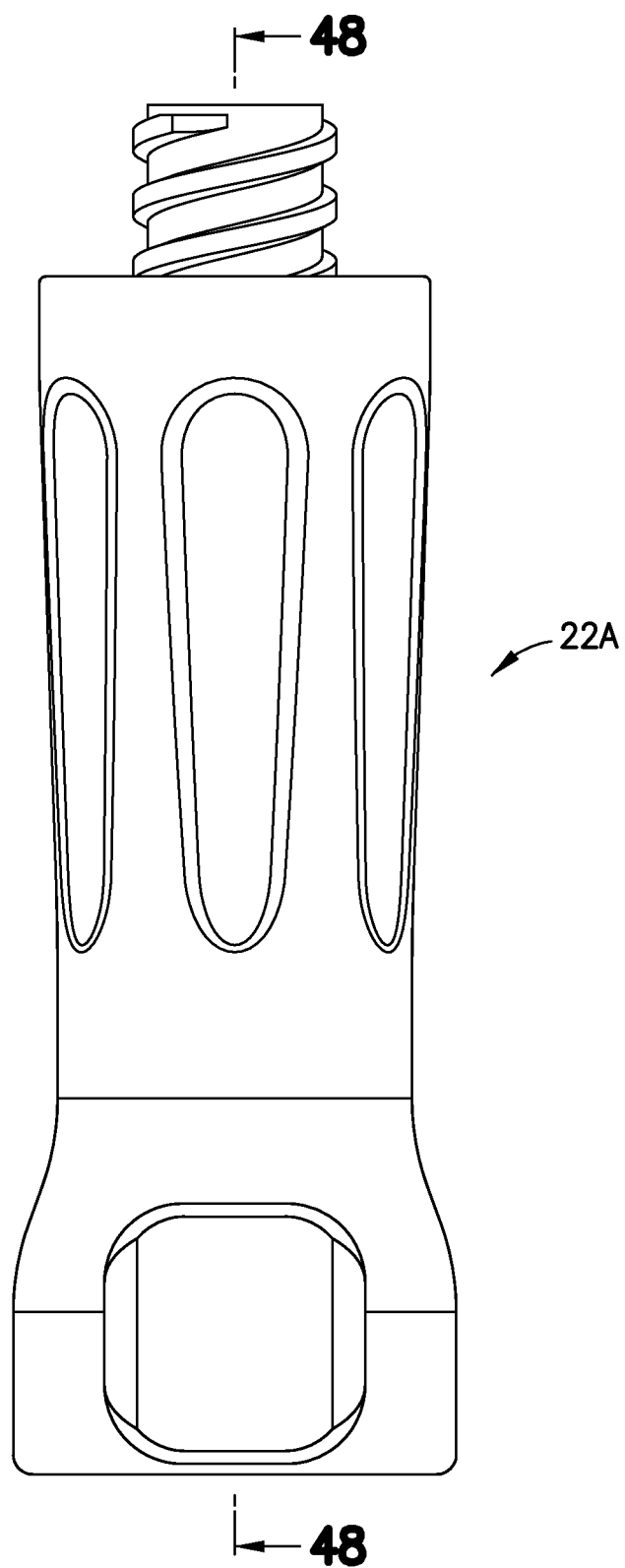
FIG. 47 is an assembled, side elevation view of the syringe adapter of FIG. 46 in accordance with another aspect of the present invention.
Figure 48:
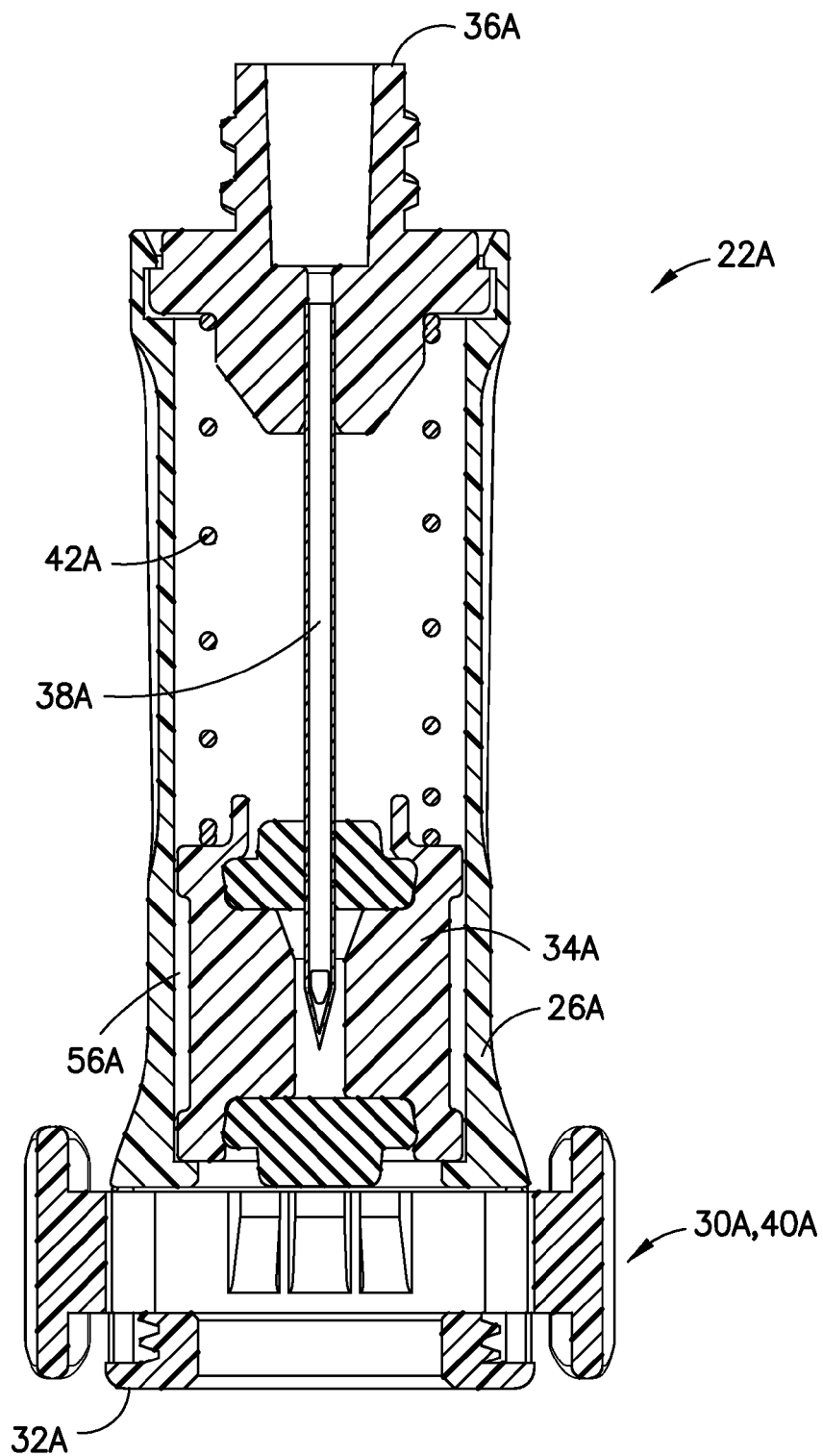
FIG. 48 is a cross-sectional view of a syringe adapter taken along line 48-48 of FIG. 47 in accordance with another aspect of the present invention.
Figure 49:
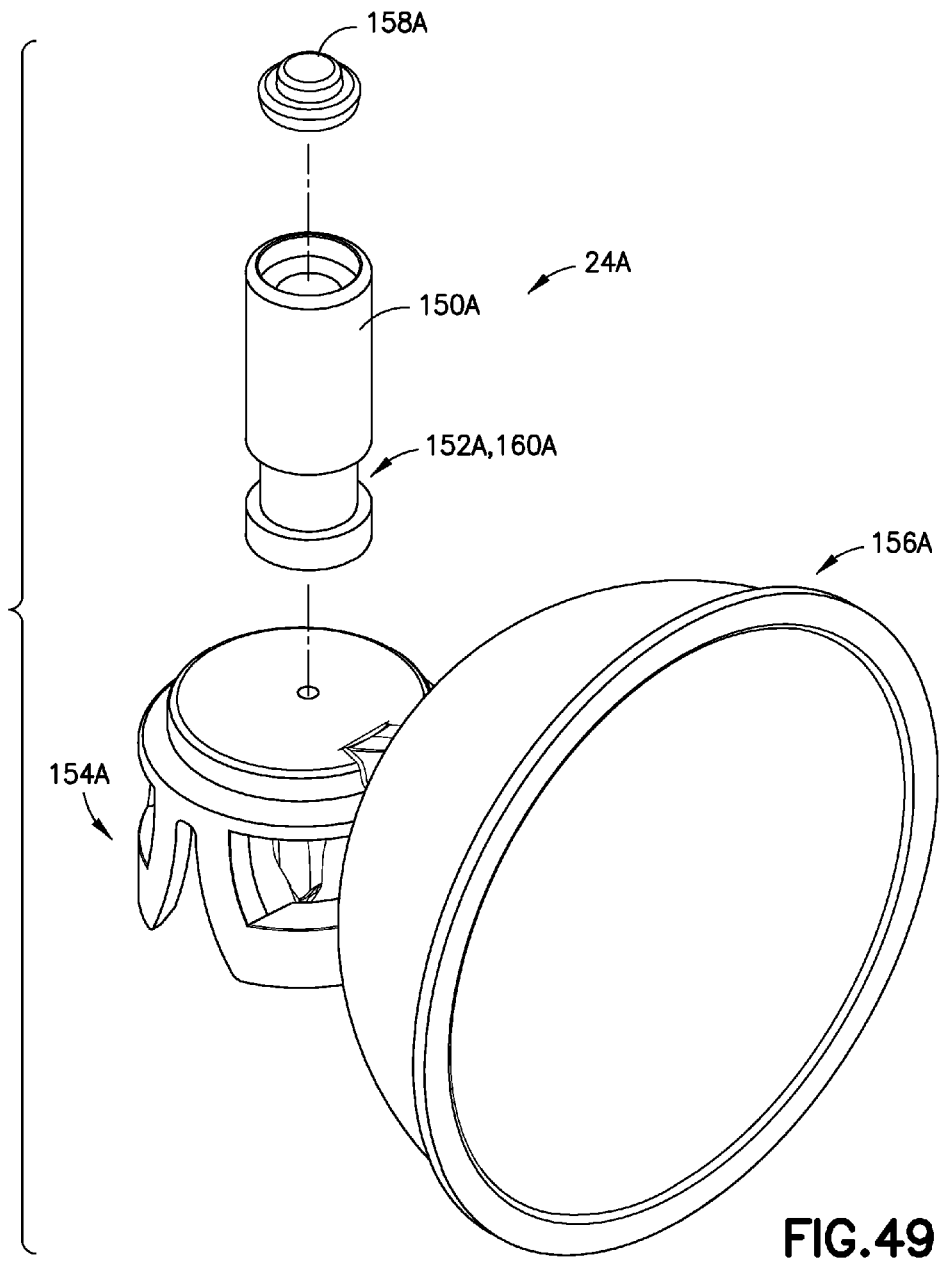
FIG. 49 is an exploded, perspective view of a vial access device in accordance with another aspect of the present invention.
Figure 50:
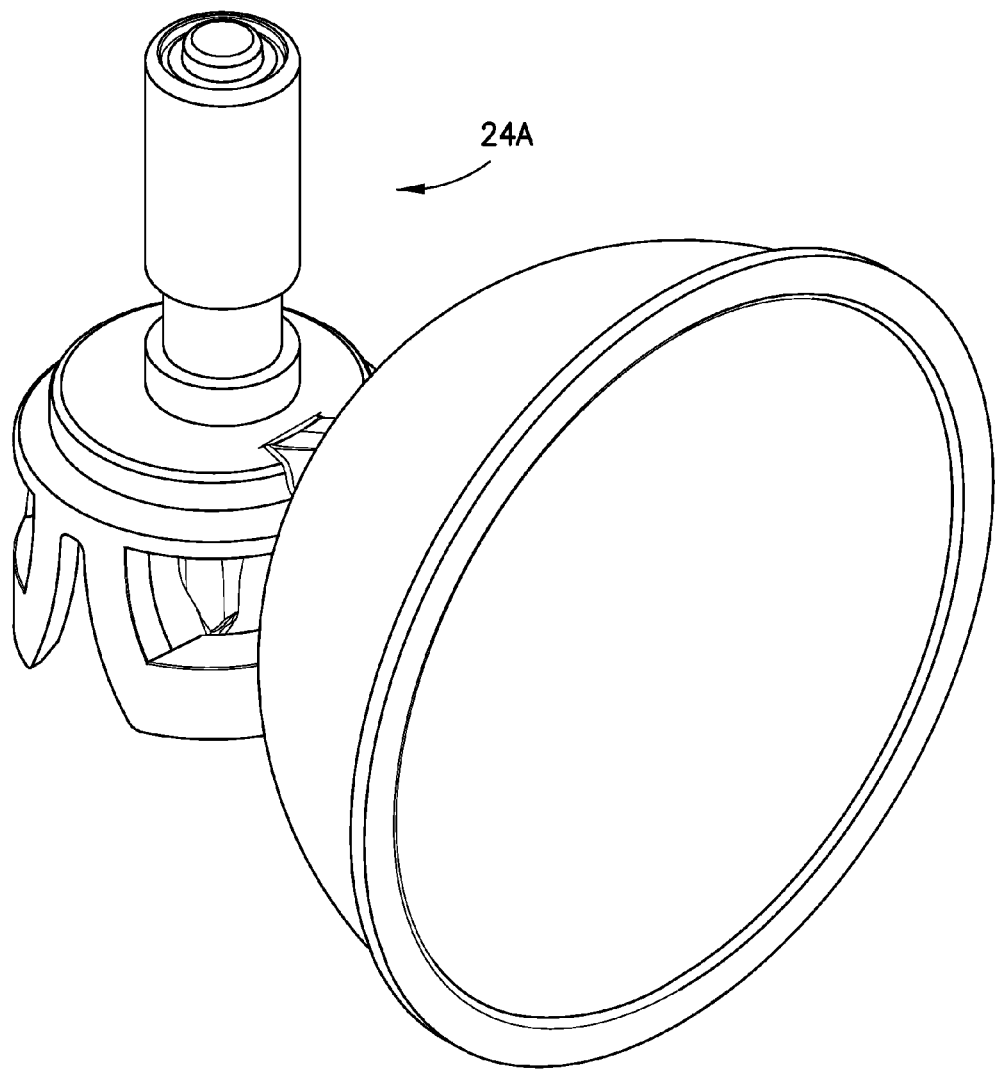
FIG. 50 is an assembled, perspective view of the vial access device of FIG. 49 in accordance with another aspect of the present invention.
Figure 51:
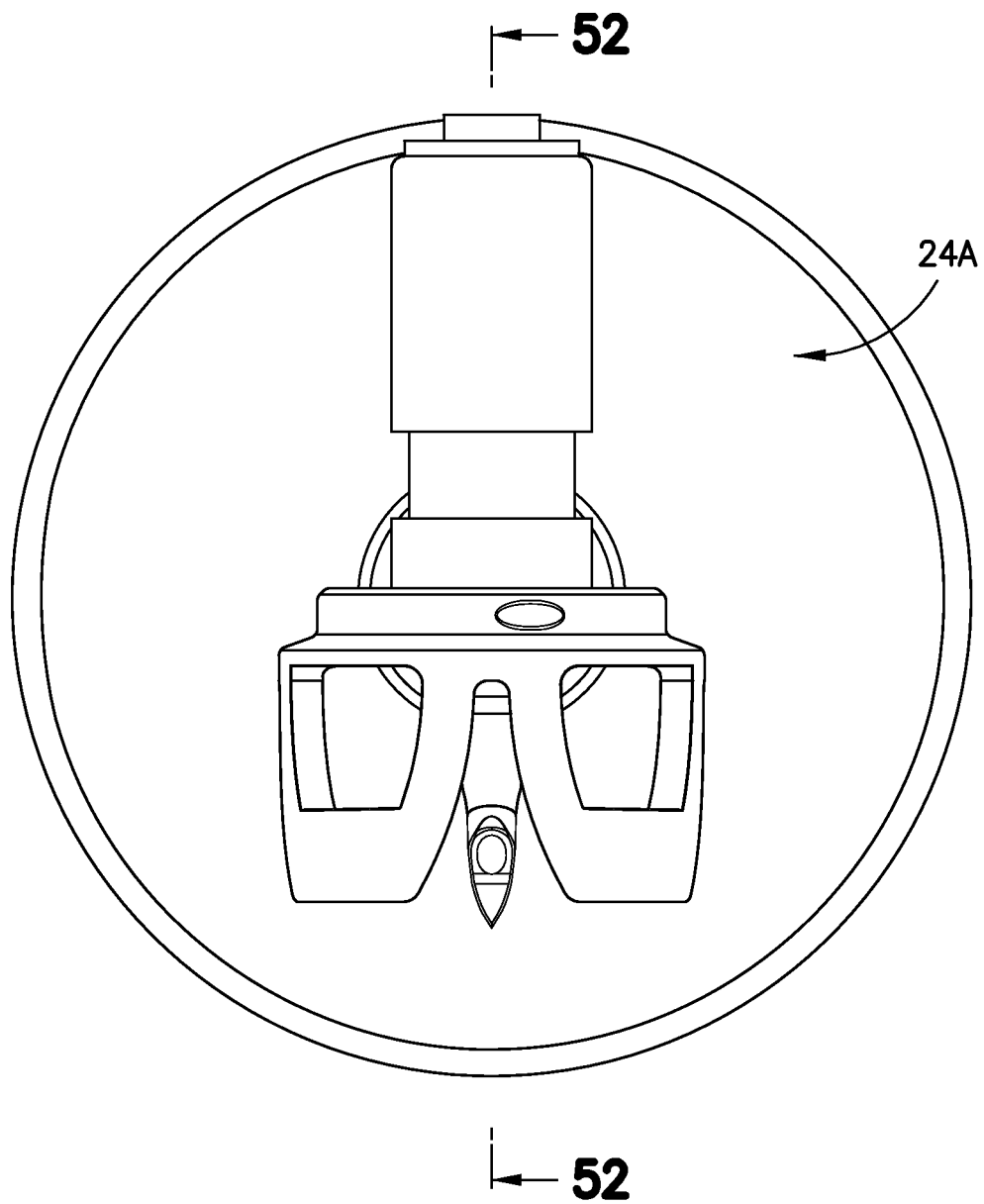
FIG. 51 is a side elevation view of a vial access device in accordance with another aspect of the present invention.
Figure 52:
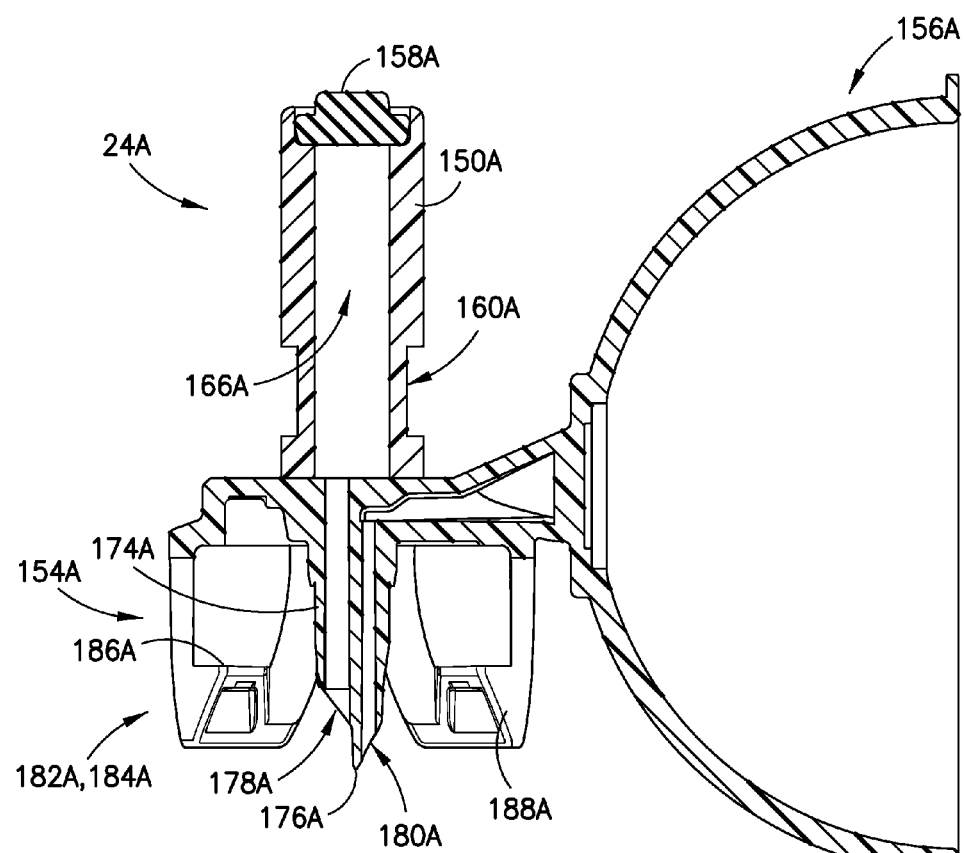
FIG. 52 is a cross-sectional view of a vial access device taken along line 52-52 of FIG. 51 in accordance with another aspect of the present invention.
Figure 56:
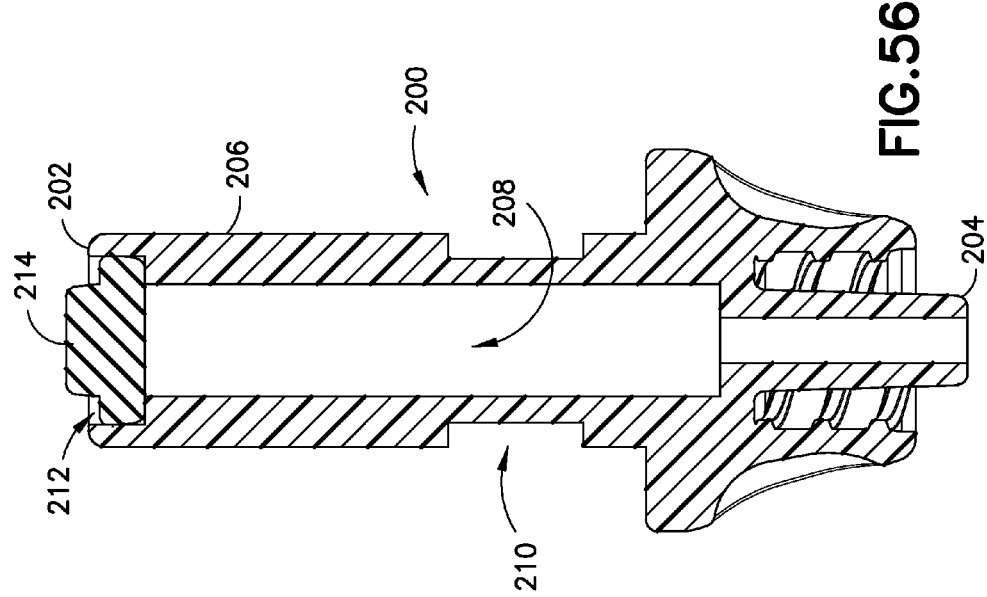
FIG. 56 is a cross-sectional view of a connector taken along line 56-56 of FIG. 55 in accordance with an aspect of the present invention.
Figure 55:
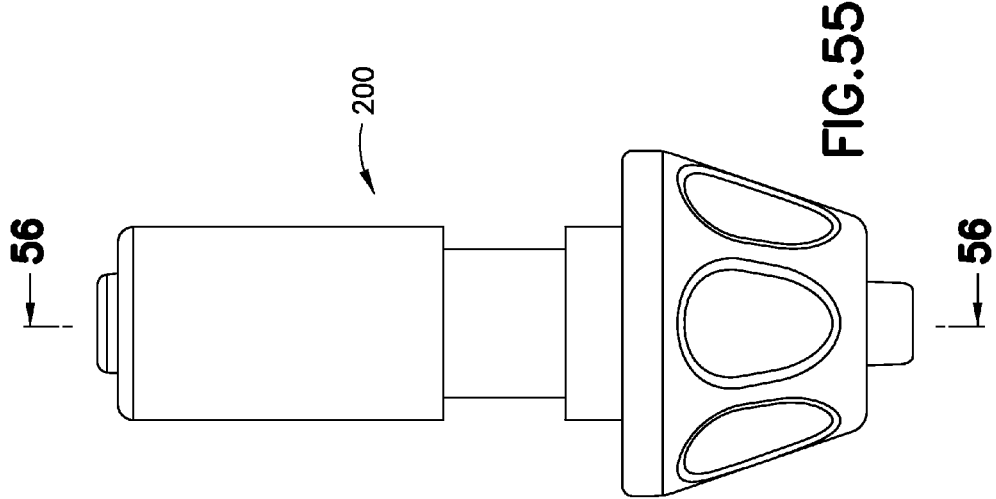
FIG. 55 is a side elevation view of a connector in accordance with an aspect of the present invention.
Figure 57:
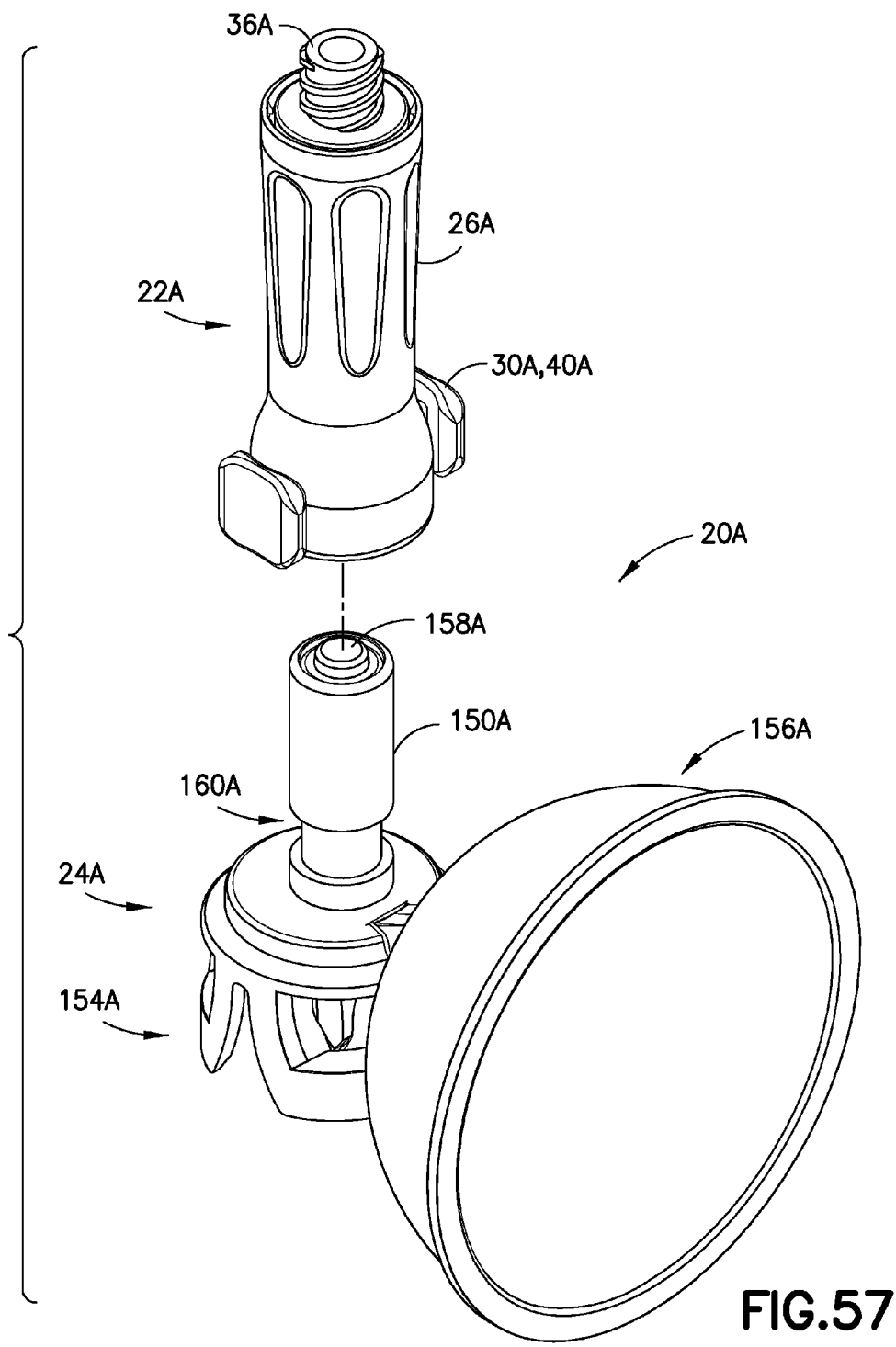
FIG. 57 is an exploded, perspective view of a syringe adapter and vial access device in accordance with another aspect of the present invention.
Figure 58:
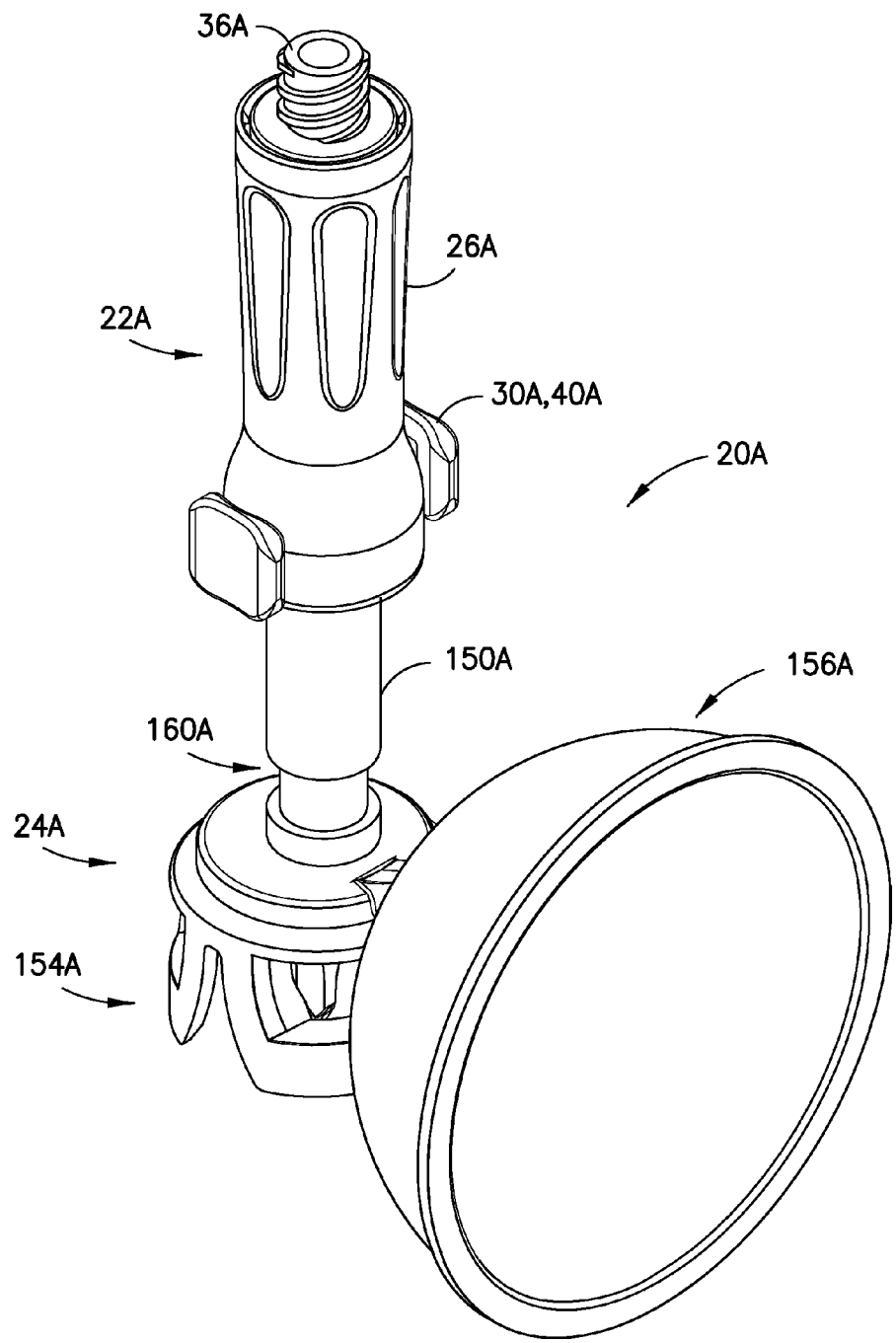
FIG. 58 is an assembled, perspective view of the syringe adapter and vial access device of FIG. 57 in accordance with an aspect of the present invention.
Figure 59:
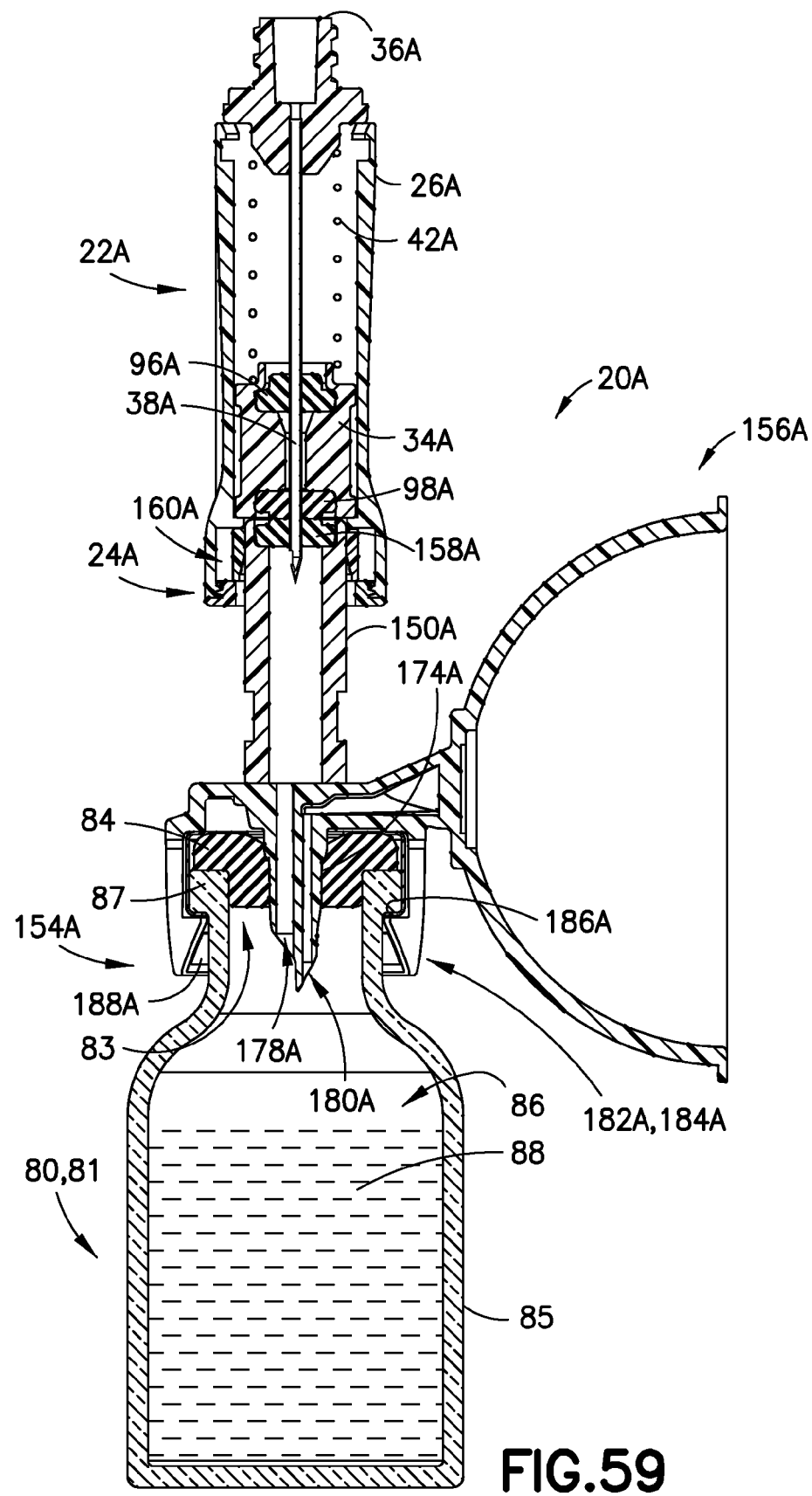
FIG. 59 is a cross-sectional view of the syringe adapter and vial access device of FIG. 58 in an initial position in accordance with an aspect of the present invention.
Figure 60:
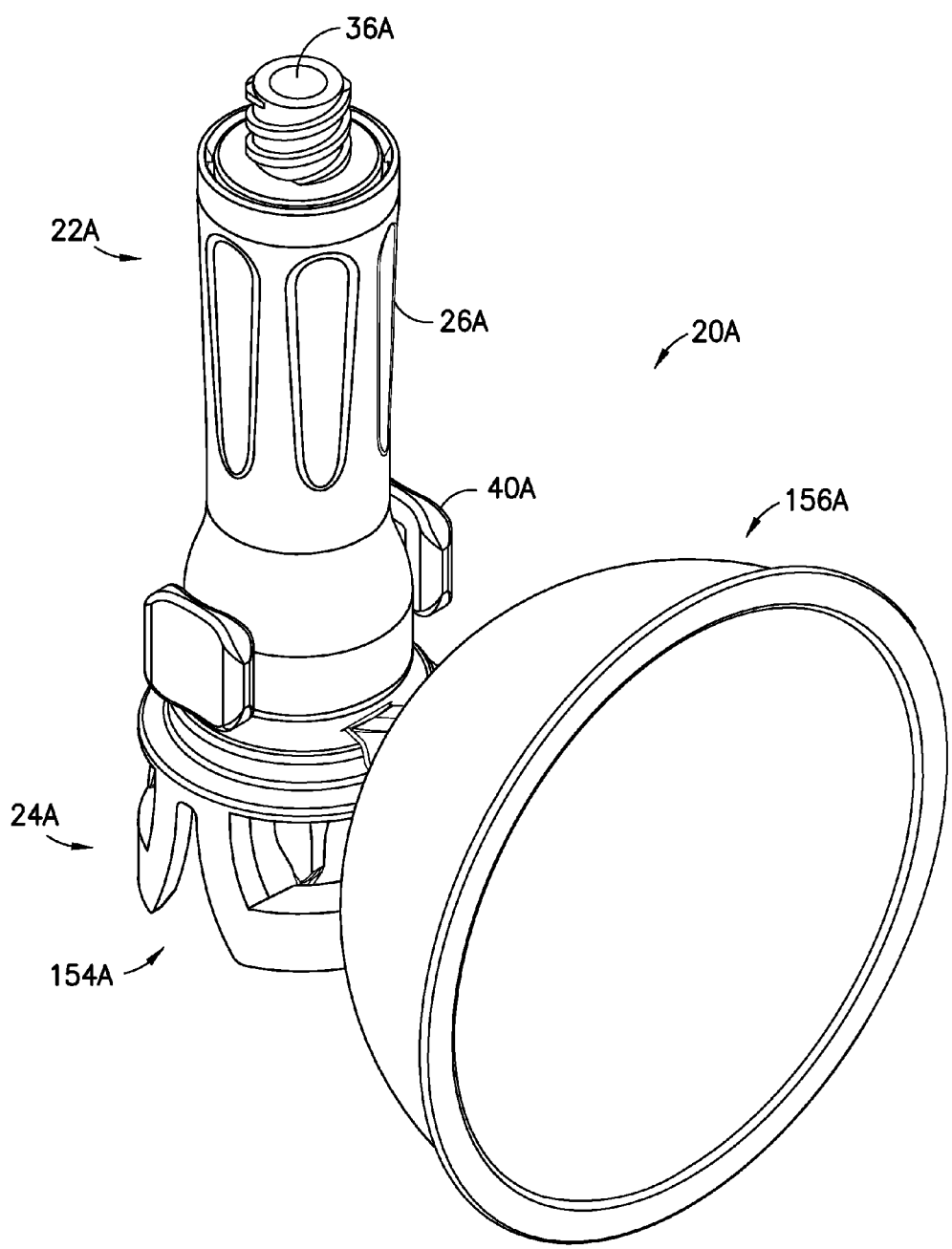
FIG. 60 is a perspective view of a syringe adapter and vial access device in an activated position in accordance with another aspect of the present invention.
Figure 61:
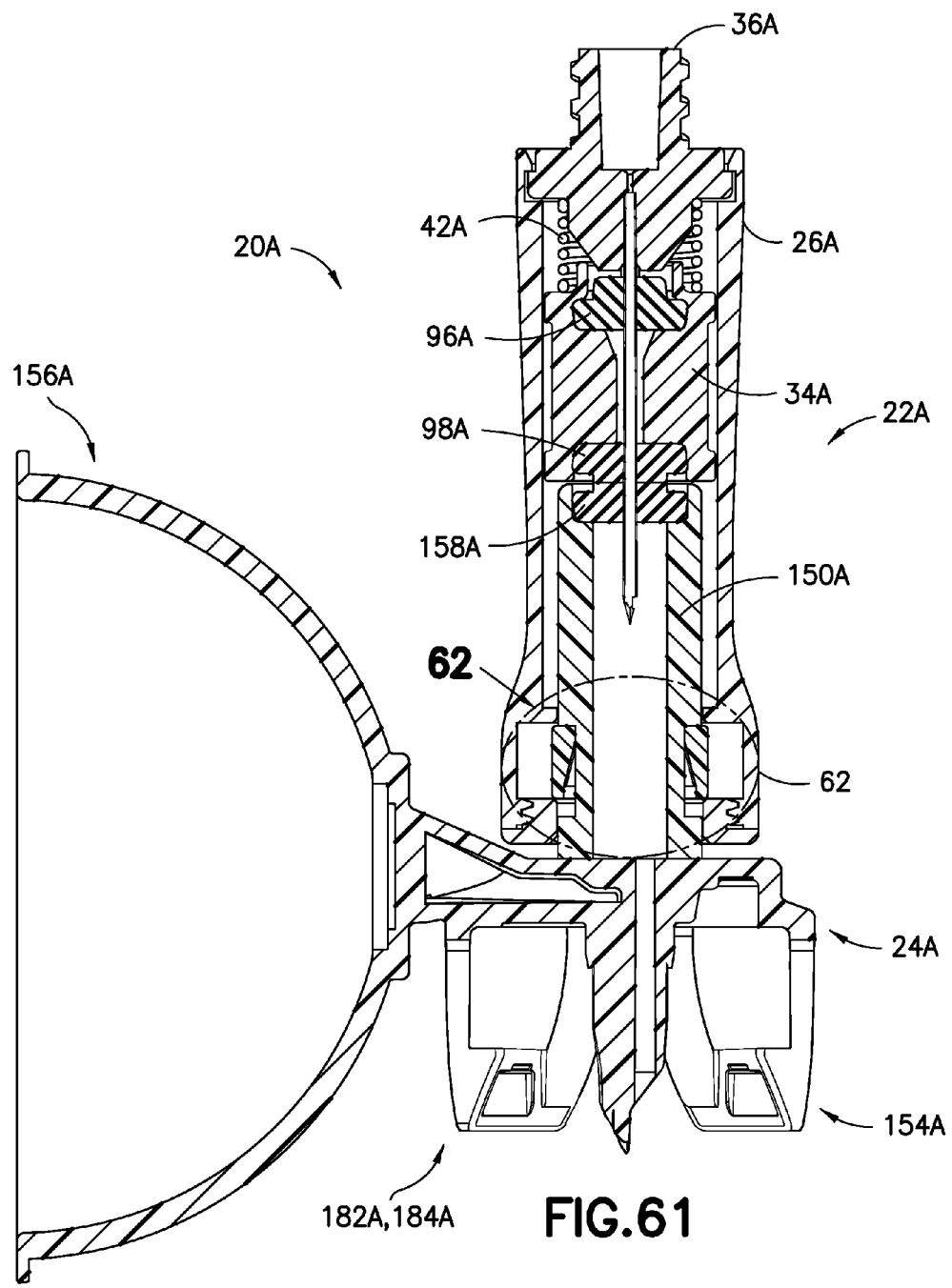
FIG. 61 is a cross-sectional view of the syringe adapter and vial access device of FIG. 60 in an activated position in accordance with an aspect of the present invention.
Figure 62:
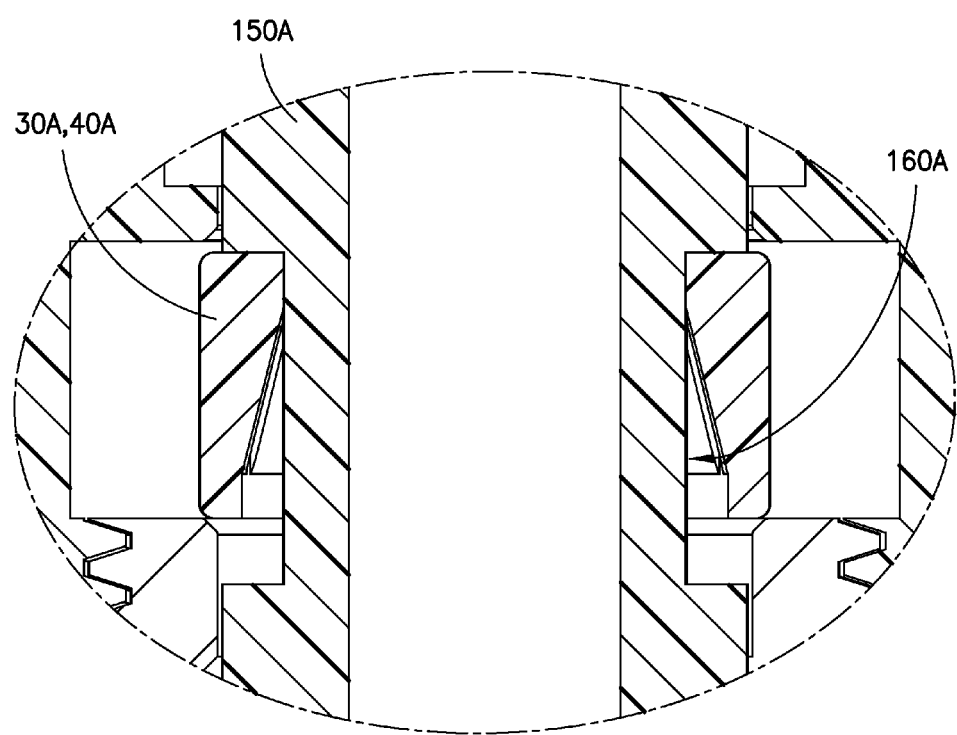
FIG. 62 is an enlarged view of a portion of the vial access device and a portion of the syringe adapter taken along section 62 of FIG. 61 in accordance with an aspect of the present invention.
Figure 63:
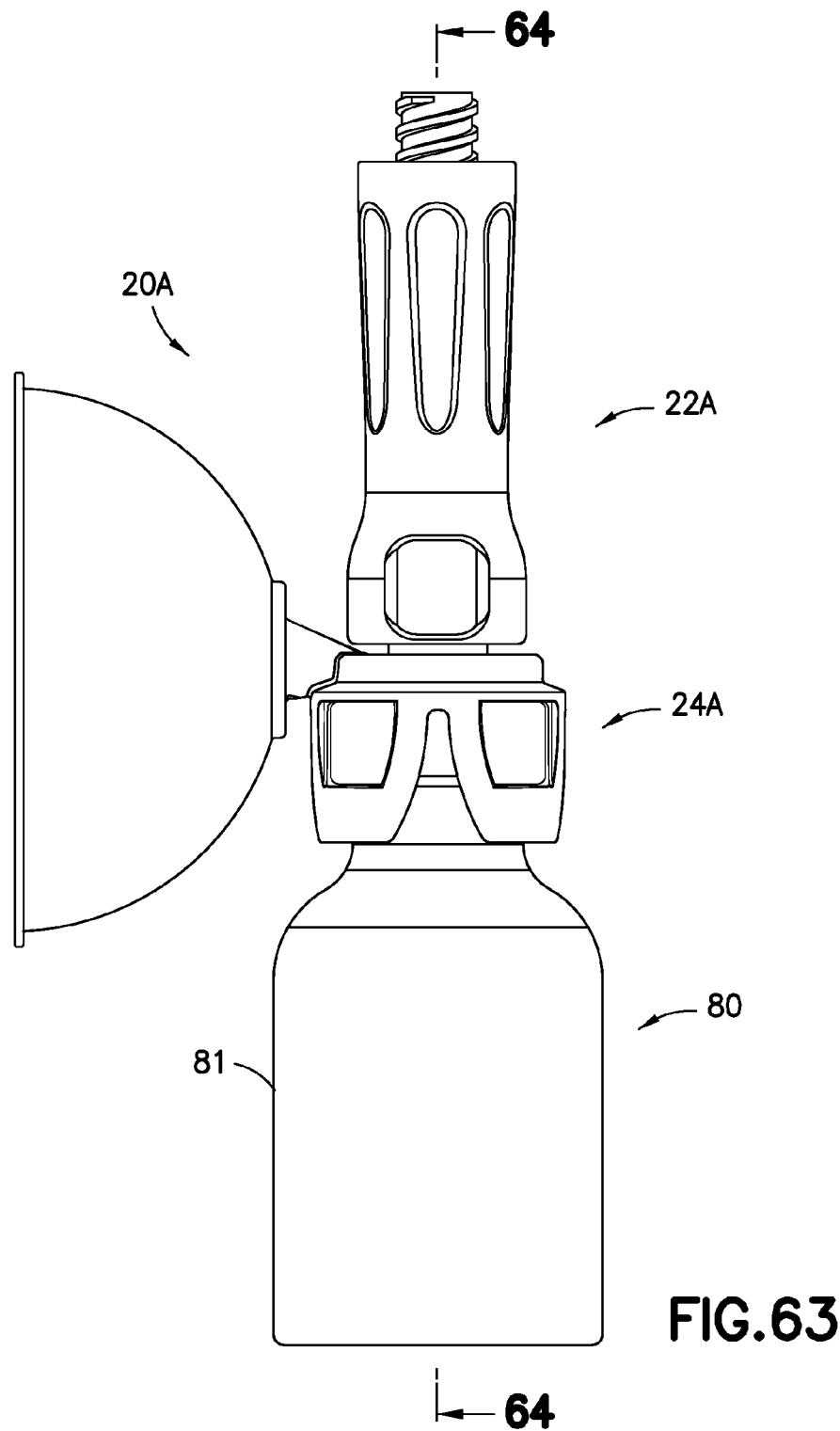
FIG. 63 is a side elevation view of a syringe adapter and vial access device in an activated position and connected to a vial in accordance with an aspect of the present invention.

In one aspect, seal membrane cavity 168 is disposed adjacent first end 162 of connection housing 150. Seal membrane cavity 168 is configured to receive seal membrane 158 as shown in FIG. 28. The pierceable seal membrane 158 provides for a liquid and gas tight seal between syringe adapter 22 and vial access device 24 during fluid transfer to minimize leakage and thereby prevent exposure of hazardous medicaments to a user. The pierceable seal membrane 158 provides a self-sealing seal that, with syringe adapter 22 and vial access device 24 attached to a vial, provides a leak-proof seal preventing any substance contained within the vial chamber from being exposed to a health care provider reconstituting, transporting, or administering a drug using system 20. In one aspect, the pierceable seal membrane 158 comprises a resilient material. For example, the pierceable seal membrane 158 is preferably a unitary device molded of any flexible, elastomeric material conventionally used for fabricating gas-proof closures. The pierceable seal membrane 158 may be formed of a natural rubber material, polyurethane elastomers, butyl rubbers, or similar materials. It is contemplated that the pierceable seal membrane 158 is formed of a material having a Shore A hardness of approximately 10 to 50. It is also envisioned that the pierceable seal membrane 158 can have other material hardness values that would provide an appropriate self-sealing material to provide a leak-proof seal with a vial septum of a vial and a syringe adapter, thereby preventing any liquid or medication residue from being exposed to a health care provider reconstituting, transporting, or administering a drug using system 20. Referring to FIG. 40, in one aspect, with the translating housing 34 in the activated position, cannula 38 pierces first seal membrane 96 and second seal membrane 98 of translating housing 34 and seal membrane 158 of vial access device 24. In this manner, the syringe adapter 22 is in fluid communication with the vial access device 24.

Referring to FIGS. 26-28, base 154 generally includes first or proximal end 170, second or distal end 172, spike member 174, piercing tip 176, fluid transfer channel 178, pressure equalization channel 180, and vial connection element 182 comprising vial grip members 184, hook protrusions 186, and angled walls 188.

System 20 is configured to establish fluid communication between a first container, e.g., a vial, and a second container, e.g., a syringe adapter and/or syringe assembly. For example, base 154 of vial access device 24 is attachable to a vial 80 as described in more detail below. Referring to FIGS. 63-67, vial 80 defining a vial size 81 may be a standard drug vial of any type having an open head portion 83 covered by a pierceable septum 84 of an elastomeric material. Walls 85 of vial 80 define vial chamber 86 for containing a substance 88. Vial 80 includes flange 87 located adjacent open head portion 83. Vial septum 84 is engaged with head portion 83 of vial 80 to seal the substance 88 within vial chamber 86. System 20 may be configured to provide a device that is capable of accommodating vials having different sizes.

Referring to FIG. 28, protruding out from base 154 at second end 172 is a piercing member or spike member 174 which includes piercing tip 176. Referring to FIG. 28, a fluid transfer channel 178 extends through spike member 174 and base 154 such that piercing tip 124 is in fluid communication with fluid channel 166 of connection housing 150. The purpose of fluid transfer channel 178 is to permit a needle cannula, such as cannula 38, to extend into vial access device 24 and to thereby permit fluid to be transferred between vial access device 24 and syringe adapter 22.

Referring to FIG. 28, a vial connection element 182 is disposed at second end 172 of base 154. In one aspect, vial connection element 182 includes a plurality of vial grip members 184 having hook protrusions 186 and angled walls 188. In one aspect, vial grip members 184 are elastically deformable. Vial grip members 184 are attachable to a vial 80 to secure system 20 to the vial 80. Each vial grip member 184 includes a hook protrusion 186 arranged to engage a corresponding flange 87 on a container such as vial 80 as shown in FIGS. 63-67. Vial connection element 182 of base 154 may be dimensioned to be attached to containers of any size and volume. In other aspects, vial connection element 182 of base 154 may include other connection mechanisms for securing vial access device 24 to vial 80 such as a threaded portion, a snap fit mechanism, locking tabs, or other similar mechanism. Each vial grip member 184 includes an angled wall 188 arranged to provide a lead-in surface to center and align vial access device 24 on a vial.

In one aspect, connection housing 150 and base 154 are a single integral component. In another aspect, connection housing 150 and base 154 are separate components and connection housing 150 is attachable to base 154 such that significant relative movement between connection housing 150 and base 154 is prevented.

Referring to FIGS. 26-28, pressure equalization system 156 includes pressure equalization housing 190 and expandable balloon 192 which includes an expansion chamber 194. Expandable balloon 192 includes a variable volume. Pressure equalization housing 190 comprises a relatively rigid material and expandable balloon 192 comprises a relatively flexible material. In one aspect, expandable balloon 192 comprises a thin, transparent plastic film that is attached to pressure equalization housing 190 in a gastight manner. In one aspect, expandable balloon 192 is designed as a bellow which is compressible and extendable and thus the volume of the expansion chamber 194 of expandable balloon 192 can thereby be increased and decreased. In other aspects, other suitable pressure equalization arrangements may be utilized. The use of a pressure equalization system with a connection system of the present disclosure provides a system for the closed transfer of fluids that provides substantially leak-proof sealing and pressure equalization during engagement of a cannula with a vial, during transfer of a substance from a vial chamber to a barrel chamber via the cannula, and during disengagement of the cannula from the vial. A pressure equalization system is not required for the connection system of the present disclosure.

Pressure equalization housing 190 provides a barrier wall member that protects expandable balloon 192 from being torn during engagement of a cannula with a vial, during transfer of a substance from a vial chamber to a barrel chamber via the cannula, and during disengagement of the cannula from the vial. In one aspect, a portion of expandable balloon 192 is not covered by pressure equalization housing 190. In this manner, expandable balloon 192 is capable of expanding in a radial direction.

In one aspect, pressure equalization housing 190 and base 154 are a single integral component. In another aspect, pressure equalization housing 190 and base 154 are separate components and pressure equalization housing 190 is attachable to base 154 such that significant relative movement between pressure equalization housing 190 and base 154 is prevented.

Referring to FIG. 28, in one aspect, pressure equalization channel 180 extends from piercing tip 176 to expandable balloon 192. In this manner, the pressure equalization channel 180 is arranged to provide gas communication between the expandable balloon 192 and the interior of a vial when vial access device 24 is connected to a vial. With vial access device 24 connected to a vial, a syringe, cannula assembly, or syringe adapter, e.g., syringe adapter 22, may be used to inject fluid into the vial or to withdraw fluid therefrom.

The function and advantages of a pressure equalization system according to the present disclosure will be described in greater detail. When preparing and administering drugs care has to be taken to minimize, or preferably eliminate the risk of exposing people, such as medical and pharmacological personnel, to toxic substances. Some drugs must be dissolved or diluted before they are administered, which involves transferring a solvent from one container to a sealed vial containing the drug in powder or liquid form, by means of a needle, for example. Drugs may be inadvertently released into the atmosphere in gas form or by way of aerosolization, during the withdrawal of the needle from the vial and while the needle is inside the vial if any pressure differential between the interior of the vial and surrounding atmosphere exists. A system of the present disclosure eliminates this problem by using pressure equalization system 156 of vial access device 24 that may be attached to a vial during the preparation of drugs. The pressure equalization system 156 includes an expandable balloon 192 which is in communication with the interior of a vial which ensures that neither an increased pressure nor a vacuum can occur inside the vial, e.g., vial 80 (FIGS. 63-67), when gas or liquid is injected into or withdrawn from the vial. In one aspect, the expandable balloon 192 may be filled with cleaned or sterilized air prior to its use to ensure that the contents of the vial do not become contaminated with air-borne particles such as dust, pollen, mold or bacteria, or other undesirable substances.

Referring to FIGS. 32-44, the use of system 20 to withdraw a medication such as substance 88 from vial 80 will now be described. Initially, referring to FIGS. 63-67, vial access device 24, 24A is attached to vial 80 as described above.

Referring to FIGS. 33-37, the translating housing 34 is in the initial position in which the syringe adapter 22 is not in fluid communication with the vial access device 24. In the position shown in FIGS. 32-37, drug transfer cannot occur between syringe adapter 22 and vial access device 24 because cannula 38 is enclosed within syringe adapter 22.

To transition system 20 from the initial position shown in FIGS. 33-37 to the activated position shown in FIGS. 38-44, push button spring 40 is transitioned from the locked position to the unlocked position. The push button spring 40 may be initially transitioned from the locked position to the unlocked position automatically when the connection housing 150 engages the push button spring 40, which can be facilitated by a tapered lead-in surface on the connection housing 150 to open the push button spring 40. Alternatively, the push button spring 40 may be initially transitioned from the locked position to the unlocked position by applying a force to first push button 130 in a direction generally along arrow A (FIG. 20) and by applying a force to second push button 132 in a direction generally along arrow B (FIG. 20) to compress the push button spring 40. Applying a force to the buttons 130, 132 or engaging the push button spring 40 with the connection housing 150 causes the width W of spring body 134 to increase and the distance D between first push button 130 and second push button 132 to decrease. In this manner, aperture 139 of push button spring 40 is increased such that spring body 134 acts as a passageway that allows movement between syringe adapter 22 and vial access device 24.

With push button spring 40 in the unlocked position, syringe adapter 22 is movable relative to vial access device 24 and translating housing 34 is movable relative to syringe adapter 22. For example, translating housing 34 is able to move axially within elongate opening 56 of syringe adapter housing 26 when connection housing 150 of vial access device 24 displaces translating housing 34. In this manner, translating housing 34 moves within syringe adapter 22 from the position shown in FIGS. 33-37 to the position shown in FIGS. 38-44. In the activated position shown in FIGS. 38-44, cannula 38 pierces first seal membrane 96 and second seal membrane 98 of translating housing 34 and seal membrane 158 of vial access device 24 so that syringe adapter 22 is in fluid communication with vial access device 24.

With translating housing 34 in the activated position shown in FIGS. 38-44, push button spring 40 transitions to the locked position in which push button spring 40 snaps into undercut 160 of connection housing 150 to lock syringe adapter 22 to vial access device 24 with translating housing 34 in the activated position as shown in FIGS. 38-44.

Figure 64:
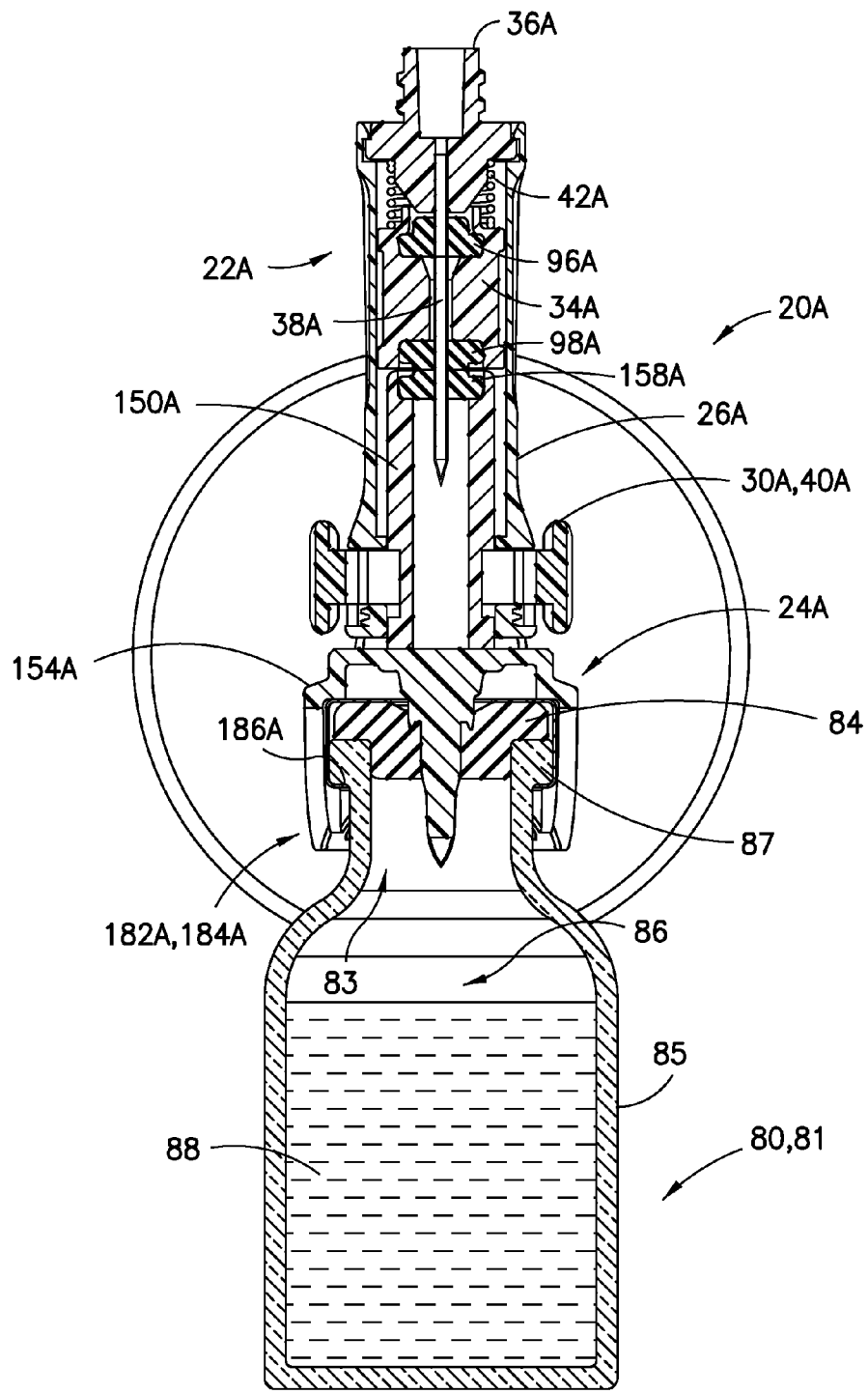
FIG. 64 is a cross-sectional view of a syringe adapter and vial access device in an activated position and connected to a vial taken along line 64-64 of FIG. 63 in accordance with an aspect of the present invention.
Figure 65:
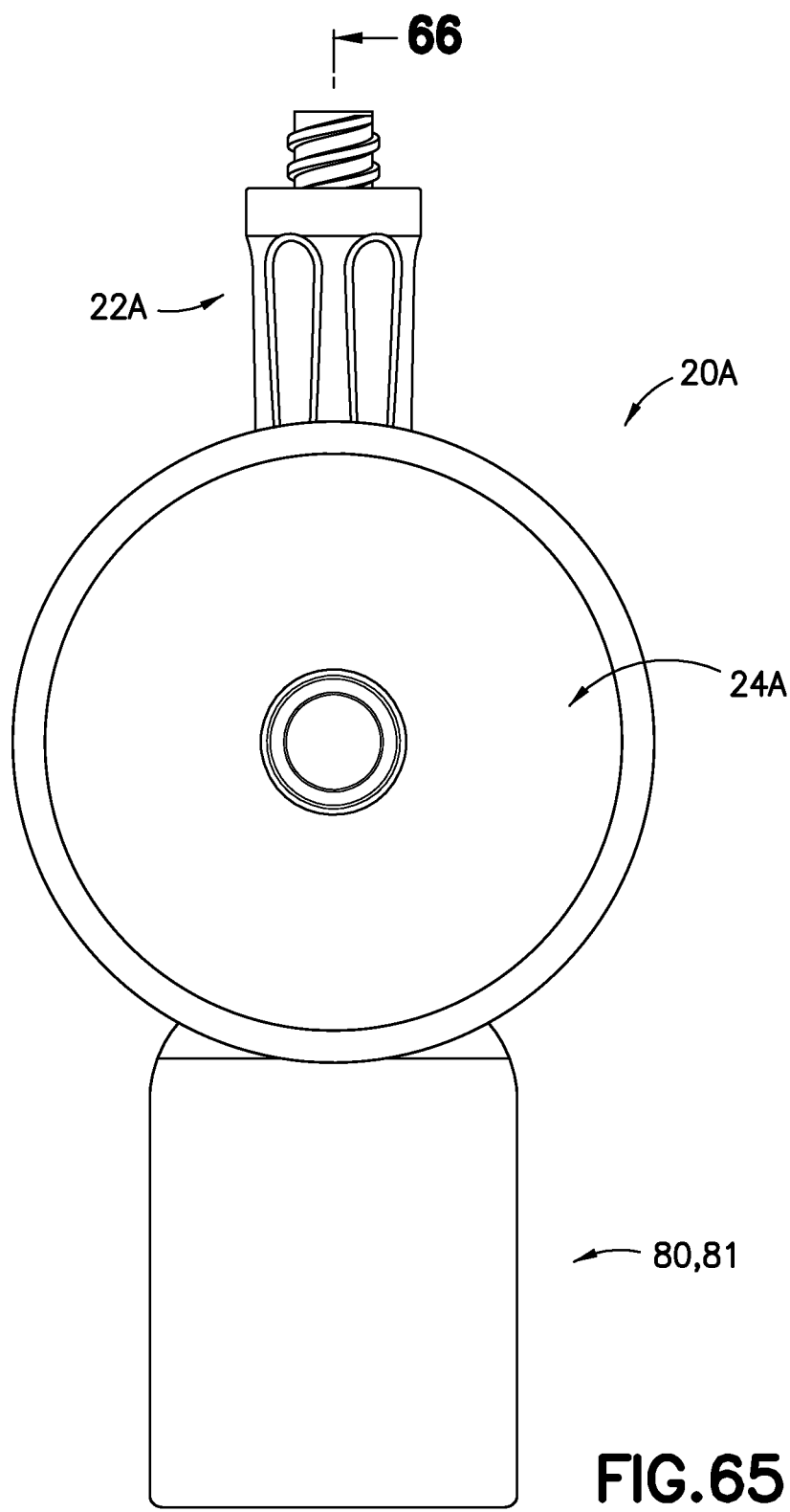
FIG. 65 is another side elevation view of a syringe adapter and vial access device in an activated position and connected to a vial in accordance with an aspect of the present invention.
Figure 66:
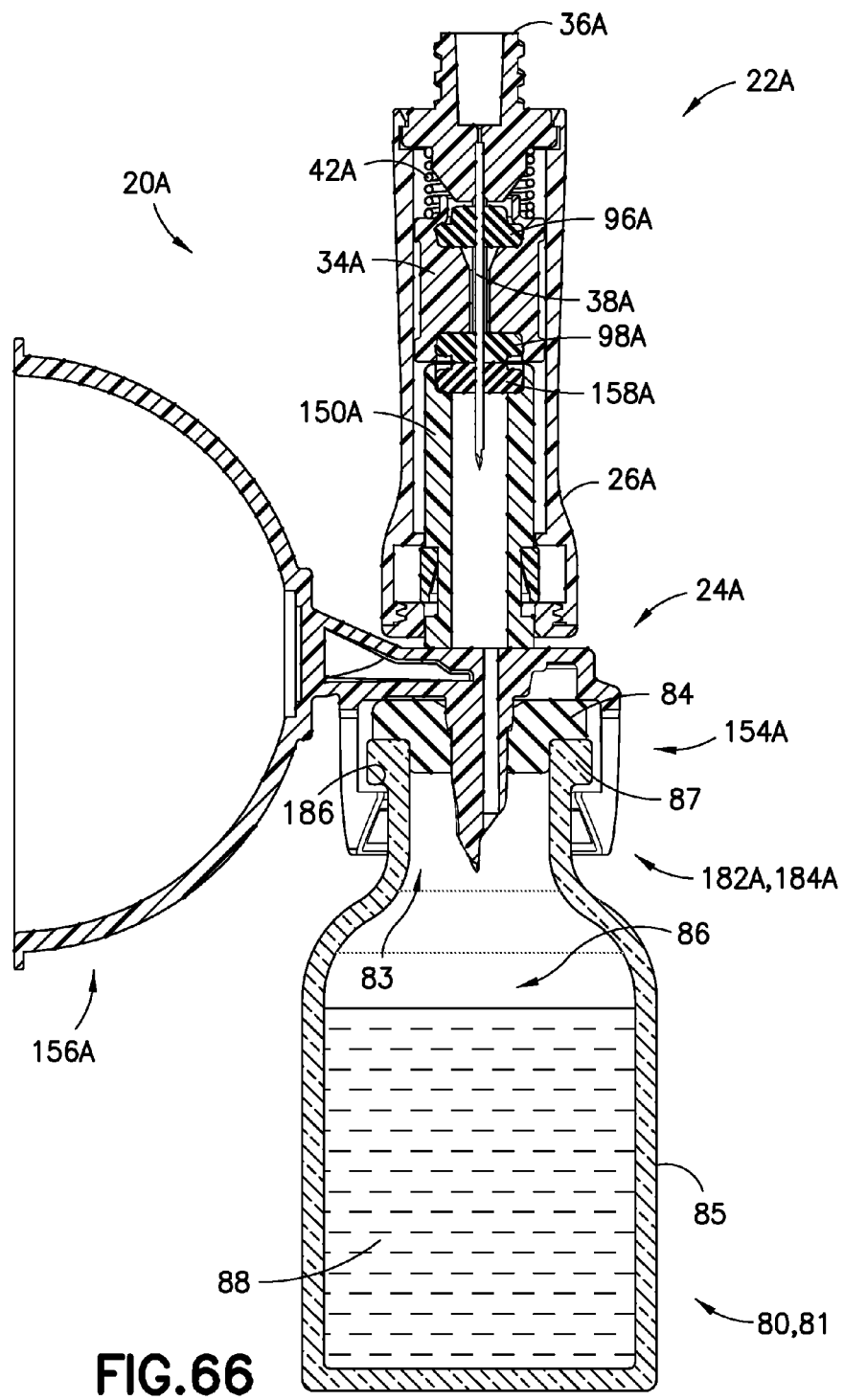
FIG. 66 is a cross-sectional view of a syringe adapter and vial access device in an activated position and connected to a vial taken along line 66-66 of FIG. 65 in accordance with an aspect of the present invention.
Figure 67:
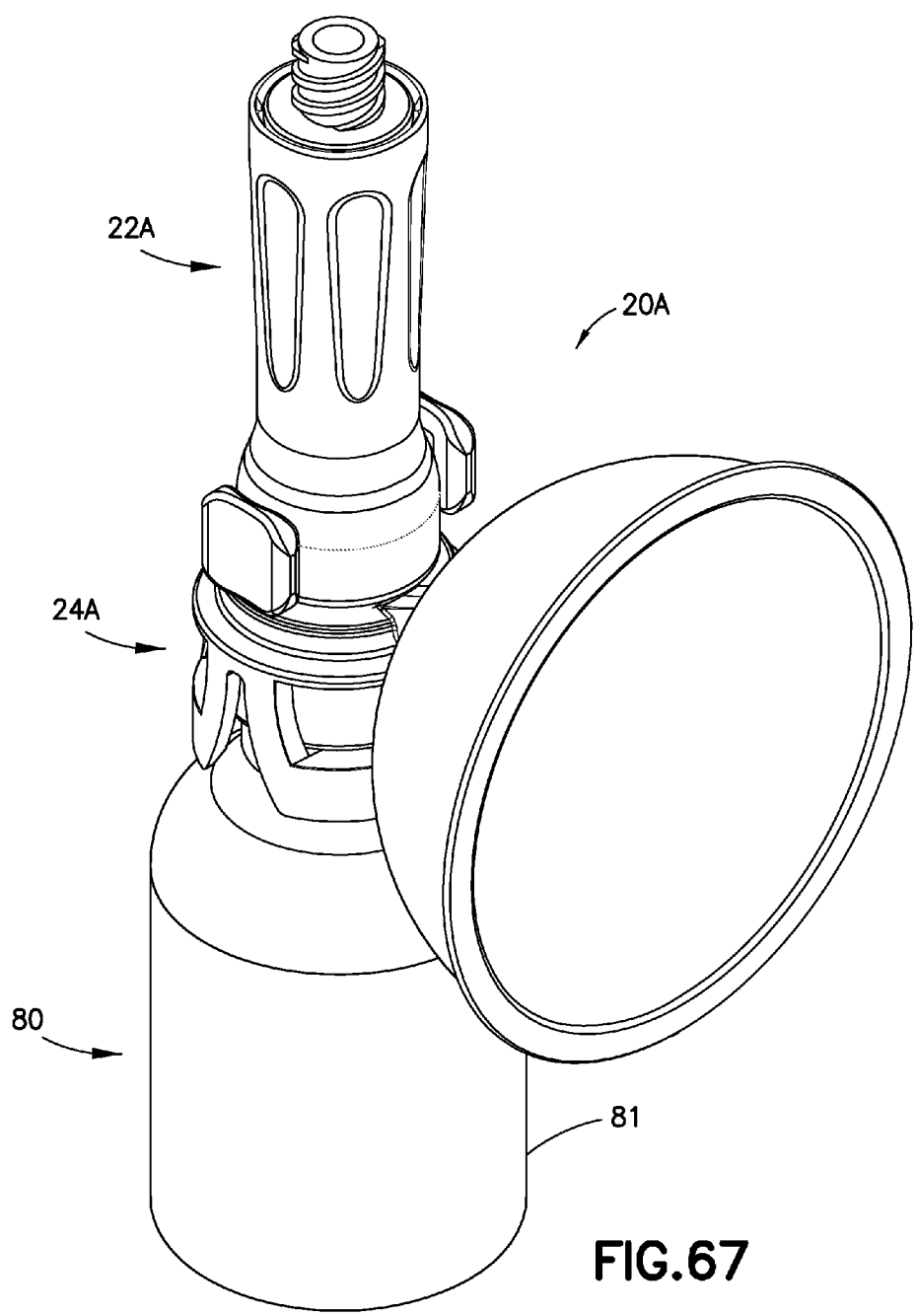
FIG. 67 is a perspective view of a syringe adapter and vial access device in an activated position and connected to a vial in accordance with an aspect of the present invention.
Figure 68:
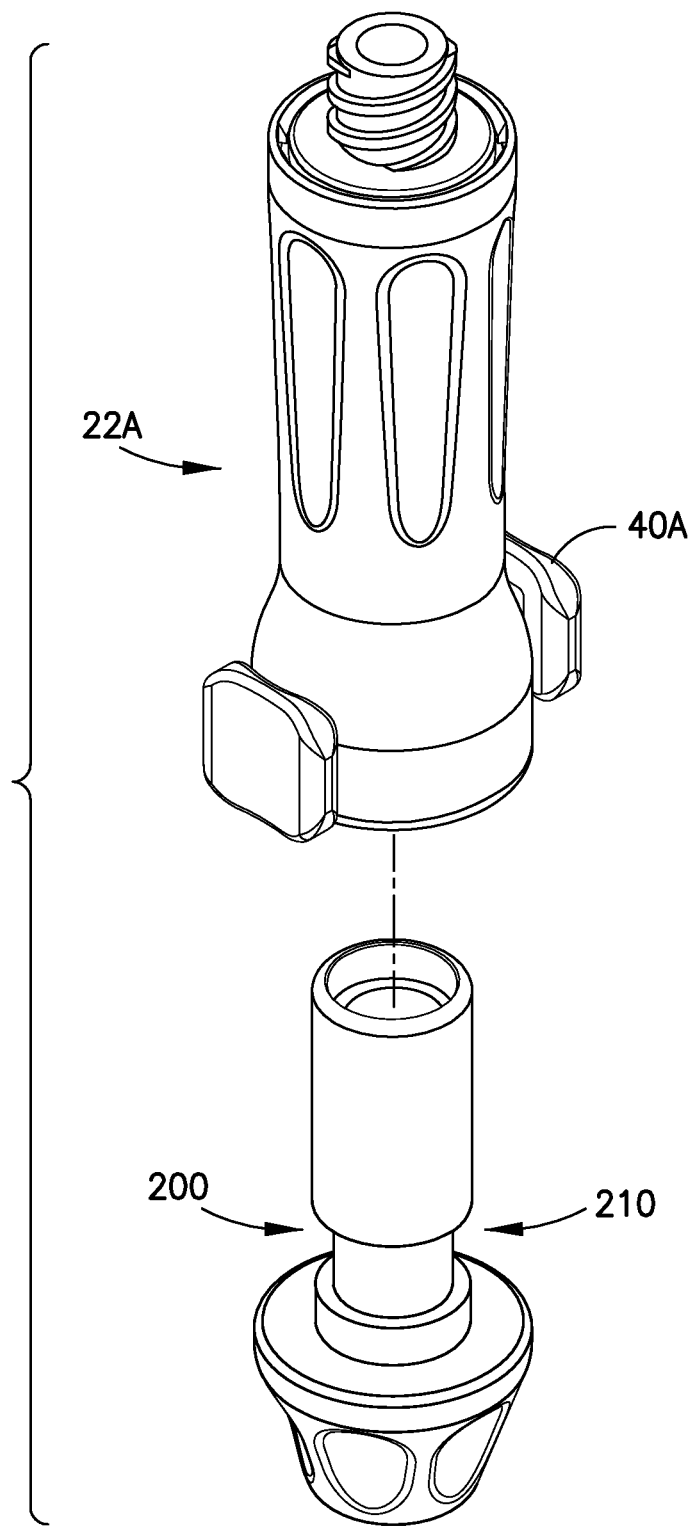
FIG. 68 is an exploded, perspective view of a syringe adapter and connector in accordance with an aspect of the present invention.
Figure 69:
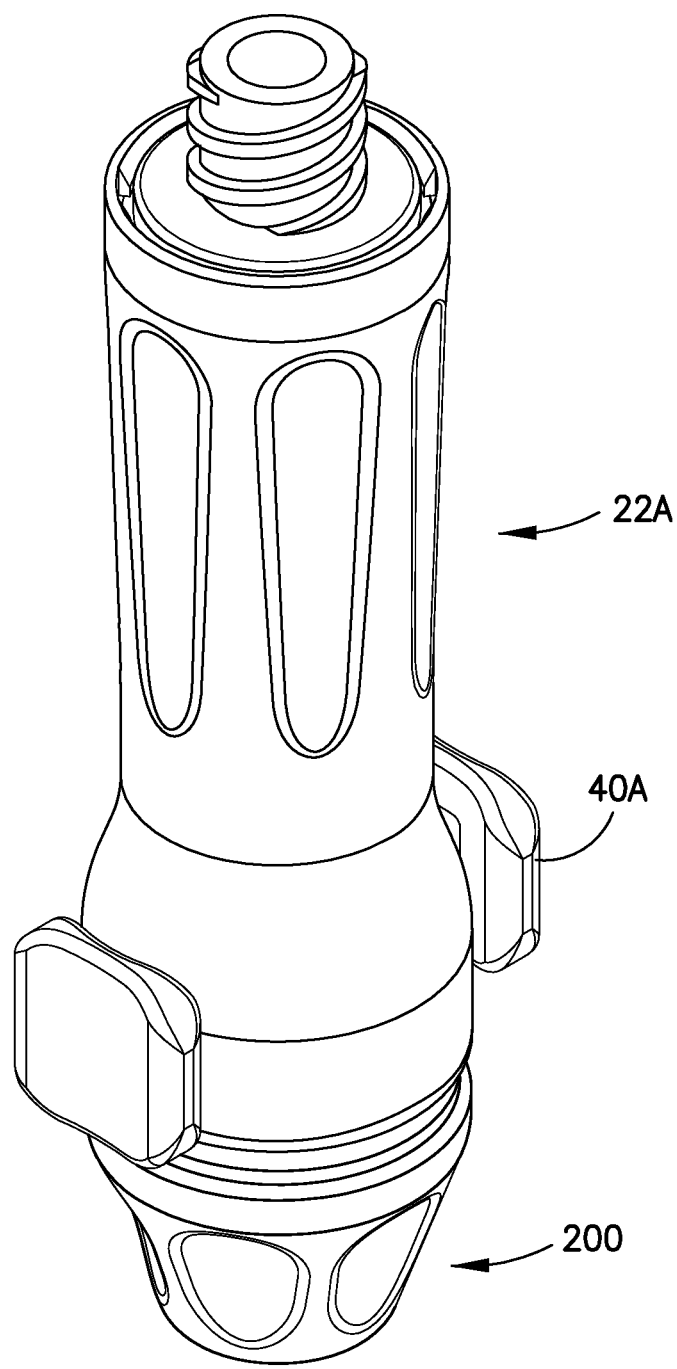
FIG. 69 is an assembled, perspective view of the syringe adapter and connector of FIG. 68 in accordance with an aspect of the present invention.
Figure 70:
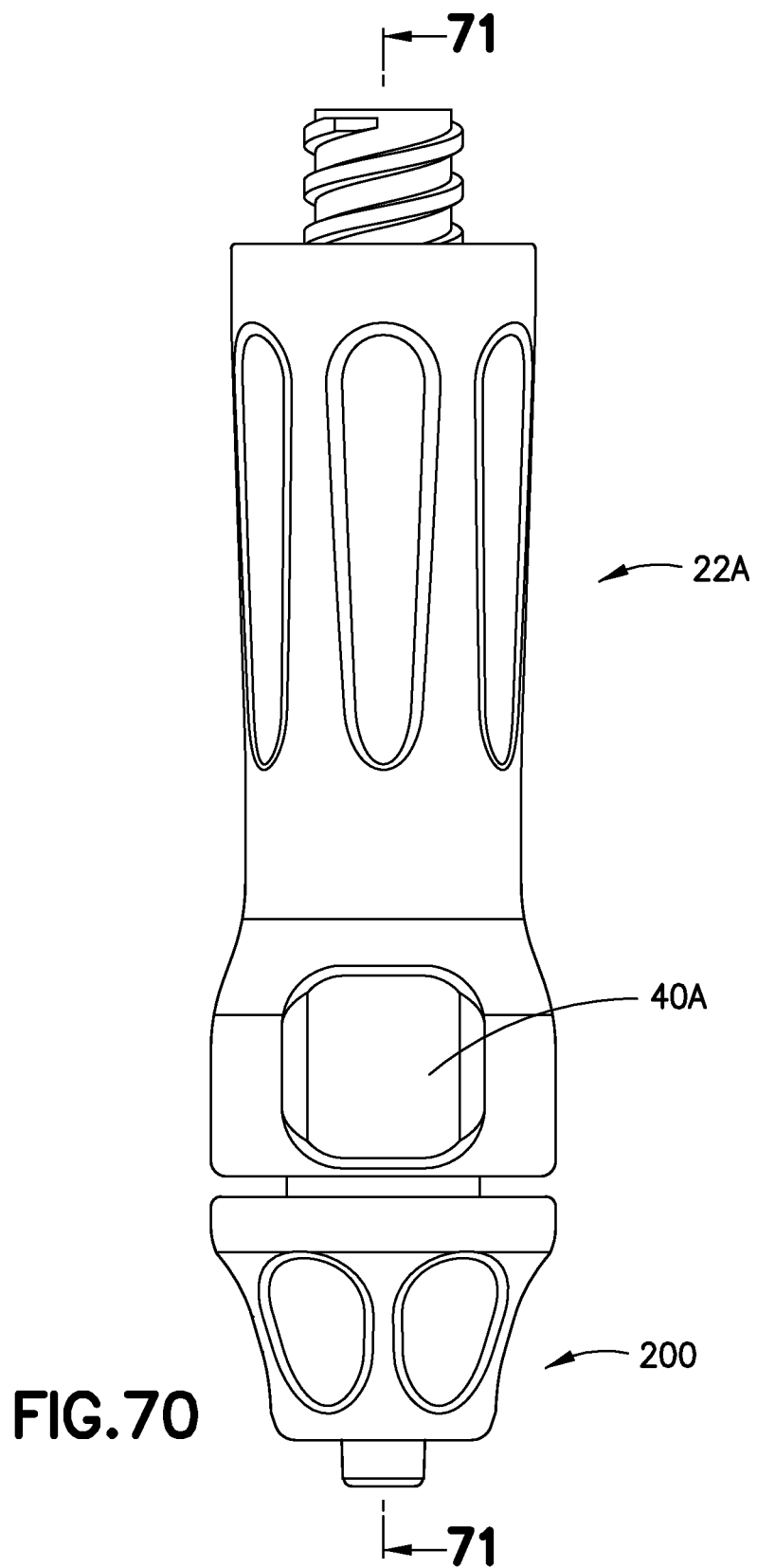
FIG. 70 is a side elevation view of a syringe adapter and connector in accordance with an aspect of the present invention.
Figure 71:
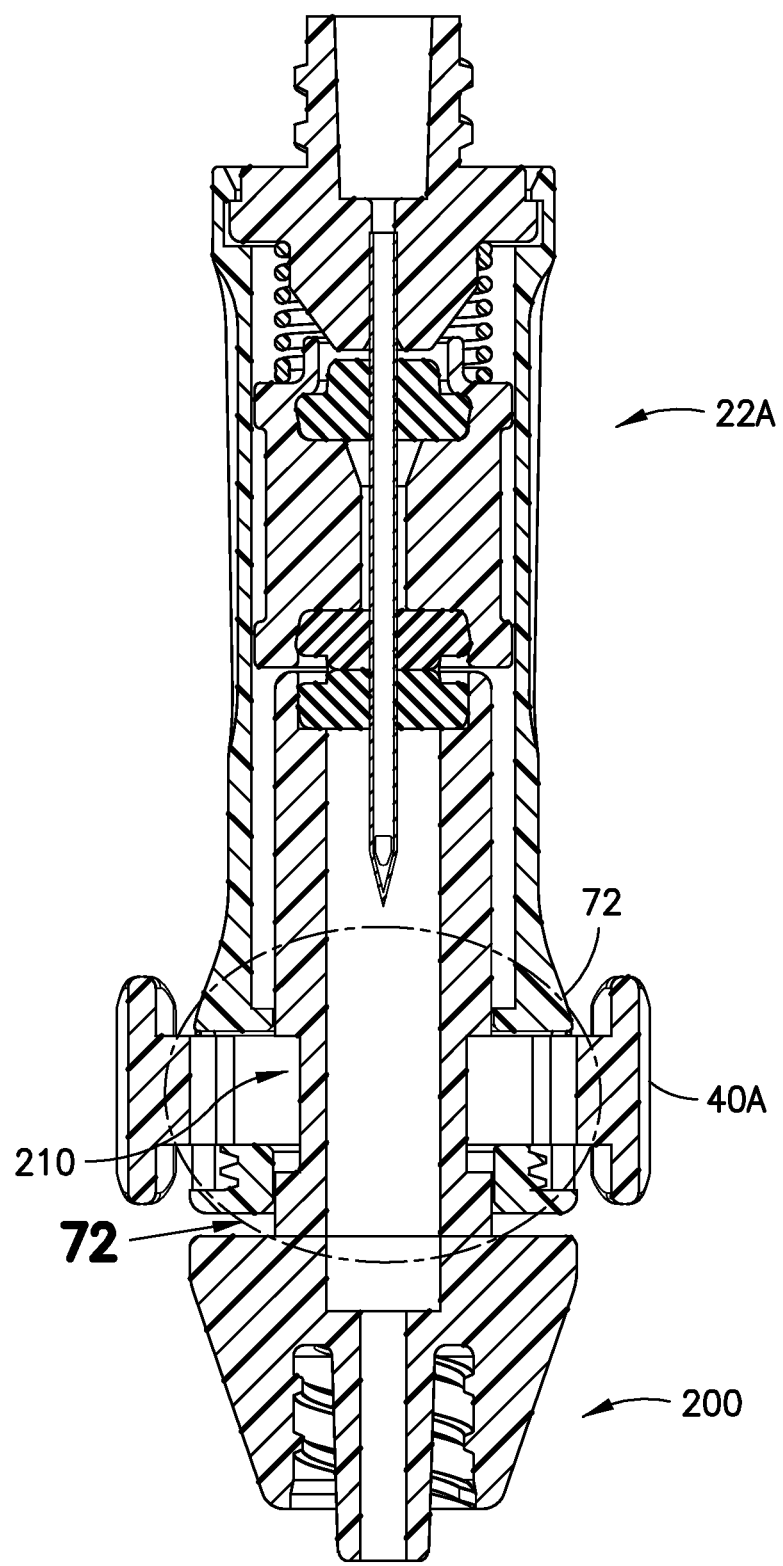
FIG. 71 is a cross-sectional view of a syringe adapter and connector taken along line 71-71 of FIG. 70 in accordance with an aspect of the present invention.
Figure 72:
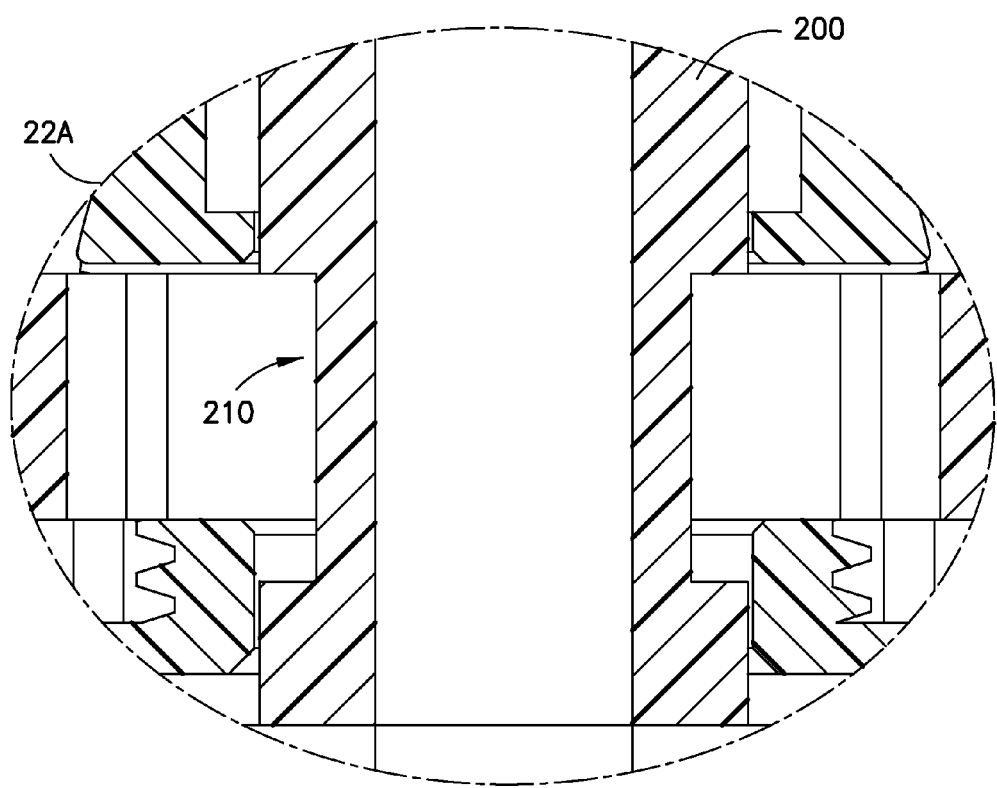
FIG. 72 is an enlarged view of a portion of the connector and a portion of the syringe adapter taken along section 72 of FIG. 71 in accordance with an aspect of the present invention.

Referring to FIG. 64, with system 20 in the activated position, vial chamber 86 of vial 80 is in fluid communication with syringe adapter 22 via cannula 38 and fluid transfer channel 178 (FIG. 28) of spike member 174. Referring to FIG. 64, with vial chamber 86 in fluid communication with syringe adapter 22, substance 88 contained within vial chamber 86 may be transferred from vial chamber 86 of vial 80 to syringe adapter 22 via cannula 38. The use of system 20 as described above provides substantially leak-proof sealing during engagement of a cannula with a vial, during transfer of a substance from a vial chamber to a barrel chamber via the cannula, and during disengagement of the cannula from the vial. The leak-proof sealing of the system 20 substantially prevents leakage of both air and liquid during use of the system 20. System 20 is compatible with a needle and syringe assembly for accessing a medication contained within a vial for administering the medication to a patient. System 20 is also compatible to be used with a drug reconstitution system. The connection between syringe adapter 22 and vial access device 24 via push button spring 40 provides for quick and intuitive coupling and decoupling of syringe adapter 22 and vial access device 24 between an initial position and an activated position as described above.

To transition system 20 from the activated position shown in FIGS. 38-44 to the initial position shown in FIGS. 33-37, push button spring 40 is transitioned from the locked position to the unlocked position by applying a force to first push button 130 in a direction generally along arrow A (FIG. 20) and by applying a force to second push button 132 in a direction generally along arrow B (FIG. 20) to compress the push button spring 40. In this manner, compression of push button spring 40 causes the width W of spring body 134 to increase and the distance D between first push button 130 and second push button 132 to decrease. In this manner, aperture 139 of push button spring 40 is increased such that spring body 134 acts as a passageway that allows movement between syringe adapter 22 and vial access device 24. During transition of system 20 from the activated position shown in FIGS. 38-44 to the initial position shown in FIGS. 33-37, the spring 42 provides a biasing force on translating housing 34, and when locking member 30 is moved from the locked position to the unlocked position, the biasing force of the spring 42 promotes translating housing 34 to move from the activated position (FIGS. 38-44) to the initial position (FIGS. 33-37).

FIGS. 45-52 and 57-67 illustrate another exemplary aspect of a system 20A of the present disclosure. The aspect illustrated in FIGS. 45-52 and 57-67 includes similar components to the aspect illustrated in FIGS. 2-23 and 26-44, and the similar components are denoted by a reference number followed by the letter A. For the sake of brevity, these similar components and the similar steps of using system 20A will not all be discussed in conjunction with the aspect illustrated in FIGS. 45-52 and 57-67.

Referring to FIGS. 45-52 and 57-67, a system for the closed transfer of fluids 20A includes a first connector or a syringe adapter 22A and a second connector or a vial access device 24A. System 20A provides substantially leak-proof sealing during engagement of a cannula with a vial, during transfer of a substance from a vial chamber to a barrel chamber via the cannula, and during disengagement of the cannula from the vial. The leak-proof sealing of the system 20A substantially prevents leakage of both air and liquid during use of the system 20A. System 20A is compatible with a needle and syringe assembly for accessing a medication contained within a vial for administering the medication to a patient. System 20A is also compatible to be used with IV bags, IV lines, patient connectors, or other aspects to move fluids between a first and second component.

Although the exemplary aspect of FIGS. 45-52 and 57-67 illustrate a first connector comprising a syringe adapter 22A and a second connector comprising a vial access device 24A, a system of the present disclosure could be utilized with any two components to move fluids therebetween. Furthermore, the connection mechanisms of the present disclosure can be reversed. For example, in one aspect, the lock portion, e.g., the undercut, can be included on a first connector or a syringe adapter 22A and the push button spring may be included on a second connector or a vial access device 24A. In one aspect, the lock portion, e.g., the undercut, can be included on a second connector or the vial access device 24A and the push button spring may be included on a first connector or a syringe adapter 22A.

Referring to FIGS. 53-56, connector 200 generally includes first or proximal end 202, second or distal end 204, sidewall 206 defining elongate opening 208 between first end 202 and second end 204, undercut 210, seal membrane cavity 212, and seal membrane 214. Undercut 210 is disposed adjacent second end 204 and is configured to receive push button spring 40 to lock syringe adapter 22 to connector 200 as described above and as shown in FIGS. 68-72. Connector 200 provides a compact and accessible connector for connecting a cartridge or barrel containing a drug, e.g., syringe adapter 22A, to an intravenous line or an injection apparatus for administering the drug to a patient. Referring to FIGS. 68-72, in one aspect, with push button spring 40A connected to syringe adapter 22A, the push button spring 40A is transitionable between an unlocked position in which syringe adapter 22A is movable relative to the connector 200 and a locked position (FIGS. 69-72) in which the push button spring 40A engages an undercut 210 of connector 200 to lock the syringe adapter 22 to the connector 200. In one aspect, with the push button spring 40A in the locked position, the spring body 134A of push button spring 40A engages the undercut 210 of connector 200 to lock the syringe adapter 22 to the connector 200 as shown in FIGS. 69-72. In one aspect, the connection mechanisms of the present disclosure can be reversed. For example, in one aspect, the lock portion, e.g., the undercut, can be included on the syringe adapter 22 and the push button spring may be included on the connector 200.

Seal membrane cavity 212 at first end 202 of connector 200 includes a pierceable barrier or seal membrane 214. The pierceable barrier membrane 214 provides for a liquid and gas tight seal between a piercing member of a barrel assembly and the pierceable barrier membrane 214 during fluid transfer of a medication to a patient so to minimize leakage and thereby prevent exposure of hazardous medicaments to a user. Barrier membrane 214 provides a self-sealing seal that, with a syringe adapter assembly attached to connector 200, provides a leak-proof seal preventing any substance being administered to a patient from being exposed to a health care provider administering the medication. In one aspect, barrier membrane 214 comprises a resilient material. For example, barrier membrane 214 is preferably a unitary device molded of any flexible, elastomeric material conventionally used for fabricating gas-proof closures. Barrier membrane 214 may be formed of a natural rubber material, polyurethane elastomers, butyl rubbers, or similar materials.

FIGS. 73-89 illustrate other exemplary aspects of a push button spring of the present disclosure. The aspects illustrated in FIGS. 73-89 includes similar components to the aspect illustrated in FIGS. 20-23, and the similar components are denoted by a reference number followed by the letters A-L. For the sake of brevity, these similar components and the similar steps of using push button springs 40A-40L will not all be discussed in conjunction with the aspects illustrated in FIGS. 73-89.

Figure 73:
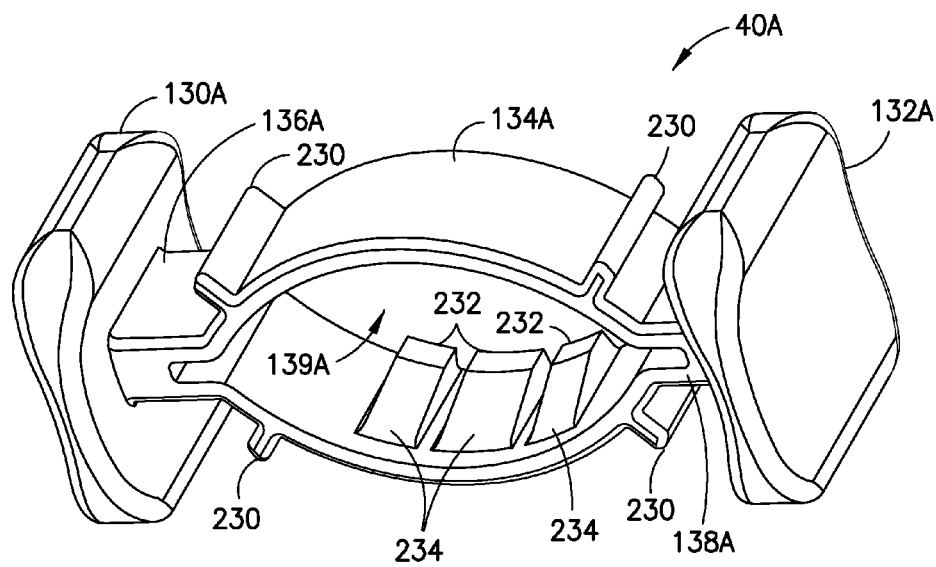
FIG. 73 is a perspective view of a push button spring in accordance with another aspect of the present invention.
Figure 74:
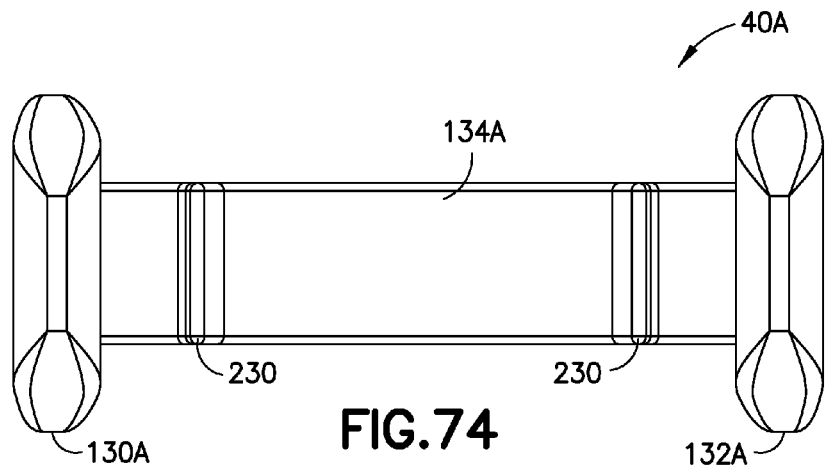
FIG. 74 is a side elevation view of a push button spring in accordance with another aspect of the present invention.
Figure 75:
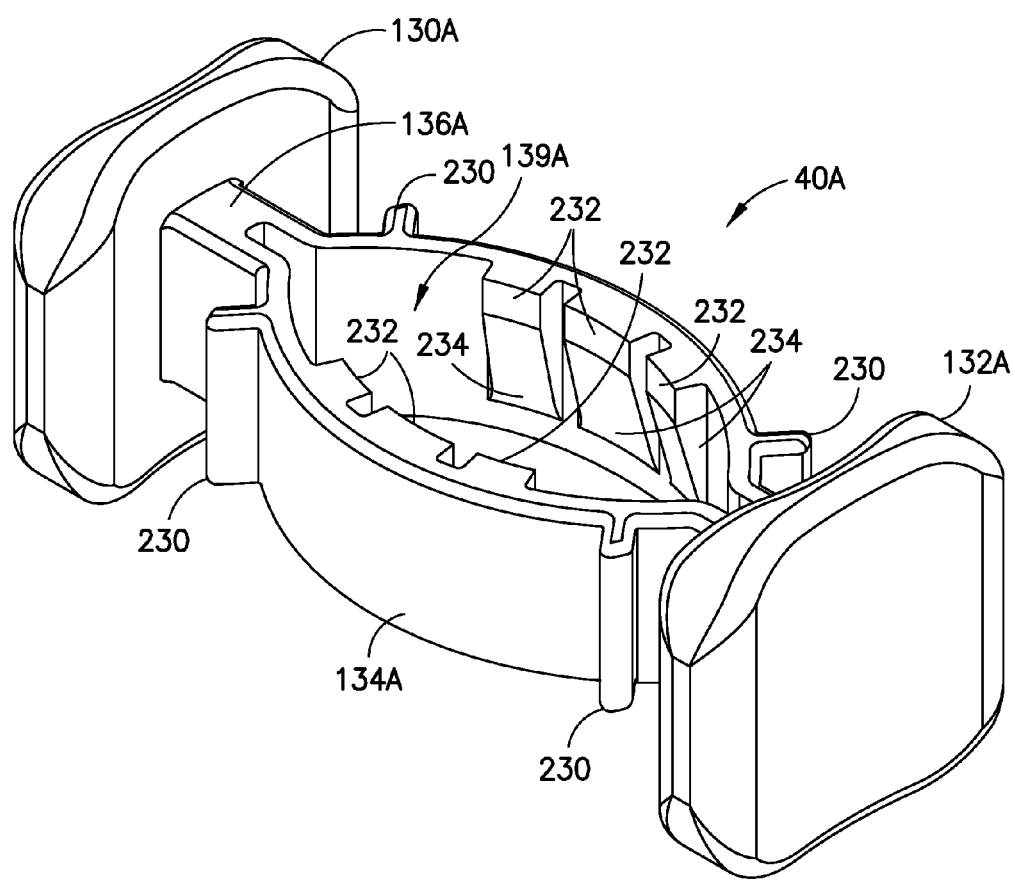
FIG. 75 is a perspective view of a push button spring in accordance with another aspect of the present invention.
Figure 76:
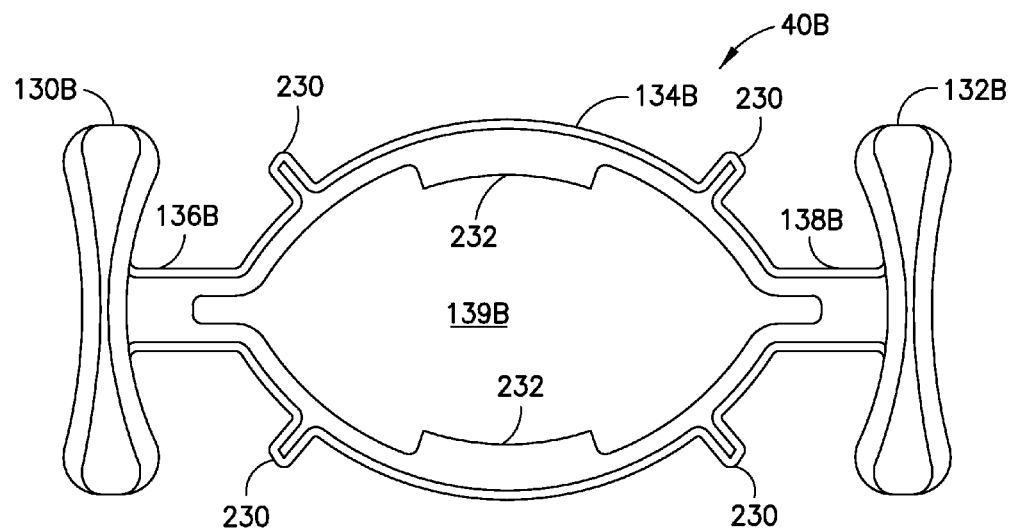
FIG. 76 is a top view of a push button spring in accordance with another aspect of the present invention.
Figure 77:
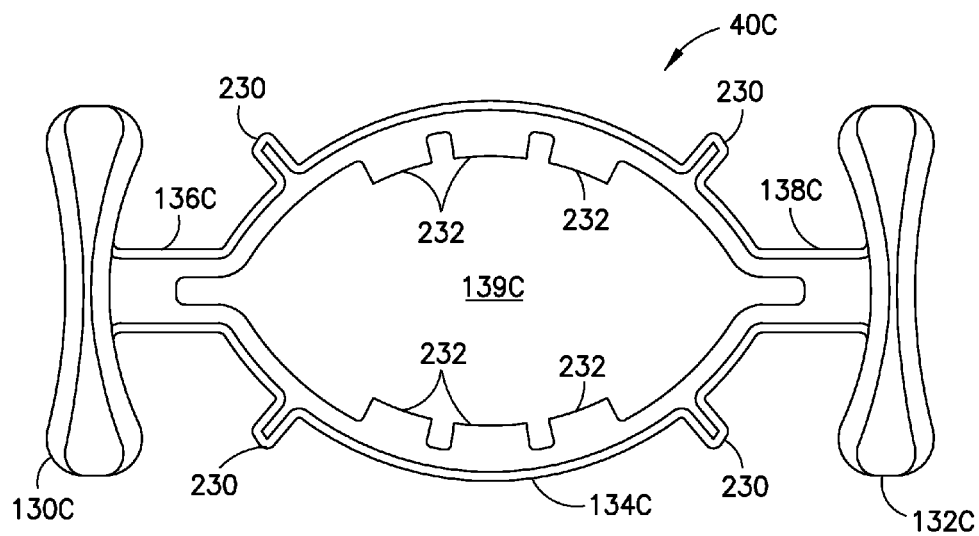
FIG. 77 is a top view of a push button spring in accordance with another aspect of the present invention.
Figure 78:
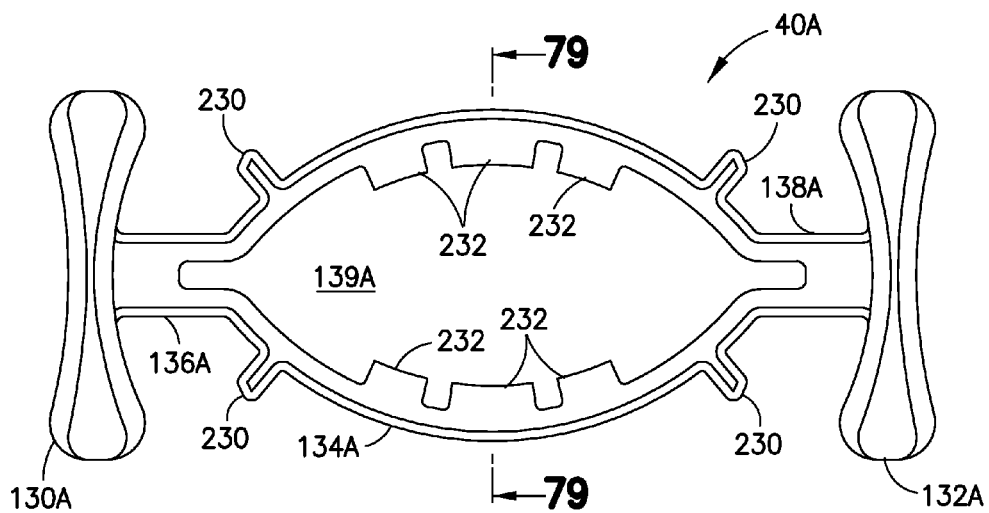
FIG. 78 is a top view of a push button spring in accordance with another aspect of the present invention.
Figure 79:
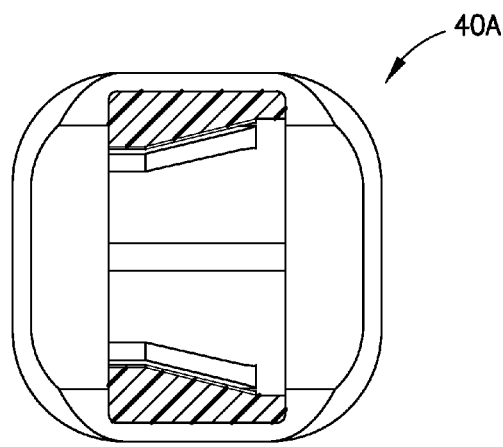
FIG. 79 is a cross-sectional view of a push button spring taken along line 79-79 of FIG. 78 in accordance with an aspect of the present invention.
Figure 80:
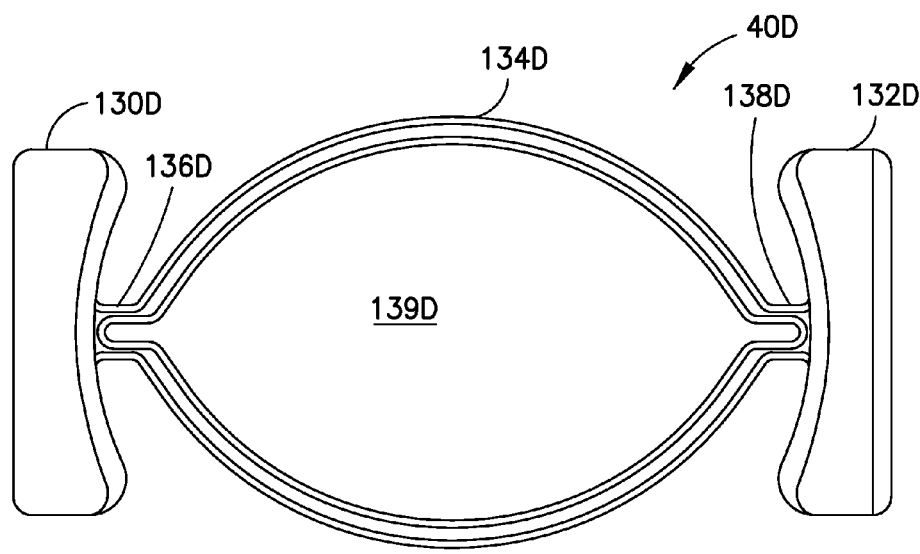
FIG. 80 is a top view of a push button spring in accordance with another aspect of the present invention.
Figure 81:
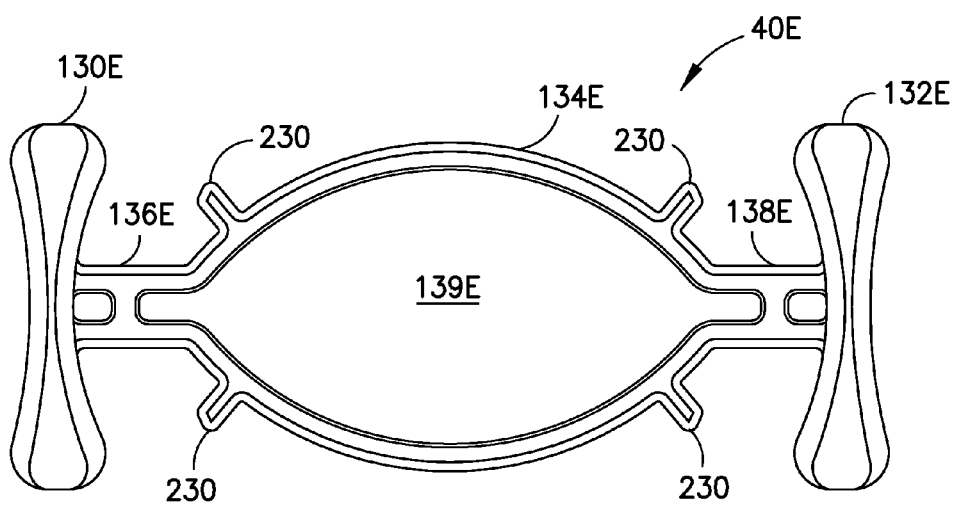
FIG. 81 is a top view of a push button spring in accordance with another aspect of the present invention.
Figure 82:
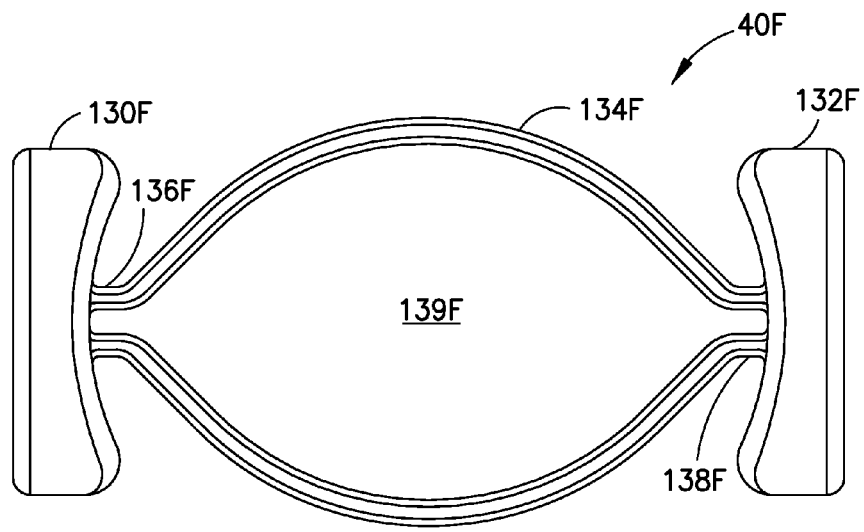
FIG. 82 is a top view of a push button spring in accordance with another aspect of the present invention.
Figure 83:
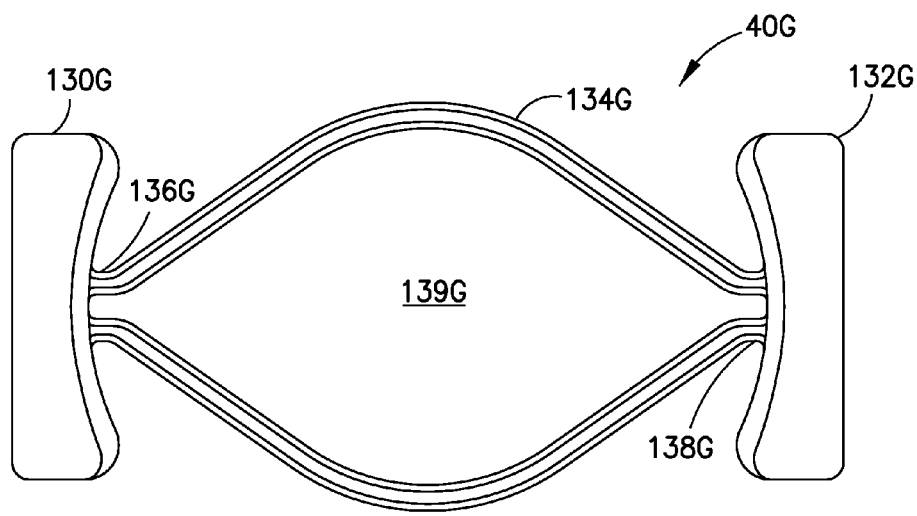
FIG. 83 is a top view of a push button spring in accordance with another aspect of the present invention.
Figure 84:
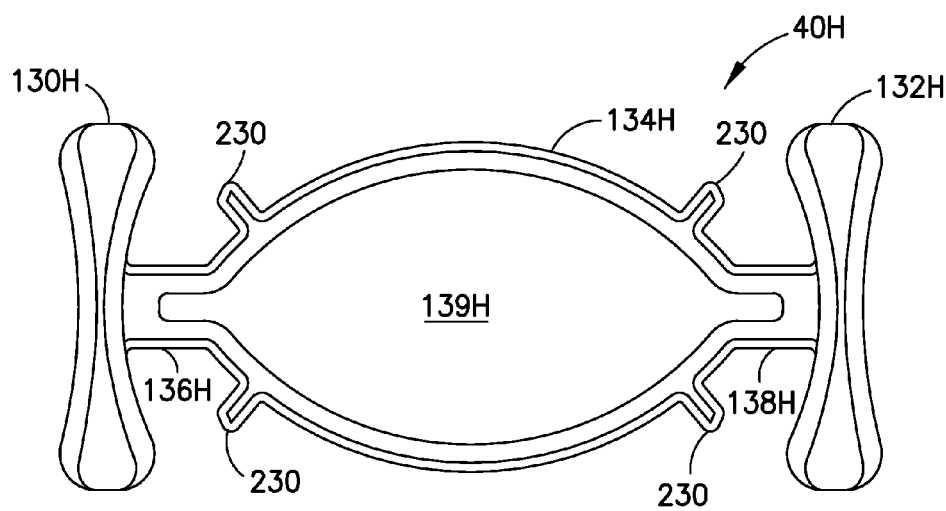
FIG. 84 is a top view of a push button spring in accordance with another aspect of the present invention.
Figure 85:
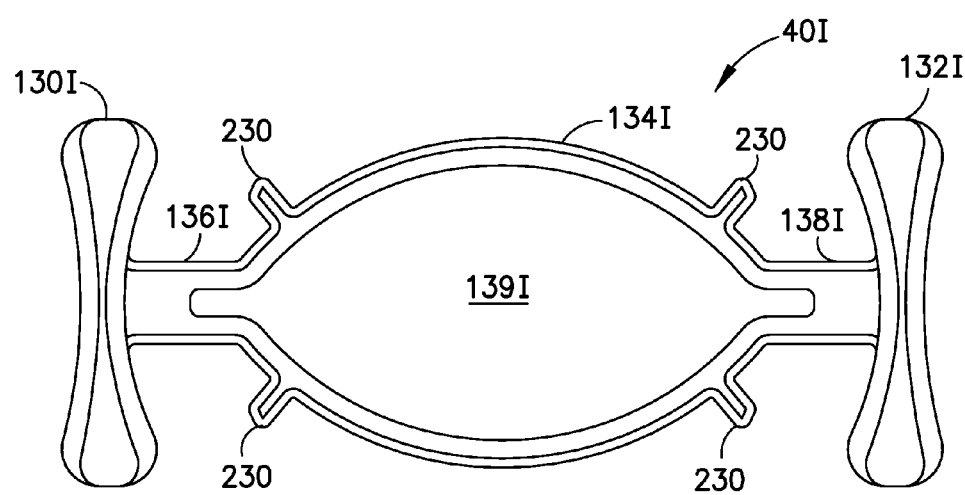
FIG. 85 is a top view of a push button spring in accordance with another aspect of the present invention.
Figure 86:
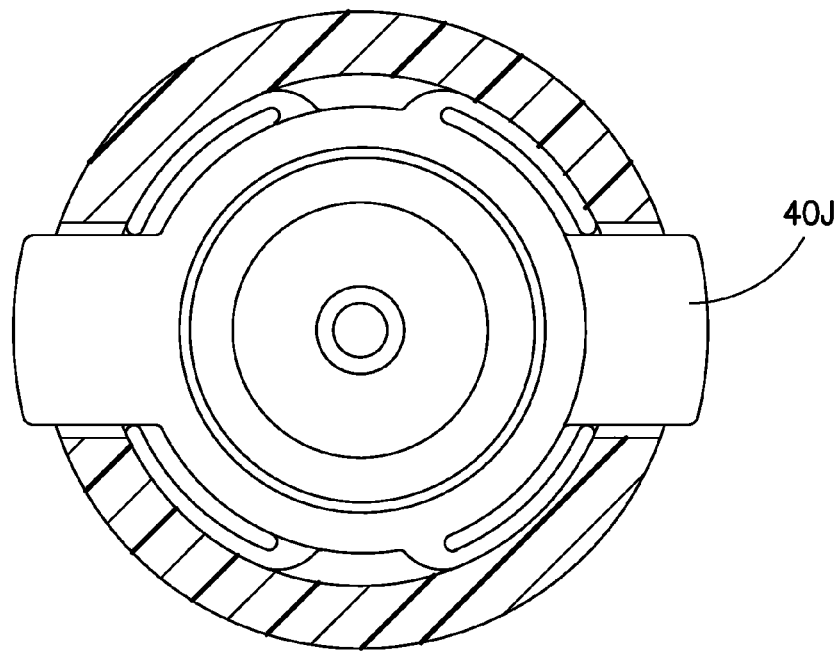
FIG. 86 is a top view of a locking member in a closed position in accordance with another aspect of the present invention.
Figure 87:
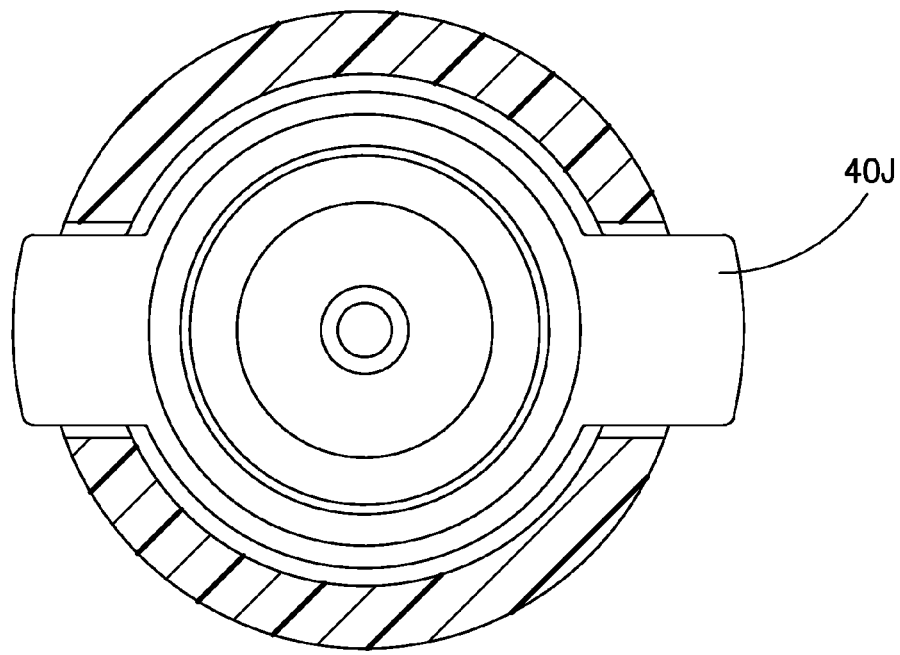
FIG. 87 is a top view of the locking member of FIG. 86 in an open position in accordance with another aspect of the present invention.
Figure 88:
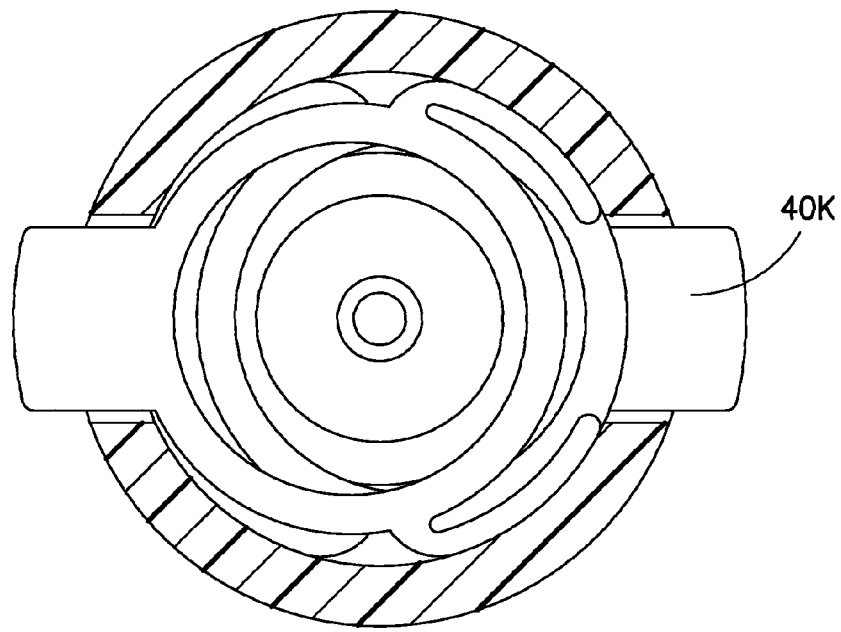
FIG. 88 is a top view of a locking member in a closed position in accordance with another aspect of the present invention.
Figure 89:
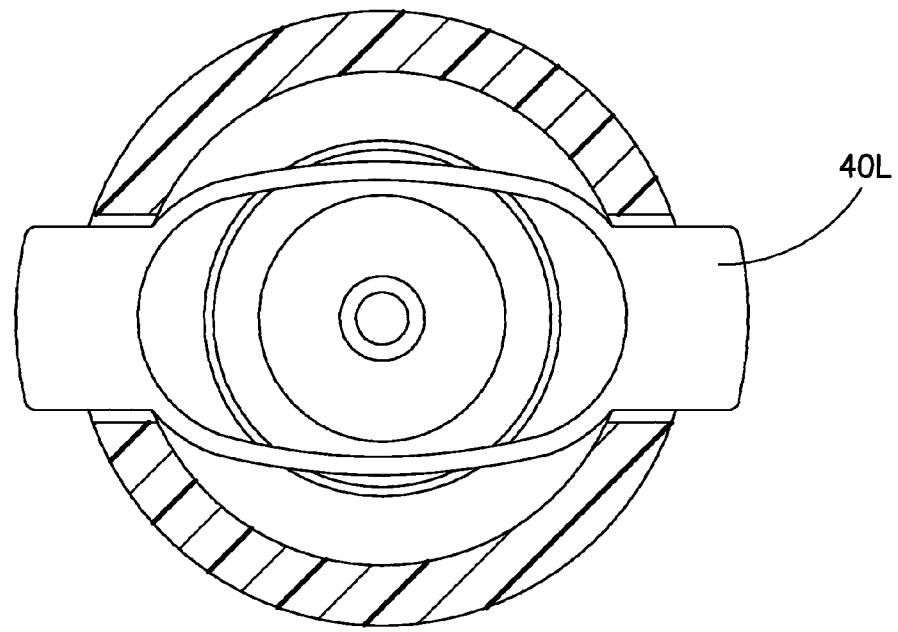
FIG. 89 is a top view of a locking member in a closed position in accordance with another aspect of the present invention.

Referring to FIGS. 73 and 75, in one aspect, push button spring 40A includes external ribs 230 located on an exterior surface of spring body 134A and internal ramps 232 located on an interior surface of spring body 134A. External ribs 230 provide a stabilizing and centering mechanism for push button spring 40A within syringe adapter housing 26. Internal ramps 232 include angled walls 234 and provide a lead-in mechanism on push button spring 40A. In one aspect, angled walls 234 may provide a lead-in mechanism which can function to automatically transition push button spring 40A from a locked position to an unlocked position. In other aspects, connection housing 150 (FIGS. 26-32) may include a lead-in surface which can function to automatically transition a push button spring from a locked position to an unlocked position. For example, the connection housing 150 may include a tapered lead-in surface. In other aspects, the connection housing 150 may include blends or angled lead-in surfaces.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A connector system for a medical device comprising:
a first connector having an elongate opening;
a second connector comprising a housing including a lock portion configured to be received within the elongate opening of the first connector, the first connector movable relative to the second connector between an initial position where the first connector is not in fluid communication with the second connector and an activated position where the first connector is in fluid communication with the second connector, the lock portion of the second connector comprising an undercut defined by a recessed portion of the housing; and
a locking member connected to the first connector, the locking member transitionable between an unlocked position where the second connector is movable within the elongate opening of the first connector and a locked position where the locking member is configured to engage the lock portion of the second connector to lock the first connector to the second connector in the activated position, wherein the locking member comprises a spring body received by the elongate opening of the first connector, and wherein the locking member is configured to engage the undercut to lock the first connector to the second connector when the first and second connectors are in the activated position and the locking member is in the locked position, and further wherein the locking member comprises at least one rib extending radially outward from the spring body,
wherein the lock portion comprises a tapered lead-in surface to automatically move the locking member from the locked position to the unlocked position when the first and second connectors are transitioned from the initial position to the activated position, and
wherein the locking member comprises ramps extending radially inward from the spring body, the ramps configured to automatically move the locking member from the locked position to the unlocked position when the first and second connectors are transitioned from the initial position to the activated position.

2. The system of claim 1, wherein the spring body is deformable between a rested state when the locking member is in the locked position and a biased state when the locking member is in the unlocked position, the spring body configured to return to the rested state.

3. The system of claim 2, wherein the spring body at least partially blocks the elongate opening of the first connector when the spring body is in the rested state, and wherein the spring body is open to receive the second connector when the spring body is in the biased state.

4. The system of claim 3, wherein the spring body is oval-shaped in the rested state and circular in the biased state.

5. The system of claim 2, wherein the locking member further comprises first and second buttons secured to the spring body, and wherein moving the first and second buttons radially inward transitions the spring body from the rested state to the biased state and moves the locking member to the unlocked position.

6. The system of claim 5, wherein the spring body is annular and the first and second buttons are positioned on opposite sides of the spring body from each other.

7. The system of claim 6, wherein the first button is connected to the spring body by a first connecting arm and the second button is connected to the spring body by a second connecting arm.

8. The system of claim 5, wherein the first and second buttons are positioned outside of the elongate opening of the first connector.

9. A system for closed transfer of fluids comprising:
a syringe adapter having a cannula, a proximal end, a distal end, and a wall defining an elongate opening between the proximal end and the distal end;
a vial access device including a lock portion;
a translating housing having a first seal membrane, the translating housing movable within the elongate opening of the syringe adapter, the translating housing transitionable between an initial position in which the syringe adapter is not in fluid communication with the vial access device and an activated position in which the syringe adapter is in fluid communication with the vial access device via the cannula; and
a locking member engaged with the syringe adapter, the locking member transitionable between an unlocked position where the lock portion of the vial access device is movable within the elongate opening of the syringe adapter and a locked position where the locking member is configured to engage the lock portion of the vial access device to lock the syringe adapter to the vial access device in the activated position, wherein the locking member comprises a spring body received by the elongate opening of the syringe adapter, the spring body being deformable between a rested state when the locking member is in the locked position and a biased state when the locking member is in the unlocked position, the spring body is configured to return to the rested state, wherein the spring body at least partially blocks the elongate opening of the syringe adapter when the spring body is in the rested state and is open to receive the vial access device when the spring body is in the biased state, and wherein the spring body defines an oval cross-sectional shape in the rested state and a circular cross-sectional shape in the biased state, and further wherein the locking member comprises at least one rib extending radially outward from the spring body, wherein the lock portion comprises a tapered lead-in surface to automatically move the locking member from the locked position to the unlocked position when the syringe adapter and the vial access device are transitioned from the initial position to the activated position, and wherein the locking member comprises ramps extending radially inward from the spring body, the ramps configured to automatically move the locking member from the locked position to the unlocked position when the syringe adapter and the vial access device are transitioned from the initial position to the activated position.

10. The system of claim 9, wherein with the translating housing in the activated position, the cannula pierces the first seal membrane of the translating housing.

11. The system of claim 9, wherein the vial access device includes a second seal membrane and with the translating housing in the activated position, the cannula pierces the first seal membrane of the translating housing and the second seal membrane of the vial access device.

12. The system of claim 9, wherein the vial access device is attachable to a vial defining a vial chamber such that the vial chamber is in fluid communication with the vial access device.

13. The system of claim 12, wherein with the vial access device attached to the vial and the translating housing in the activated position, the syringe adapter is in fluid communication with the vial chamber via the cannula.

14. The system of claim 9, wherein the syringe adapter defines a viewing window and with the translating housing in the initial position, a first indicator is displayed in the viewing window.

15. The system of claim 14, wherein with the translating housing in the activated position, a second indicator is displayed in the viewing window, the second indicator different than the first indicator.

* * * * *